(12) United States Patent
Chen et al.

(10) Patent No.: US 9,175,024 B2
(45) Date of Patent: Nov. 3, 2015

(54) PLATINUM COMPOUND HAVING AMINO OR ALKYLAMINO-CONTAINING SUCCINIC ACID DERIVATIVES AS LEAVING GROUP, PREPARATION METHOD THEREOF, AND USE THEREOF

(71) Applicant: BEIJING FSWELCOME TECHNOLOGY DEVELOPMENT CO., LTD., Beijing (CN)

(72) Inventors: Xiaoping Chen, Beijing (CN); Zejun Gao, Beijing (CN); Xiaoping Meng, Beijing (CN); Shouming Wen, Beijing (CN); Yashi Yan, Beijing (CN); Feng Zhao, Beijing (CN)

(73) Assignee: BEIJING FSWELCOME TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 14/345,384

(22) PCT Filed: Sep. 18, 2012

(86) PCT No.: PCT/CN2012/081539
§ 371 (c)(1),
(2) Date: Mar. 17, 2014

(87) PCT Pub. No.: WO2013/041014
PCT Pub. Date: Mar. 28, 2013

(65) Prior Publication Data
US 2014/0349985 A1 Nov. 27, 2014

(30) Foreign Application Priority Data

Sep. 19, 2011 (CN) .......................... 2011 1 0278380

(51) Int. Cl.
| | | |
|---|---|---|
| *C07F 15/00* | (2006.01) | |
| *A61K 31/282* | (2006.01) | |
| *A61K 31/555* | (2006.01) | |
| *C07C 67/343* | (2006.01) | |
| *C07C 227/04* | (2006.01) | |
| *C07C 227/18* | (2006.01) | |
| *C07D 295/15* | (2006.01) | |
| *A61K 45/06* | (2006.01) | |

(52) U.S. Cl.
CPC ........... *C07F 15/0093* (2013.01); *A61K 31/282* (2013.01); *A61K 31/555* (2013.01); *A61K 45/06* (2013.01); *C07C 67/343* (2013.01); *C07C 227/04* (2013.01); *C07C 227/18* (2013.01); *C07D 295/15* (2013.01)

(58) Field of Classification Search
CPC  A61K 31/282; C07F 15/0093; C07C 67/343; C07C 227/04; C07C 227/18; C07D 295/15
USPC ............... 556/137; 549/206; 548/403; 546/6; 514/492

See application file for complete search history.

(56) References Cited

U.S. PATENT DOCUMENTS

| | | | |
|---|---|---|---|
| 4,322,362 A | 3/1982 | Kaplan et al. | |
| 6,262,094 B1 | 7/2001 | Hoefle et al. | |
| 2004/0162342 A1* | 8/2004 | Sohn et al. .................... | 514/492 |
| 2006/0205677 A1 | 9/2006 | Gao et al. | |
| 2010/0197890 A1 | 8/2010 | McTavish | |
| 2014/0349985 A1 | 11/2014 | Chen et al. | |

FOREIGN PATENT DOCUMENTS

| | | |
|---|---|---|
| CN | 88101195 A | 9/1988 |
| CN | 1698903 | 11/2005 |
| CN | 101475600 A | 7/2009 |
| CN | 102276657 A | 12/2011 |
| CN | 102276674 A | 12/2011 |
| CN | 102286050 A | 12/2011 |
| DE | 4138042 A1 | 5/1993 |
| JP | 6137794 | 2/1986 |
| JP | S61249993 A | 11/1986 |
| WO | 9008157 A1 | 7/1990 |
| WO | 9719086 A1 | 5/1997 |
| WO | 9730992 A1 | 8/1997 |
| WO | 9822461 A1 | 5/1998 |
| WO | 9825929 A1 | 6/1998 |
| WO | 9838192 A1 | 9/1998 |
| WO | 9854966 A1 | 12/1998 |
| WO | 9901124 A1 | 1/1999 |
| WO | 9902224 A1 | 1/1999 |
| WO | 9902514 A2 | 1/1999 |
| WO | 9903848 A1 | 1/1999 |
| WO | 9907692 A2 | 2/1999 |
| WO | 9924416 A1 | 5/1999 |
| WO | 9927890 A2 | 6/1999 |
| WO | 9928324 A1 | 6/1999 |

(Continued)

OTHER PUBLICATIONS

International Preliminary Report on Patentability and Written Opinion dated Mar. 25, 2014 for Application No. PCT/CN2012/081539.
D. Gibson et al., "Anthraquinone Intercalators as Carrier Molecules for Second-Generation Platinum Anticancer Drugs," Eur. J. Med. Chem., vol. 32, No. 10, 1997, pp. 823-831.
Caron, G. et al., "The Relevance of Polar Surface Area (PSA) in Rationalizing Biological Properties of Several Cis-Diammineralonatoplatinum(II) Derivatives," ChemNedChem, vol. 4, No. 10, Jul. 27, 2009, pp. 1677-1685.

(Continued)

*Primary Examiner* — Porfirio Nazario Gonzalez
(74) *Attorney, Agent, or Firm* — Lando & Anastasi, LLP

(57) ABSTRACT

Disclosed are a category of platinum compounds having amino- or alkylamino-containing succinato derivatives as leaving group, or pharmaceutically acceptable salts thereof, preparation method thereof, and medicinal compositions containing the compounds. Also disclosed is a use of the compounds in treating cell proliferative diseases, especially cancers. The platinum compounds of the present invention have high water solubility and small toxic side effect.

38 Claims, No Drawings

(56) References Cited

FOREIGN PATENT DOCUMENTS

| | | | |
|---|---|---|---|
| WO | 9943653 | A1 | 9/1999 |
| WO | 9954318 | A1 | 10/1999 |
| WO | 9954319 | A1 | 10/1999 |
| WO | 9954330 | A1 | 10/1999 |
| WO | 9965913 | A2 | 12/1999 |
| WO | 9967252 | A2 | 12/1999 |
| WO | 9967253 | A2 | 12/1999 |
| WO | 0000485 | A1 | 1/2000 |
| WO | 2006091790 | A1 | 8/2006 |

OTHER PUBLICATIONS

Jakupec et al., "Tumor-inhibiting platinum complexes-state of art and future perspectives," Rev. Physiol Biochem Pharmacol., 2003, 146, pp. 1-53.

SG Bagrova, Vopr Onkol, 2001, 47(6): 752-756.

Chinese Search Report issued on Mar. 23, 2015 for Application No. 2012800231310 (English language translation not available).

European Search Report dated Mar. 30, 2015 for Application No. 12833075.0.

Wang et al., "Antitumor Platinum Drugs in accord with Classical Structure-Activity Relationships," Chemistry Online (http://www.hxtb.org) Dec. 2003, pp. 828-836.

Wang et al., "Synthesis, Characterization and Anti-tumor Activities of a Series of Platinum (II) Complexes with 1R,3S-1,2,2-Trimethylcyclopentanediamine," Chinese Journal of Inorganic Chemistry, vol. 20, No. 7, Jul. 2004, pp. 775-780.

Zhang et al., "Design and synthesis of highly water-soluble platinum antineoplastic drugs," China Medical Herald, pp. 120-122.

* cited by examiner

US 9,175,024 B2

PLATINUM COMPOUND HAVING AMINO OR ALKYLAMINO-CONTAINING SUCCINIC ACID DERIVATIVES AS LEAVING GROUP, PREPARATION METHOD THEREOF, AND USE THEREOF

FIELD OF THE INVENTION

The present invention relates to a category of platinum compounds for treating cell proliferative diseases in particular, relates to a category of platinum compounds having amino- or alkyamino-containing succinato derivatives as leaving group, preparation methods and use thereof.

BACKGROUND OF THE INVENTION

Cancer (malignant tumor) is one of the leading diseases threatening the human life today. The morbidity and mortality of cancers have increased sharply in recent years. The tumor development trend revealed by the World Health Organization indicated that, the annual global newly confirmed tumor patients were more than 10,000,000 since 1996. As of the end of 1996, the global total tumor patients had exceeded 40,000,000. Approximately 7,000,000 persons die of various cancers all around the world each year. In 2001, the world morbidity and mortality of tumor had increased by 22% from 1990. Cancer has become the second main cause of death just second to cardiovascular and cerebrovascular diseases. The most commonly seen cancers are lung cancer, breast cancer, colorectal cancer, gastric cancer, liver cancer, cervical cancer, esophageal cancer, and bladder cancer. The authoritative survey data on the morbidity and mortality of cancers in China in 2006 published on the tenth National Clinical Oncology Conference showed that, the cancer deaths were 3,000,000 in China in 2006. There are approximately 2,120,000 newly confirmed cancer patients each year. Lung cancer is on the top of the mortality of malignant tumor. Experts estimated that, by 2020, the death toll will exceed 4,000,000; by 2025, tumor will become the first major cause for global death toll.

There are three means for clinically treating cancers: surgery, radiotherapy and chemotherapy. Antitumor drugs are the most commonly used way of the treatment. In 2008, the global market sale of antitumor drugs is US$ 48 billion. At present, clinical antitumor drugs are mainly classified into alkylating agent, antimetabolites, metal platinum, plant alkaloids and other crude drugs, cytotoxic antibiotics, etc. Platinum antitumor drugs are a sort of principal antitumor drugs and cisplatin was firstly developed in 1960s. The important difference from traditional cytotoxic antitumor drugs is their unique mechanism of action and excellent selectivity. The major target is DNA, which is cross-linked inter and intra DNAs and forms platinum complex~DNA complex, to disturb DNA replication or combine with nucleoprotein and plasmosin, belonging to cell cycle nonspecific agent (CCNSA). Cis-dichlorodiamminoplatinum, i.e., Cisplatin, Cis-1,1-cyclobutanedicarboxylate platinum, i.e., Carboplatin, Cis-glycolic acid-diammine platinum i.e., Nedaplatin, oxalate-(trans-L-1,2-cyclohexyl diamine) platinum i.e., Oxaliplatin, Cis-[(4R,5R)-4,5-bi-(aminomethyl)-2-isopropyl 1,3-dioxane](bidentate) platinum, i.e., Sunpla, and 1,2 diaminomethyl-cyclobutane-lactate platinum i.e., Lobaplatin etc. have been successfully developed one after another. Platinum antitumor drugs are characterized by wide antitumor spectrum, good effect, etc. Moreover, they are well combined with other antitumor drugs. This not only improves the inhibition ratio of the existed tumor, but also expands antitumor spectrum, thus consolidating the position of platinum antitumor drugs in clinical treatment. In the ranking among hundreds of antitumor drugs conducted by the World Health Organization (WHO) in 1995, cisplatin ranks the second in the comprehensive evaluation on curative effect and market. Statistical data indicate that, among all chemotherapy regimens in China, more than 70%~80% are dominated by platinum or compatible with platinum drugs.

Platinum antitumor drugs, however, now with high toxicity, have many defects, including bone marrow suppression, nephrotoxicity, nerve injury, etc., poor solubility, comparatively narrow anticancer spectrum, drug resistance, etc. Therefore, designing and synthesizing new platinum antitumor drugs remain one of the leading directions for the present antitumor drug research (M A Jakuper, M. Galanski, B. K. Keppler. Tumour-inhibiting platinum complexes-state of art and future perspectives, Rev. Physiol Biochem Pharmacol, 2003, 146, 1-53)

Substantive studies have been conducted in recent two years to reduce the toxic and side effects of platinum chemotherapy drugs, improve curative effect, reduce tumor recurrence and avoid drug resistance, and improve the water solubility of platinum compounds. For example, the solubility is 2.65 mg/ml for cisplatin, 7.9 mg/ml for recently developed Oxaliplatin, 17.8 mg/ml for Carboplatin, and 27 mg/ml for Minoplatin. Comparing with cisplatin, the toxic and side effects of Oxaliplatin and Carboplatin are reduced. The deficiency is that the solubility of above so-called water-soluble platinum compounds remains slight soluble or sparingly soluble. Murray A. Plan et al prepared the sodium alcoholate salt for platinum compounds, which effectively improved the solubility externally (U.S. Pat. No. 4,322,362A), but the compounds must be dissolved under the condition above pH10 and the toxicity has still not been effectively solved. Giulia C et al also prepared series of platinum compounds. However, the solubility of those compounds was still not remarkably improved (Chem Med Chem, 2009, 4(10), 1677-1685). WO2006091790A1 also made public a series of platinum compounds with specific structure, but similarly, the solubility was still not distinctively improved. Cycloplatinum synthesized by Russian Kurnakov Institute of Ordinary and Inorganic Chemistry is a cis-[S-(−) malate] .ammonia.cyclopentylamino platinum (II), which can prolong the life of the animals that suffer from leukemia and hepatoma, without renal toxicity, and the myelosuppression is dose limited toxicity (S G Bagrova, Vopr Onkol, 2001, 47(6): 752756). American Bioscience, based on cycloplatinum, developed the compound coded as ADP, the chemical name was Cis-(2 amino succinato).(1S,2S-cyclohexyl diamine) platinum (II), displaying activity for traditional platinum anti-drug resistance (US Bioscience. Pharma Projects, 1998: a1744~a1745). Although ADP has amino, the solubility remains lower; moreover, it cannot form salt with acid; the anti-tumor intensity is very weak and the toxicity is relatively great. Therefore, the existing technology still requires the platinum compounds with high solubility, less toxicity, and higher anti-tumor efficacy.

SUMMARY OF THE INVENTION

The present invention provides a category of platinum compounds that are used for the treatment of proliferating diseases, in particular platinum compounds with the leaving group of succinato derivative containing amino and alkylamino radical, their pharmaceutical acceptable salts, solvates, stereoisomers or their precursors. Comparing with the existing platinum antitumor drugs, the aqueous solubility of the compounds in the invention has been greatly improved, and the toxicity and side effects have been significantly reduced, and unexpected technical effects have been produced. The structure of the compounds is showed in formula A:

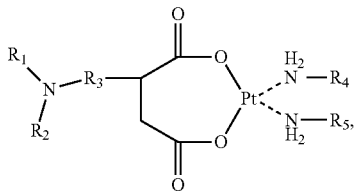

(A)

Wherein:

$R_1$ and $R_2$ may be the same or different, including but not limited to hydrogen, alkyl, naphthenic base, alkoxy alkyl, alkyl amino alkyl, heterocycle, alkenyl, and alkynyl; wherein alkyl, alkoxy alkyl, alkyl amino alkyl and heterocycle may be unsubstituted or optionally substituted, preferably substituted by halogen, hydroxyl, alkoxy, alkyl, alkoxy alkyl, naphthenic base, heterocycle; $R_1$ and $R_2$ may form saturated or unsaturated carboncycle or heterocycle with the atom connected and the carboncycle or heterocycle formed may be unsubstituted or optionally substituted, preferably substituted by halogen, hydroxyl, alkoxy, alkyl, alkoxy alkyl, naphthenic base, heterocycle; provided that the ring that formed by $R_1$, $R_2$ or $R_1$ and $R_2$ contains unsaturated bond, the atom of the unsaturated bond cannot be directly connected with nitrogen atom.

$R_3$ may be but not limited to alkyl, naphthenic base, —$R_{31}$—O—$R_{32}$—; $R_{31}$ and $R_{32}$ are independently selected from bond or alkyl; $R_{31}$ is connected with nitrogen atom; the alkyl or naphthenic base above may be unsubstituted or optionally substituted, preferably substituted by halogen, hydroxyl, alkoxy, alkyl, alkoxy alkyl, naphthenic base, heterocycle, etc.;

$R_4$ and $R_5$ may be the same or different, may be but not limited to hydrogen, hydroxyl, alkyl, naphthenic base, alkoxy, alkoxy alkyl, alkyl amino alkyl, heterocycle, alkenyl, or alkynyl; wherein alkyl, alkenyl, alkynyl naphthenic base, alkoxy alkyl, alkyl amino alkyl and heterocycle may be unsubstituted or optionally substituted, preferably substituted by halogen, hydroxyl, alkoxy, straight chain or branched-chain alkyl, alkoxy alkyl, naphthenic base, and heterocycle;

$R_4$, $R_5$ and the atoms may connect to form closed rings of four-membered, five-membered, six-membered, seven-membered or eight-membered ring; the above rings may be optionally condensed with other rings and may be optionally substituted.

Preferably, $R_1$ and $R_2$ are selected from hydrogen, $C_{1-8}$ alkyl, $C_{3-6}$ naphthenic base, alkoxy alkyl, alkyl amino alkyl, or heterocycle respectively; $R_3$ is selected from $C_{1-10}$ alkyl, $C_{3-6}$ naphthenic base; $R_4$ and $R_5$ are selected from hydrogen, hydroxyl, $C_{1-8}$alkyl, $C_{3-6}$ naphthenic base, alkoxy, alkoxy alkyl, or heterocycle.

More preferably, the present invention provides the compounds in the formula B and their pharmaceutically acceptable salts:

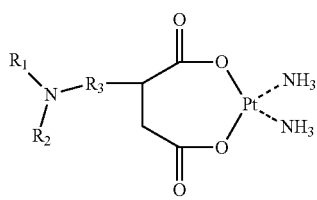

(B)

Wherein $R_1$, $R_2$, $R_3$ are described as above.

Most preferably, $R_1$ and $R_2$ are hydrogen, methyl, ethyl or propyl group respectively; or the closed ring formed by $R_1$, $R_2$ and the atoms connected thereof is pyrrolidinyl or piperidyl; $R_3$ is methyl, ethyl, propyl, isoprypyl, normal-butyl, isobutyl, tertiary butyl or pentyl.

The present invention further provides the compounds in the formula C and their pharmaceutically acceptable salts, solvent, isomer or precursor, i.e. the compounds obtained when $R_4$, $R_5$ and the atoms connected form a closed ring together. The structural formula is as follows:

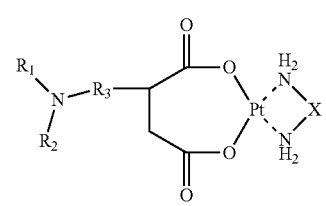

(C)

Wherein, the group where $R_1$, $R_2$, $R_3$ are selected as described above,

is preferred but not limited to the following:

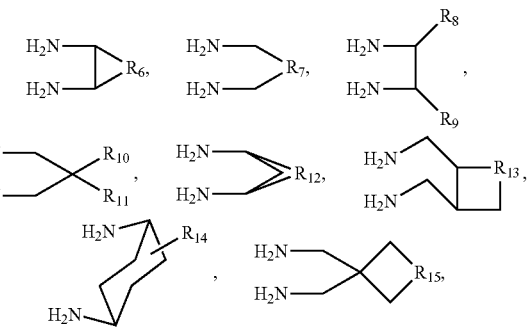

and the structures above may also be optionally connected with various appropriate substitutent groups.

The platinum compounds in formula (C), wherein $R_6$ may be but not limited to $(CH_2)_a$; wherein a=1-6, preferably 3-5, the most preferably 4; wherein some —$CH_2$— may be substituted by —O—. One or more hydrogens of $(CH_2)_a$ may be substituted by fluorine, alkyl, hydroxyl or alkoxy, etc; the preferred compound is (±) trans-1,2-cyclohexyl diamine-platinum (II), (±) trans-1,2-cyclopentamethylenediamine platinum (II), (±) trans-1,2-cyclobutanediamine platinum (II) and (±) trans-1,2-cyclopropane diamine platinum (II).

$R_7$ may be but not limited to $(CH_2)_b$, wherein b=0-3, preferably b=0-2; wherein some —$CH_2$— may be substituted by —O—, and one or more hydrogen of $(CH_2)_b$ may be substituted by halogen, alkyl, hydroxyl, hydroxyalkyl or alkoxy, heterocycle.

$R_8$ and $R_9$ may be but not limited to hydrogen, halogen, hydroxyl, hydroxyalkyl, alkyl, alkoxy, heterocycle, etc; $R_8$ and $R_9$ may be the same or different, preferably hydroxyalkyl, and the most preferably hydroxymethyl (F).

$R_{10}$ and $R_{11}$ may be but not limited to hydrogen, halogen, hydroxyalkyl, alkyl, alkoxy, heterocycle, etc. $R_{10}$ and $R_{11}$ may be the same or different, preferably hydroxyalkyl, and the most preferably hydroxymethyl.

$R_{12}$ may be but not limited to $(CH_2)_m$, wherein m=2-4, wherein some —$CH_2$— may be substituted by —O—. One or more hydrogen of $(CH_2)_m$ may be substituted by halogen, alkyl, hydroxyl or alkoxy, heterocycle.

$R_{13}$ may be —$CH_2$— or —O—, preferably —$CH_2$—.

$R_{14}$ may be hydrogen, halogen, alkyl, alkoxy, heterocycle, hydroxyalkyl or hydroxyl. $R_{14}$ is preferably selected from hydrogen.

$R_{15}$ may be but not limited to $(CH_2)_n$, —$(CH_2)_n$—O—, —$CH_2$—O—$CH_2$—; wherein n=1-3, preferably —$CH_2$—O—$CH_2$—; one or more hydrogen of —$CH_2$—O—$CH_2$— may be substituted by alkyl, alkoxy, heterocycle, hydroxyl, or hydroxyalkyl, etc.

The structure of the preferred compounds is as follows:

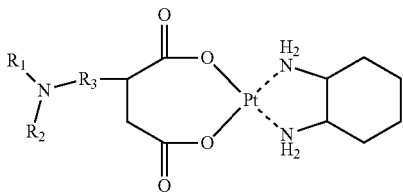
(D1)

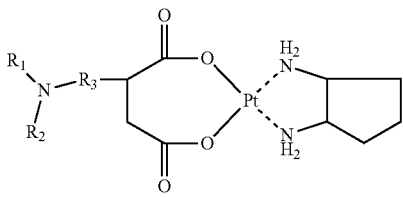
(D2)

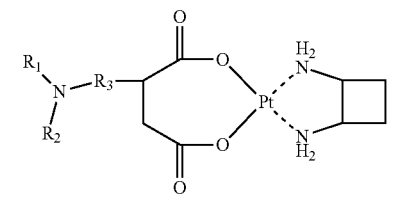
(D3)

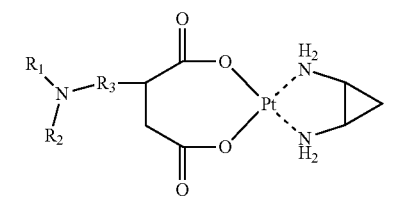
(D4)

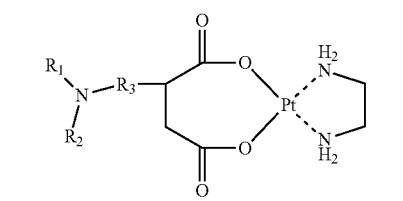
(E1)

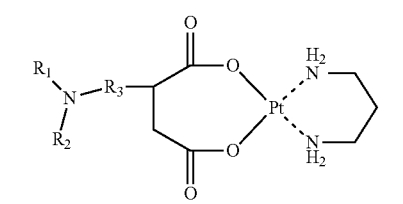
(E2)

-continued

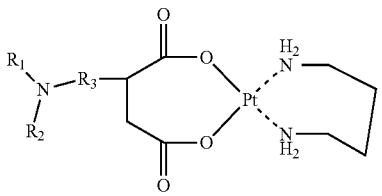
(E3)

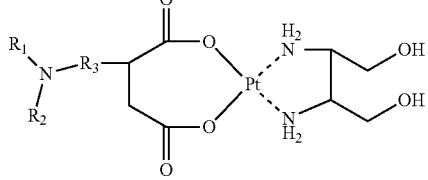
(F)

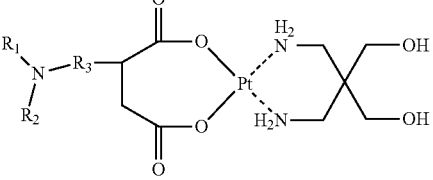
(G)

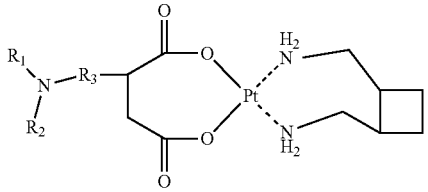
(H)

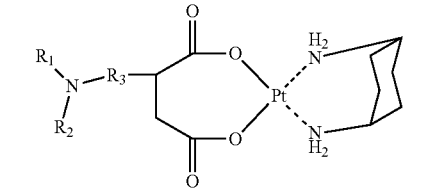
(I)

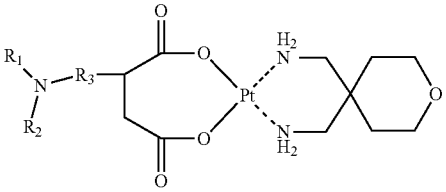
(J)

The most preferred compounds of the present invention include:

Compound 1: [2-(2-methylaminoethyl)-succinato].[Cis-diamine]platinum (II);
Compound 2: [2-(2-dimethylaminoethyl)-succinato].[Cis-diamine]platinum (II);
Compound 3: [2-(3-dimethylamino propyl)-succinato].[Cis-diamine]platinum (II);
Compound 4: [2-(3-amino propyl)-succinato].[Cis-diamine] platinum (II);
Compound 5: [2-(2-diethylaminoethyl)-succinato].[Cis-diamine]platinum (II);
Compound 6: [2-(3-di-n-propylamino propyl)-succinato].[Cis-diamine]platinum (II);
Compound 7: [2-(3-(1-piperidyl)-propyl)-succinato].[Cis-diamine]platinum (II);

Compound 8: [2-(3-(1-pyrrolidyl)-propyl)-succinato].[Cis-diamine]platinum (II)

Compound 9: [2-(2-aminoethyl)-succinato].[Cis-(1,2-trans-cyclohexyldiamine)]platinum (II);

Compound 10: [2-(2-diethyl amino ethyl)-succinato].[Cis-(1,2-trans-cyclohexyl diamine)]platinum (II);

Compound 11: [2-(3-dimethylamino propyl)-succinato].[Cis-(1,2-trans-cyclohexyl diamine)]platinum (II);

Compound 12: [2-(2-ethylamino ethyl)-succinato].[Cis-(1,2-trans-cyclohexyl diamine)]platinum (II);

Compound 13: [2-(3-(1-piperidyl) propyl)-succinato].[Cis-(1,2-trans-cyclohexyl diamine)]platinum (II);

Compound 14: [2-(3-di-n-propylamino propyl)-succinato].[Cis-(1,2-trans-cyclohexyl diamine)]platinum (II);

Compound 15: [2-(3-diethylamino propyl)-succinato].[Cis-(1,2-trans-cyclopentyl diamine)]platinum (II);

Compound 16: [2-(3-diethylamino propyl)-succinato].[Cis-(1,2-trans-cyclobutyl diamine)]platinum (II);

Compound 17: [2-(3-diethylamino propyl)-succinato].[Cis-(1,2-trans-cyclopropyl diamine)]platinum (II);

Compound 18: [2-(2-dimethylaminoethyl)-succinato].[Cis-1,2-ethyldiamine]platinum (II);

Compound 19: [2-(2-diethylaminoethyl)-succinato].[Cis-1,3-propyl diamine]platinum (II);

Compound 20: [2-(3-di-n-propylaminopropyl)-succinato].[Cis-1,4-butyldiamine]platinum (II);

Compound 21: [2-(2-diethyl amino ethyl)-succinato].[Cis-1,2-(1,2-dihydroxy methyl)-ethyldiamine]platinum (II);

Compound 22: [2-(2-dimethyl amino ethyl)-succinato].[Cis-1,3-(2,2-dihydroxyt methyl)-propyl diamine]platinum (II);

Compound 23: [2-(2-dimethylaminoethyl)-succinato].[Cis-1,4-(trans-2,3-cyclobutyl)-butyldiamine]platinum (II);

Compound 24: [2-(2-diethylamino ethyl)-succinato].[Cis-1,4-(trans-2,3-cyclobutyl)-butanediamine]platinum (II);

Compound 25: [2-(2-diethylaminoethyl)-succinato].[Cis-1,4-cyclohexyldiamine]platinum (II);

Compound 26: [2-(2-diethylaminoethyl)-succinato].[Cis-1,3-(2,2-(4-oxacyclohexyl))-propyl diamine]platinum (II);

Compound 27: [2-(4-diethylamino butyl)-succinato].[Cis-diamine]platinum (II) acetate;

Compound 28: [2-(4-diethylamino butyl)-succinato].[Cis-1,2-ethylenediamine]platinum (II) toluenesulfonate;

Compound 29: [2-(4-diethylamino butyl)-succinato].[Cis-(1,2-trans-cyclohexyl diamine)]platinum (II) phosphate.

The following words and phrases are the definitions of various terms used for describing the present invention. Unless limited in special case, the following terms are applicable to the entire description and claims (independently or as a part of larger group).

The term "alkyl" refers to straight chain or branched saturated univalent alkyl; specifically, alkyl is the straight chain saturated univalent alkyl having 1-20($C_{1-20}$), 1-15($C_{1-15}$), 1-10 ($C_{1-10}$), 1-7($C_{1-7}$), or 1-4 ($C_{1-4}$) carbon atoms; or the branched saturated univalent alkyl having 3-20($C_{3-20}$), 3-15 ($C_{3-15}$), 3-10 ($C_{3-10}$), 3-7($C_{3-7}$), or 3-4 ($C_{3-4}$) carbon atoms. The examples of alkyl include but not limited to methyl, ethyl, n-propyl, isopropyl, normal-butyl, isobutyl, sec-butyl, tertiary butyl, amyl (including all isomer forms), hexyl (including all isomer forms), heptyl (including all isomer forms), octyl (including all isomer forms), nonyl (including all isomer forms), decyl (including all isomer forms), hendecyl (including all isomer forms), dodecyl (including all isomer forms), tridecyl (including all isomer forms), myristyl (including all isomer forms), pentadecyle (including all isomer forms), cetyl (including all isomer forms), hetadecyl (including all isomer forms), octadecyl (including all isomer forms), nonadecyl (including all isomer forms), and eicosyl (including all isomer forms). For example, $C_{1-7}$ alkyl refers to the straight chain saturated univalent alkyl having 1-7 carbon atoms or the branched saturated univalent alkyl having 3-7 carbon atoms.

"Alkyl" may be optionally substituted by 1, 2, 3 or 4 of the following substituent groups: such as halogen, trifluoromethyl, trifluoromethoxyl, hydroxyl, alkoxy, cycloalkyloxy, heterocyclic oxygroup, oxo, alkane acyl, aryloxy, alkane acyl oxygen radical, amino, alkylamino, arylamine, aralkyl amido, naphthene amido, heterocyclic amido, substituent tertiary amine (wherein 2 nitrogen substituent groups are selected from alkyl, aryl or aralkyl); alkane acyl amido, aroyl amino, aryl alkane acyl amido, substituent alkane acyl amido, substituent aromatic amino, substituent aryl alkane acyl, thiodiglycolic, alkyl sulfonium, aryl sulfonium, aralkyl sulfonium, naphthenic sulfonium, heterocyclic sulfonium, alkyl carbonyl sulfur, aryl carbonyl sulfur, aromatic alkyl carbonyl sulfur, alkyl sulfonyl, aryl sulfonyl, aromatic alkyl sulfonyl, sulfonamido, such as $SO_2NH_2$, substituted sulfonamide, nitryl, cyano, carboxyl, carbamyl, such as $CONH_2$, substituted carbamyl such as CONH alkyl, CONH aryl, CONH aralkyl or when two substituent groups exist on nitrogen, selected from alkyl, aryl or aralkyl; alkoxy carbonyl, aryl, substituent aryl, guanidyl and heterocyclic radical, such as indolyl, imidazolyl, furyl, thienyl, thiazolyl, pyrrolidyl, pyridyl, pyrimidyl, etc. The above substituted groups may be further substituted by halogen, alkyl, alkoxy, aryl or aralkyl.

The term "alkoxy" refers to the straight chain saturated univalent alkyl having 1-20($C_{1-20}$), 1-15($C_{1-15}$), 1-10 ($C_{1-10}$), 1-7($C_{1-7}$), or 1-4 ($C_{1-4}$) carbon atoms or the branched saturated univalent alkyl having 3-20($C_{3-20}$), 3-15($C_{3-15}$), 3-10 ($C_{3-10}$), 3-7($C_{3-7}$), or 3-4 ($C_{3-4}$) carbon atoms. The examples of alkoxy include but not limited to methoxy, ethoxy, propoxy, isoproproxy, normal-butoxy, isobutoxy, sec-butoxy, tertiary butoxy, amoxy (including all isomer forms), hexoxy (including all isomer forms), heptoxy (including all isomer forms), octoxy (including all isomer forms), nonoxy (including all isomer forms), decyloxy (including all isomer forms), hendecyloxy (including all isomer forms), dodecyloxy (including all isomer forms), tridecyloxy (including all isomer forms), tetradecyloxy (including all isomer forms), pentadecyloxy (including all isomer forms), hexadecyloxy (including all isomer forms), hetadecyloxy (including all isomer forms), octadecyloxy (including all isomer forms), nonadecyloxy (including all isomer forms), and eicosyloxy (including all isomer forms). The term "alkylamine" refers to the group wherein 1 or 2 Hs in —$NH_2$ is substituted by the straight chain alkyl having 1-10($C_{1-10}$), 1-6($C_{1-6}$) or 1-4($C_{1-4}$) carbon atoms or the branched alkyl having 3-10($C_{3-10}$), 3-6($C_{3-6}$) or 3-4 ($C_{3-4}$) carbon atoms; when 2 Hs above are substituted, the substituent groups may be the same or different. Examples of alkylamine include but not limited to methylamino, dimethylamino, ethylamine, eidthylin, propylamine, dipropylamine, isopropamide, diisopropylamine, n-butylamine, isobutylamino, tert-butylamine, di-n-butylamine, diisobutylamine, di-tert-butylamine, amylamine, di-amylamine, hexanediamine, di-hexanediamine, heptylamine, di-heptylamine, octylamine, di-octylamine, nonylamine, di-nonylamine, decylamine, di-decylamine, N-methyl-N-ethylamine, N-methyl-N-propylamino, N-methyl-N-isopropylamino, N-methyl-N-butylamine, N-methyl-N-isobutylamine, N-methyl-N-tert-butylamine, N-methyl-N-amylamine, N-methyl-N-hexylamine, N-methyl-N-heptylamine, N-methyl-N-octylamine, N-methyl-N-heptyl amine, N-methyl-N-octylamine, N-methyl-N-nonyl amine, N-methyl-N-decyl amine, N-ethyl-N-propylamine, N-ethyl-N-isopropylamine, N-ethyl-N-butylamine, N-ethyl-N-isobutylamine, N-ethyl-N-tert-butylamine, N-ethyl-N-amylamine, N-ethyl-N-hexylamine, N-ethyl-N-heptylamine, N-ethyl-N-octylamine, N-ethyl-N-nonyl amine, N-ethyl-N-decylamine, N-propyl-N-isopropylamine, N-propyl-N-butylamine, N-propyl-N-isobutylamine, N-propyl-N-tert-butylamine, N-propyl-N-amylamine, N-propyl-N-hexylamine, N-propyl-N-heptylamine, N-propyl-N-octylamine, N-propyl-N-nonyl amine, N-propyl-N-decyl amine, N-isopropyl-N-butylamine, N-isopropyl-N-isobutylamine, N-isopropyl-N-tert-butylamine, N-isopropyl-N-amylamine, N-isopropyl-N-hexylamine, N-isopropyl-N-heptylamine, N-isopropyl-N-octylamine, N-isopropyl-N-nonyl amine, N-isopropyl-N-decylamine, N-butyl-N-isobutylamine, N-butyl-N-tert-butylamine, N-butyl-N-amylamine, N-butyl-N-hexylamine, N-butyl-N-heptylamine, N-butyl-N-octylamine, N-butyl-N-nonyl amine, N-butyl-N-decylamine, N-isobutyl-N-tert-butylamine, N-isobutyl-N-amylamine, N-isobutyl-N-hexylamine, N-isobutyl-N-heptylamine, N-isobutyl-N-octylamine, N-isobutyl-N-nonyl amine, N-isobutyl-N-decylamine, N-tertiary butyl-N-amylamine, N-tertiary butyl-N-hexylamine, N-tertiary butyl-N-heptylamine, N-tertiary butyl-N-octylamine, N-tertiary butyl-N-nonyl amine, N-tertiary butyl-N-decylamine, N-amyl-N-hexylamine, N-amyl-N-heptylamine, N-amyl-N-octylamine, N-amyl-N-nonyl amine, N-amyl-N-decylamine, N-decoyl-N-heptylamine, N-decoyl-N-octylamine, N-decoyl-N-nonyl amine, N-decoyl-N-decylamine, N-heptyl-N-octylamine, N-heptyl-N-nonyl amine, N-heptyl-N-decylamine, N-octyl-N-nonyl amine, N-octyl-N-decylamine, N-nonyl-N-decylamine, and all isomer forms of above amine groups.

The term "halogen" or "halogenate" refers to fluorine, chlorine, bromine, and iodine.

The term "aryl" refers to monocyclic or dicyclic aromatics containing 6-12 carbon atoms in ring, such as phenyl, naphthyl, biphenyl and diphenyl. Each "aryl" above may be substituted.

"Aryl" may be optionally substituted by the following substituent groups: Such as alkyl, halogen, trifluoromethoxy, trifluoromethyl, hydroxyl, alkoxy, cycloalkyloxy, heterocyclic oxygroup, alkane acyl, alkane acyl oxygen radical, amino, alkylamino, aralkyl amido, naphthene amido, heterocyclic amido, dialkyl amino, alkane acyl amido, thiol, alkyl sulfo, naphthenic base sulfo, heterocycle sulfo, carbamido, nitryl, cyano, carboxyl, carboxyl alkyl, formamyl, alkoxy carbonyl, alkyl carbonyl sulfur, aryl carbonyl sulfur, alkyl sulfonyl, sulfonamido, aryloxy, etc. The said substituent group may be further substituted by halogen, hydroxyl, alkyl, alkoxy, aryl, substituent aryl, substituent alkyl or substituent aralkyl.

The term "aralkyl" refers to the aryl combined directly through alkyl group, such as benzyl, phenethyl and phenylpropyl.

The term "alkenyl" refers to the straight chain or branched-chain alkyl group with 1, 2, 3 or 4 double bonds containing 2-20 carbon atoms, preferably 2-15 carbon atoms, most preferably 2-8 carbon atoms, including but not limited to vinyl, N-allylnormetazocine, isopropenyl, n-butyl-2-vinyl, n-hexyl-3-vinyl. The term "vinyl" also includes the groups having "Cis-" and "trans-" configurations, or "E" and "Z" configurations; which are understandable for the technical personnel in this field.

"Alkenyl" may be substituted by the following substituent groups: such as halogen, hydroxyl, alkoxy, alkane acyl, alkane acyl oxygen radical, amino, alkylamino, dialkyl amino, alkanoyl amido, thiodiglycolic, alkyl sulfo, alkyl carbonyl sulfur, alkyl sulfonyl, sulfonamido, nitryl, cyano, carboxyl, formamyl, substituted formamyl, guanidyl and heterocyclic radical, such as indolyl, imidazolyl, furyl, thienyl, thiazolyl, pyrrolidyl, pyridyl, pyrimidyl, etc.

The term "alkynyl or chained alkynyl" refers to the straight chain or branched-chain alkyl groups with 1, 2, 3, or 4 triple bonds containing 2-20 carbon atoms, preferably 2-15 carbon atoms, most preferably 2-8 carbon atoms.

"Alkenyl" may be optionally substituted by the following substituent groups: halogen, hydroxyl, alkoxy, alkane acyl, alkane acyl oxygen radical, amino, alkylamino, dialkyl amino, alkane acyl amido, thiodiglycolic, alkyl sulfo, alkyl carbonyl sulfur, alkyl sulfonyl, sulfonamido, nitryl, cyano, carboxyl, formamyl, substituted formyl amino, guanidyl and heterocyclic radical, such as imidazolyl, furyl, thienyl, thiazolyl, pyrrolidyl, pyridyl, pyrimidyl, etc.

The term "naphthenic base" refers to optionally substitutive, saturated hydrocarbon ring system containing 1-3 rings wherein each (may be further condensed with unsaturated $C_3$-$C_7$ carbonatomic ring) contains 3-7 carbon atoms. Example groups include cyclopropyl, cyclobutyl, cyclopentyl, cyclohexyl, cycloheptyl, cyclo-octyl, cyclodecyl, cyclic dodecyl and adamantyl. Example of substituent groups include one or more of alkyl groups as described above, or one or more of alkyl substituent groups as described above.

The terms "heterocycle", "heterocyclic", and "heterocyclic radical" refer to optionally substituted, completely saturated or incompletely saturated aromatic or non-aromatic ring group. For example, the said ring is 4-7-membered monocyclic, 7-11-membered dicyclic or 10-15-membered tricyclic system, containing at least one heteroatom on the ring at least containing one carbon atom. There may be 1, 2, 3 or 4 heteroatoms selected from nitrogen atom, oxygen atom and sulphur atom on each ring of heterocyclic group containing heteroatom, wherein the said nitrogen and sulphur heteroatom may also be optionally oxidized and nitrogen heteroatom may also be optionally quaternized. The said heterocyclic group may be connected on any heteroatom or carbon atom.

Example monocyclic heterocyclic groups include pyrrolidyl, pyrryl, indolyl, pyrazolyl, oxa-cyclobutyl group, pyrazolinyl, imidazolyl, imidazolinyl, imidazolidinyl, oxazolyl, oxazolidinyl, isoxazolinyl, isoxazolyl, thiazolyl, thiadiazole, oxazolidinyl, isoxazolinyl, isoxazolyl, furyl, tetrahydrofuran, thienyl, oxadiazol, piperidyl, piperazinyl, 2-oxo-piperazinyl, 2-oxo-piperidyl, 2-oxo-pyrrolidyl, 2-oxopazepine, azepine, 4-piperidone, pyridyl, N-oxo-pyridyl, pyrazinyl, pyrimidyl, pyridazinyl, tetrahydrothiopyran, tetrahydropyrane, morpholinyl, thiamethoxam morpholinyl, thiamethoxam morpholine sulfoxide, tetrahydrothiopyran sulfoxide, thiamethoxam morpholinyl sulfoxide, 1,3-dioxolame and tetralin-1,1-dioxo thienyl, dioxane, isoxazolyl, thia cyclobutyl, thia cyclopropyl, triazinyl and triazolyl, etc.

Example bicyclic heterocyclic groups include benzothiazolyl, benzoxazolyl, benzothiophene, quinuclidinyl, quinolyl, quinolyl-N-oxide, tetrahydroisoquinol, isoquinolyl, benzimidazolyl, benzopyranyl, indolizine, benzopyranyl, chromone, aryl coumarin, 1,2-phthalazine, quinoxaline, indazolyl, pyrrolo and pyridyl, furan and pyridyl (such as furan and [2,3-c]pyridyl, furan and [3, 1-b]pyridyl or furan and [2,3-b]pyridyl), isoindolinyl, dihydrogen quinazoline (such as 3, 4-dihydro-4-oxo-quinazolinyl), benzisothiazol, benzisoxazole, benzodiazine, benzopyranyl, benzothiopyran, benzodiazine, benzofuryl, thiochroman, thiochroman sulphone, chroman, chroman sulphone, dihydrobenzene benzopyranyl, indolinyl, isobenzopyran, isoindolinyl, 1,5-phthalazine, 2, 3-phthalazine, 3,4-methylenedioxy benzyl, purine, pyridine-pyridy, quinazolinyl, tetralinquinolyl, thiophene-furan, thiophene-pyridine, thiophene-thienyl, etc.

Smaller heterocycles, such as epoxide and aziridine, are also included.

The term heteroatom includes oxygen, sulphur and nitrogen.

The term pharmaceutically acceptable salt includes the active compound salts prepared with relatively nontoxic acid or alkali on the basis of the specific substituent group existed on the compounds as described in the present invention. When the compound in the invention contains relatively acidic functional group, alkali addition salt can be obtained by enabling the compound in neutral form to contact sufficient necessary alkali directly or in appropriate inert solvent. Examples of pharmaceutical acceptable inorganic alkali salt derivatives include aluminum, ammonium, calcium, copper, ferric iron, ferrous, lithium, magnesium, manganese, bivalent manganese, potassium, sodium, zinc, etc. Pharmaceutical acceptable organic base salt derivatives include primary, secondary and tertiary amine salts; they include substituent amine, cyclammonium, amine, etc., such as arginine, glycine betaine, caffeine, choline, N,N'-dibenzyl ethylenediamine, diethylamine, 2-diethyl aminoacyl alcohol, 2-dimethyl aminoacyl alcohol, cholamine, ethylenediamine, N-ethyl morpholine, N-ethyl piperidine, glucosamine, glucamine, histidine, hydrabamine, isopropamide, lysine, methylglucosamine, morpholine, piperazine, piperidine, polyamino resin, procaine, purine, theobromine, triethylamine, trimethylamine, tripropylamine, tromethamine, etc. When the compound of the present invention contains relatively alkali functional group, acid addition salt can be obtained by enabling the compound in neutral form to contact sufficient required acid directly or in appropriate inert solvent. Examples of pharmaceutical acceptable acid addition salts include salts derived from inorganic acid, such as nitrate, carbonate, bicarbonate, phosphate, hydrophosphate, dihydric phosphate, sulphate, bisulfate, phosphite, hydrochloride, hydrobromide, hydriodate, etc.; salt derived from relative nontoxic organic acid, for example, acetic acid, propionic acid, isobutyric acid, malonic, benzoic acid, succinato, suberic acid, fumaric acid, mandelic acid, phthalic acid, benzenesulfonic acid, p-toluenesulfonic acid, citric acid, tartaric acid, methanesulfonic acid, etc.; and also include arginine acid, for example, arginine salt and organic acid such as glucuronic acid or galactonic acid salts; preferably nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactose acid salt.

In some embodiments in the present invention, the leaving group of compounds in the present invention contains basic group(s) that may form salt with acid and platinum (II) complex salts are prepared with the method well known to the technical person in this field. For example, it may form mesylate, trifluoromethanesulfonic salt with lower alkyl sulfonic acid, such as methanesulfonic acid, trifluoromethanesulfonic acid, etc.; form tosilate, benzene sulfonate, camphosulfonate with arylsulphonate, such as benzenesulfonic acid or p-toluenesulfonic acid, etc; form appropriate salts with organic carboxylic acid, such as acetic acid, fumaric acid, tartaric acid, oxalate, maleic acid, malic acid, succinato, lactic acid or citric acid, etc.; may form glutamate or aspartate with arginine acid, such as glutamic acid or aspartic acid; form appropriate salts with inorganic acid, such as nitric acid, carbonic acid, sulfuric acid or phosphoric acid, etc. The acid that may be used include organic acid, inorganic acid, etc.

The compounds of the present invention may be interconverted with their salt forms through the conventional method in this field. For example, free bases can be obtained by separation in conventional way after making salts contact alkali or acid, or the form of salts can be obtained by separation in conventional way by adding acid or alkali to the compounds. Some physical properties of the free bases, such as the solubility in polar solvent, are different from various salt forms; however, for the purpose of the present invention, salts and the compounds in parent form have the same antitumor effect.

In addition to the salt form, the present invention may provide the compounds in the form of precursor esters. The "precursor(s)" of the compounds as described in the present invention refer(s) to the compounds that are prone to chemical change in physiological environment to obtain the compounds of the present invention. In addition, precursors can be converted into the compounds of the present invention with chemical or biochemical methods in separation environment. For example, when placed in the transdermal patch repository containing appropriate enzyme or chemical reagent, precursors may be slowly converted into the compounds of the present invention. Precursors are usually pharmacological inert compounds before converting into active drugs; however, this situation is not necessary. Usually, the functional group required by the activity in drug is concealed with "precursor group" (as defined below), releasing functional group through conversion (such as cracking in specific operating condition) and obtaining the "precursor part" of active drug and precursor. Precursor part may be catalyzed or induced through such as hydrolysis reaction, or through another actor (such as enzyme, light, acid or alkali) or change of physical or environmental parameter (such as change of temperature) or exposing physical or environmental parameters for spontaneous cracking. Comparing with operating environment, actor may be endogenic, for example, the enzyme existed in the cell where precursor is given or the acidic environment of gastro or provided from external source.

"Precursor Group" refers to a sort of protective group that can convert drug into precursor when the functional group used in covering active drug forms "precursor part". Precursor group is usually connected with the functional group of drug through bond. The said bond can be cracked in specific condition. Therefore, precursor group is a part of precursor. The said part of precursor is cracked in specific operating condition and releases functional group. As a specific example, the amide precursor part of the formula —NH—C(O)CH$_3$ contains precursor group —C(O)CH$_3$.

It is well known in the art that a wide variety of precursor groups and the part of precursors suitably conceal the functional group in active compounds to obtain precursors. For example, hydroxyl functional group may become sulphonate, ester (such as acetic acid ester or maleic acid ester) or carbonic acid ester precursor part by concealing. This precursor part may be hydrolyzed in the body, to obtain hydroxyl. Carboxyl can be covered into ester (including methyl, ethyl, pivaloyl acyloxy methyl, silicyl ester and sulpho acid ester), amide or hydrazide precursor part. They can be hydrolyzed in body to obtain carboxyl. The present invention includes the known esters and acyls used for change of solubility or hydrolysis property in the field, used as controlled-release or precursor preparation. For one skilled in the art, the specific examples of appropriate precursor groups and their appropriate precursor parts are obvious.

Some compounds of the present invention may exist in the form of non-solvation and solvation including hydration.

"Solvate" refers to the compound generated from the combination of solvent molecule with the molecule or ion of solute. Solvent may be organic compound, inorganic compound or the mixture of both. Some examples of solvent include but not limited to carbinol, N, N-dimethyl formamide, tetrahydrofuran, dimethylsulfoxide, and water. Generally, solvent form is equivalent to non-solvent form and included in the range of the present invention. Some compounds of the present invention may exist in the form of polymorph or amorphism. In general, for the assumed usage of the present invention, all physical forms are the same and included in the range of the present invention.

Some compounds of the present invention have asymmetric carbon atom (rotophore) or double bonds; their raceme, non-enantiomer, geometric isomer, regional isomer and individual isomer (such as separated enantiomer) are included in the range of the present invention. Those isomers may be split or asymmetrically synthesized with conventional method to make isomer "optical pure", i.e., not containing other isomers on the whole. For example, if particular enantiomer of the compound of the present invention is required, pure required enantiomer can be obtained through asymmetric synthesis preparation or through chiral auxiliaries derivatization, wherein splitting the mixture of diastereomer obtained and cracking the assistant group, or when the molecule contains alkali functional group such as amino or acidic functional group such as carboxyl, appropriate optical active acid or alkali may be used for forming asymmetric heterogeneous salt, then splitting the non-enantiomer formed hereof through fractional crystallization or chromatographic process well-known in this field, finally pure enantiomer is recovered.

The compound of the present invention may contain the isotope of the atom in abnormal proportion in one or more atoms constituting the compound. For example, the compound may be labeled with radioisotope such as tritium ($^3H$), iodine-125($^{125}I$) or carbon-14($^{14}C$). Regardless of whether it has radioactivity or not, all isotope forms of the compounds of the present invention are all included in the range of the present invention.

Another purpose of the present invention is to provide the preparation methods for the foregoing compounds.

I. The preparation method for the formula (A) is provided as follows:
(1) adding potassium chloroplatinite into water and stirring the mixture to form solution at room temperature; after dissloving potassium iodide in water, putting it into above potassium chloroplatinite solution to react under nitrogen away from light and oxygen in water bath condition;
(2) dissolving $R_4NH_2$ in water, which is then added dropwise into the reaction liquid in step (1), and reacting the mixture in water bath condition;
(3) after cooling down above reaction mixture below room temperature, dissolving $R_5NH_2$ in water, which is then added dropwise into the reaction mixture in step (2) to react in water bath; generating yellow deposit in large quantity in the mixture; after cooling down the mixture below room temperature; obtaining diiodo diamine platinum (II) through suction filtration and washing;
(4) adding $Ag_2SO_4$ into water and stirring it; then adding the above diiodo diamine platinum (II) into reaction liquid of $Ag_2SO_4$ aqueous solution, after adding water into it to obtain a mixture, reacting the mixture in water bath condition away from light and oxygen under nitrogen, and obtaining dihydrol diamine platinum (II).sulphate by suction filtration;
(5) putting diethyl succinate, $Br—R_3—Br$, $K_2CO_3$ and tetrabutylammonium bromide into flask and stirring it to obtain a mixture, heating the mixture for reaction; after removal of solid by suction filtration, washing the solid and combining the filtrate, then washing the organic phase and drying it, collecting the distillate after removal of solvent by reduced pressure distillation;
(6) putting 2-Br—$R_3$-diethyl succinate, anhydrous $K_2CO_3$ and acetonitrile into a flake and stirring to obtain a reaction mixture; adding $R_1$—NH—$R_2$ into the reaction mixture, and proceeding a reaction under heating; filtering out a insoluble substance of the mixture; pumping dry the filtrate and dissolving the residue in organic solvent; washing the organic phase with aqueous solution and drying it; after removal of solvent under reduced pressure; obtaining the product and purifying it;
(7) adding NaOH solution into the product in step (6) and stirring it at room temperature;
(8) after adjusting the pH of the product in step (7) with acid solution, adding the product in above step (4) into it, then heating the mixture for reaction to afford the platinum compound of the present invention.

The Preferable preparation method is as follows:
(1) Stirring potassium chloroplatinite in water at room temperature; potassium iodide solution of water was added into above potassium chloroplatinite solution. The mixture was stirred away from light and oxygen in water bath at 40~60° C.
(2) $R_4NH_2$ solution of water was added dropwise to the reaction mixture in (1) to react in water bath at 40~60° C.;
(3) Cooling down reaction mixture below 20° C., $R_5NH_2$ aqueous solution was added dropwise into the reaction mixture in (2) to react in water bath for 30~60 min at 40~60° C.; there will be yellow deposit in great quantity; after cooling down below 20° C., diiodo diamine platinum (II) was obtained by suction and washing with water, anhydrous ethanol, and diethyl ether in turn.
(4) Stirring $Ag_2SO_4$ in water, above diiodo diamine platinum (II) was put into reaction mixture and then water was added; the mixture was stirred away from light and oxygen at 40~60° C.; dehydratediamine platinum (II).sulphate was obtained after suction filtration.
(5) Putting diethyl succinate, $Br—R_3—Br$, $K_2CO_3$ and tetrabutylammonium bromide into flask the mixture was heated and stirred; after removal of solid by suction and washing, filtrate was washed and dried over $MgSO_4$; distillate was collected in vacuo after removal of solvent;
(6) Stirring 2-Br—$R_3$-diethyl succinate and anhydrous $K_2CO_3$ in acetonitrile; $R_1$—NH—$R_2$ was added into reaction mixture; the mixture was heated and stirred; filtering out insoluble substance of the mixture; the filtrate was pumped dry and added, organic solvent for dissolution; the organic phase was washed with aqueous solution and dried; after removal of solvent in vacuo, the product was obtained by purification.
(7) NaOH solution was added into the product in (6) and stirred at room temperature.
(8) After treating the product in (7) with acid solution, the product in above (4) was added, the mixture was heated to afford the platinum compound of the present invention.

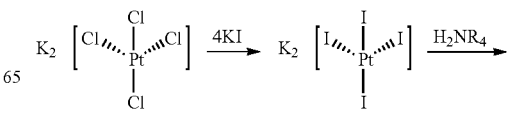

-continued

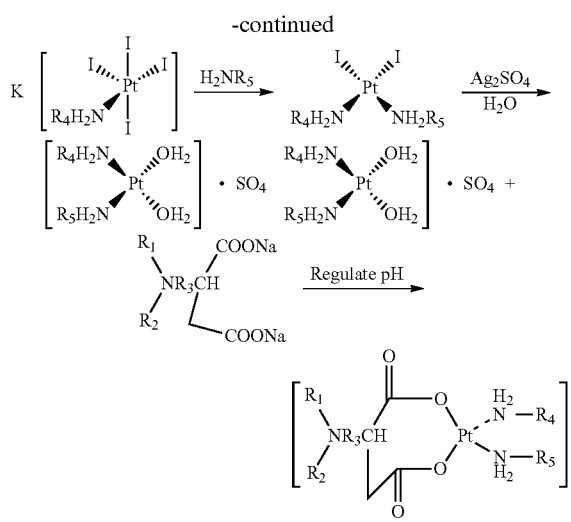

II. The preparation method in the formula (C) is as follows:

(1) adding potassium chloroplatinite into water and stirring it at room temperature; then adding potassium iodide solution of water into above potassium chloroplatinite solution, and proceeding a reaction under nitrogen away from light and oxygen in water bath;

(2) adding bidentate ammonia $NH_2$—X—$NH_2$ aqueous solution dropwise into the reaction mixture in step (1) to react in water bath, and affording yellow deposit in great quantity; after cooling down the mixture below room temperature, obtaining bidentatediiodo diamine platinum (II) by suction filtration and washing;

(3) adding $Ag_2SO_4$ into water and stirring it to obtain a reaction mixture, then putting above bidentatediiodo diamine platinum (II) into the reaction mixture and then adding water into it; after making the obtained mixture to react under nitrogen away from light and oxygen in a water bath, obtaining dihydrol diamine platinum (II).sulphate after suction filtration;

(4) putting diethyl succinate, Br—$R_3$—Br, $K_2CO_3$ and tetrabutylammonium bromide into a flask and stirring it to obtain a mixture, heating the mixture for reaction; after removing the solid by suction filtration and washing it, combining the filtrates, washing the organic phase and drying it, then collecting the distillate after removal of solvent by reduced pressure distillation;

(5) stirring the mixture of 2-Br—$R_3$-diethyl succinate, anhydrous $K_2CO_3$ and acetonitrile to provide a reaction mixture; then adding $R_1$—NH—$R_2$ into the reaction mixture and reacting the mixture under heating; filtering out insoluble substance of the mixture; after pumping dry the filtrate, adding organic solvent for dissolution; washing the organic phase with aqueous solution and drying it; after removal of solvent under reduced pressure, obtaining the product and purifying it;

(6) adding NaOH solution into the product in step (5) and stirring it at room temperature;

(7) after treating the product in step (6) with acid solution, adding the product in above step (3) into it, and heating the mixture for reaction to afford the platinum compound of the present invention.

The Preferred preparation method is as follows:

(1) Potassium chloroplatinite was added in water and stirred at room temperature; potassium iodide solution of water was added into above potassium chloroplatinite solution. The mixture was stirred away from light and oxygen in water bath at 40~60° C. for 30-60 minutes.

(2) Bidentate diamine $NH_2$—X—$NH_2$ aqueous solution was added dropwise into the reaction mixture in (1) to react in water bath for 40~60° C. for 30-60 minutes; yellow deposit in great quantity was afforded; after cooling down the mixture below 20° C., bidentatediamine diiodo platinum (II) was obtained by suction and washing with water, absolute ethyl alcohol, and diethyl ether.

(3) Stirring $Ag_2SO_4$ in water, above bidentate diamine diiodoplatinum (II) was put into reaction mixture and then water was added; the mixture was stirred away from light and oxygen at 40~60° C. for 4-8 h; dihydratediamine platinum (II).sulphate was obtained after suction filtration.

(4) Putting diethyl succinate, Br—$R_3$—Br, $K_2CO_3$ and tetrabutylammonium bromide into flask, the mixture was heated and stirred; after removal of solid by suction and washing, filtrate was washed and dried over $MgSO_4$; distillate was collected in vacuo after removal of solvent;

(5) Stirring 2-Br—$R_3$-diethyl succinate and anhydrous $K_2CO_3$ in acetonitrile; $R_1$—NH—$R_2$ was added into reaction mixture; the mixture was heated and stirred; filtering out insoluble substance of the mixture; the filtrate was pumped dry and added organic solvent for dissolution; the organic phase was washed with aqueous solution and dried, after removal of solvent in vacuo; the product was obtained by purification;

(6) NaOH solution was added into the product in (5) and stirred at room temperature;

(7) After treating the product in (6) with acid solution, the product in above (3) was added, the mixture was heated to afford the platinum compound of the present invention.

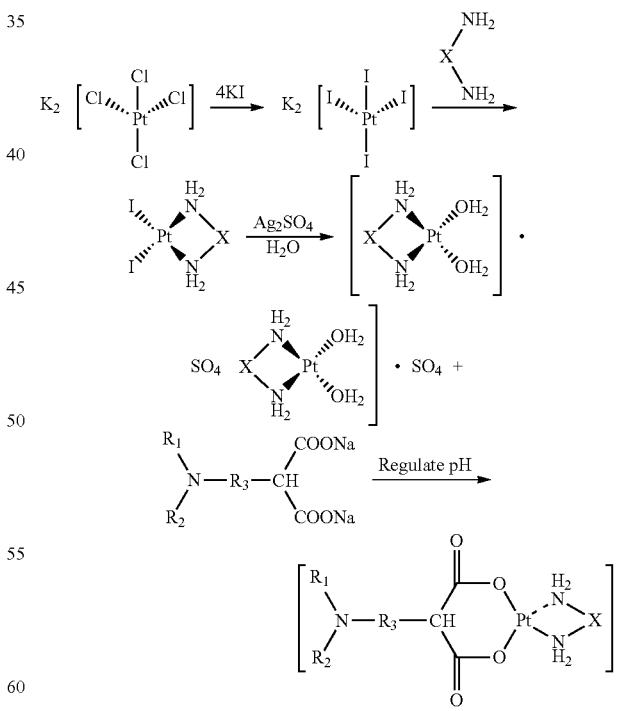

The present invention also provides a pharmaceutical composition containing above compound(s), its pharmaceutically acceptable salt, stereoisomer, precursor or its solvate and pharmaceutical acceptable carriers. The composition contains approximately 0.01%-100%, preferably approximately 0.1%400%, more preferably approximately 1%-100%, most preferably approximately 20%-100% (in weight) of one or more compounds of the present invention. The remaining part is composed of appropriate drug carrier(s) and/or excipient(s). The known method in this field and appropriate carrier may be used to form composites containing the compounds of the present invention to match with administration route.

The quantity of the active compound in unit dose preparation may be between approximately 0.001 mg and approximately 1000 mg, preferably between approximately 0.01 mg and approximately 500 mg, and more preferably between approximately 1 mg and approximately 100 mg, and most preferably between approximately 10 mg and approximately 50 mg.

The administration may, for example, be oral, local, intravenous, subcutaneous, percutaneous, transdermal, intramuscular, intra-articular, parenteral, intra-arterial, intradermal, intraventricular, encephalic, intraperitoneal, within damage, intranasal, rectum, vagina, suction or through implantation repository. The term "parenteral" used in present invention includes subcutaneous, intravenous, intramuscular, intra-articular, within synovial fluid, within breast bone, intrathecal, intrahepatic, within damaged position and intracranial injection or target controlled infusion, preferably giving composites intravenously. The preparation of the present invention may be designed as quick-acting, immediate-release or long-acting. In addition, the compound may be administered locally other than in systemic way, such as giving (such as injecting) sustained release preparation. In accordance with the representative embodiment, the composites of the present invention may be prepared into the drug for mammal, preferably for human.

One or more composites containing in the present invention may be given repeatedly, for example, at least 2, 3, 4, 5, 6, 7, 8 or more times, or the composites may be given through continuous infusion. The appropriate positions of drug delivery include but not limited to blood vessel, muscle, skin, bronchus, intestines and stomach, anus, vagina, eye and ear. The preparation may adopt liquid dosage form, freeze-dry powder form, solid or semisolid, such as solution, suspension, emulsion, tablet, pill, capsule, powder, suppository, retention enema, cream, ointment, lotion, gel, aerosol, etc., preferably, the simple unit dosage form for delivering accurate dose.

For parenteral drug delivery, the composite may be in the form of sterile injection and aseptic packaging powder, preferably, preparing injection at pH value of approximately 4.0-8.0.

The composite of the present invention in sterile injection form are water or oil mixed suspension. Such suspension may be prepared with suitable dispersive or wetting agent and suspending agent according to the known technology in the field. Sterile injection preparation may be the sterile injection solution or suspension dissolved or suspended in nontoxic parenteral acceptable diluent or solvent, such as the solution dissolved in 1,3-butylene-glycol. Usable acceptable menstruum and solvent include water, Ringer's solution and other hypertonic sodium chloride solution. Additionally, sterile non-volatile oil is usually used as solvent or suspended substrate. Therefore, the nonvolatile oil of any brand including synthetic monoglyceride or diester can be used, similar to naturally pharmaceutical acceptable oil such as olive oil or castor oil, especially their polyethylene oxide ethylation form. Fatty acid such as oleic acid and its glyceride derivant can be used to prepare injection preparation. Such oil solution or suspension may also contain long-chain alcohol diluent or dispersing agent, such as carboxymethylcellulose or similar dispersing agent generally used in the preparation in pharmaceutical acceptance dosage form including emulsion and suspension. Other commonly used surfactants, such as Tween, Span, and the acceptable solid, liquid usually used for preparation pharmacy or other emulsifier or bioavailability promoter in other dosage form may be used for the purpose of preparation. Such compounds as those used for parenteral drug delivery, for example, through injection such as large dose injection or continuous infusion, may be prepared. Injection unit dosage form may be stored in ampoule or multiple-dose container.

The composites of the present invention in the form of freeze-drying may be provided. Such composites may include buffer agent used for redissolution before drug delivery, or freeze-drying composites may contain buffer agent, used for, for example, water redissolution. Freeze-drying composites may contain appropriate vasoconstrictor, such as epinephrine. Freeze-drying composites may be delivered through syringe, optionally packaged with the buffer agent used for redissolution, for the convenience to immediately delivering such redissolution composites to patients.

The medicinal composites of the present invention may also be used as any oral acceptable dosage form. They include tablet, capsule, cachet, emulsion, suspension, solution, syrup, elixir, spray, pill, lozenge, powder, granule and sustained release preparation. Appropriate excipients used for oral administration include medical Mannitol, lactose, starch, magnesium stearate, saccharin sodium, talc, cellulose, glucose, gelatin, cane sugar, magnesium carbonate, etc. In case of the tablet used for oral administration, the common carriers include lactose and corn starch. Generally, lubricant such as magnesium stearate may be added. In case of capsule, usable diluents include lactose and dry corn starch. When water suspension is required for oral medication, active ingredient shall be mixed with emulsified and suspending agents. Some sweetening agents, corrigents or colorants may be added according to the circumstances.

One or more compounds of the present invention and optionally one or more pharmaceutical acceptance auxiliary materials may be dissolved or dispersed on carriers such as salt aqueous solution, glucose aqueous solution, glycerol, ethanol, etc. to form, for example, oral, local or intravenous administered solution or suspension for preparing liquid compositions. Sterile liquid, such as oil, water, ethanol and their combination may be used for preparing the pharmaceutical preparations in the form of liquid suspension or solution. For oral or parenteral drug delivery, pharmacy-suitable surfactant, suspending agent or emulsifier may be added. Suspension may contain oil, such as peanut oil, sesame oil, cottonseed oil, corn oil, and olive oil. Suspension preparation may also contain fatty acid ester, such as oleic acid ethyl ester, isopropyl myristate; fatty acid glyceride and acetyl fatty acid glyceride. Suspension preparations may include ethanol, such as alcohol, isopropanol, hexadecanol, glycerol and propylene glycol; ether such as poly (ethylene glycol); petroleum hydrocarbon, such as mineral oil and vaseline, and water can also be used for suspension preparation.

The composites may be in form of pill, tablet or capsule, so they may contain one or more diluents, such as lactose, cane sugar, dicalcium phosphate, etc; disintegrants, such as starch or their derivatives; lubricants, such as magnesium stearate, etc; and/or adhesives, such as starch, Arabic gum, polyvinylpyrrolidone, gelatin, cellulose, and their derivatives. Tablet may be prepared with any pressing or molding method known to the technical personnel in the field. Tablet may be prepared and pressed through pressing optionally the compounds of the present invention in the form of free flow mixed with auxiliary elements (such as adhesive, lubricant, diluent, disintegrant or dispersing agent) in suitable machine. Molding tablet may be prepared by molding powder mixture of the compound of the present invention with any suitable carrier in suitable machine.

Or the medicinal composites of the present invention may be in the suppository form of rectal administration. Such suppositories may be prepared by mixing the drug with appropriate non-irritating excipient, which is solid under room temperature but is liquid under rectal temperature and thus release drug in rectum. Such materials include cocoa butter, beewax, polyethylene glycol, hard fat and/or hydrogenated coco-glyceride. The composites suitable for rectal administration may also contain rectal enema unit. Such unit contains one or more compounds of the present invention and pharmaceutical acceptable menstruum (such as 50% ethanol aqueous solution or salt aqueous solution). Such menstruum is physiologically compatible with rectum and/or colon. Rectal enema unit contains the applicator tip protected by inert cover. This tip, preferably, is composed of polyethylene, lubricated with lubricant such as white vaseline, preferably protected by one-way valve, to prevent the backflow of the drug delivered. Rectal enema unit should have sufficient length, preferably 2 inches, and inserted into colon via anus.

The medicinal compositions of the present invention may also be in the form of local drug delivery, especially when therapeutical target was the region or organ locally accessible. The diseases of those organs include the diseases of eye, skin or lower intestinal tract. It is easy to prepare suitable topical preparation used for the regions or organs in those regions or organs. In case of topical administration, the compound of the present invention containing one or more composites may be in the form of emulsion, lotion, gel, foam, cream, gelatin, solution, suspension, ointment and transdermal patch.

Topical administration at lower intestinal tract can be realized through rectal suppository preparation or suitable enema preparation. Topical transdermal patch may be used as well. In case of topical application, the medicinal composites in appropriate ointment form may be prepared. Such ointment contains the active ingredient suspended on or dissolved in one or more carriers. The carriers used for the topical delivery of the compound of the present invention include but not limited to mineral oil, liquid Vaseline, white Vaseline, propylene glycol, polyoxyethylene, polypropylene oxide compound, emulsifying wax and water. Or the medicinal composites in appropriate lotion or cream form may be prepared. Such lotion or creation contains the active ingredients suspended on or dissolved in one or more pharmaceutical acceptable carriers. Suitable carriers include mineral oil, Span-60, Tween-60, cetyl, wax, cetanol, 2-octyldodecanol, benzyl alcohol and water.

The medicinal composites of the present invention may be delivered through nose aerosol or suction. In case of inhalation delivery, the composites in the form of dry powered or liquid may be delivered through sprayer. Such composites are prepared with the known technology in pharmaceutical preparation field. Moreover, the composites in the form of solution may be prepared in saline with benzyl alcohol or other suitable corrosion remover, absorption enhancer for reinforcing bioavailability, fluorocarbon compound and/or other conventional solubilizer or dispersing agent.

The pharmaceutical acceptable carriers that can be used for those composites include ion exchanger, aluminum oxide, aluminum stearate, lecithin; serum protein such as human serum albumin; buffer substance such as phosphate; glycine, sorbic acid, potassium sorbate, partial glyceride mixture of saturate plant fatty acid, water, salt or electrolyte such as sulfuric acid protamine, sodium hydrogen phosphate, potassium hydrogen phosphate, sodium chloride, zinc salt; colloidal silicon dioxide, magnesium trisilicate, polyvinylpyrrolidone, cellulose substance, polyethylene glycol, sodium carboxymethylcellulose, polyacrylate, wax, polyethylenepolypropylene oxide-block polymer, polyethylene glycol and wool fat.

Examples of suitable excipients include but not limited to water, saline, lactose, glucose, cane sugar, sorbitol, Mannitol, starch, Arabic gum, calcium phosphate, alginate, tragacanth, gelatin, calcium silicate, microcrystalline cellulose, polyvinylpyrrolidone, cellulose, syrup, methylcellulose, ethyl cellulose, hydroxypropyl methyl cellulose and polyacrylic acid, such as carbopol. The composites may include lubricant such as talcum powder, magnesium stearate and mineral oil; wetting agent; emulsifier; suspending agent; corrosion remover such as methyl-, ethyl- and propyl-hydroxyl-benzoate; pH modifier such as inorganic and organic acid and alkali; sweetening agent; and corrigent.

In addition to above representative dosage forms, the technical personnel in the field usually know other pharmaceutical acceptable excipients, carriers and dosage forms, which were included in the present invention. It is understood that the specific dosage and therapeutical schedule for any specific patient are decided by many factors. They include the activity of specific compound used, patient's age, weight, general health condition, sex, diet, drug administration time, discharge rate, combination, judgment of therapist and severity of specific disease treated. The quantity of active ingredient is also decided by specific compound and other therapeutic drug in (if any) composites.

The above pharmaceutical composites can further include other active ingredients for treating or auxiliary treating proliferating diseases, or the other combined use of the drugs for treating or auxiliary treating proliferating disease, such as the combined use of anti-proliferative agent, immunomodulator, anticancer drug, cytotoxic agent, and anticancer aided drug beyond the present invention.

Other examples of those therapeutic agents include: antiproliferative agent, such as methotrexate; FK506 (fujimycin, Prograf), mycophenolate mofetil; TNF-α inhibitor, such as Tenidap; cytotoxic drug, such as azathioprine and cyclophosphamide; anti-TNF antibody or soluble TNF receptor, such as etanercept (Enbrel); Rapamycin, Ieflunimide, and cyclo-oxygenase-2 (COX-2) inhibitor, such as celecoxib and rofecoxib, or their derivatives; and the PTK inhibitor that the existing technology has been made public.

Typical anticancer drugs and cytotoxic agents include but not limited to: alkylating agent, such as chlormethine, alkylsulphonate, nitrourea, aziridine and triazene; antimetabolite, such as Folate antagonist, purineanalogue and pyrimidine analogue; antibiotics, such as anthracene nucleus, bleomycin, mitomycin, dactinomycin and streptomyces plicatus; enzyme, such as L-asparaginase; farnesyltransferase inhibitor; hormone drug, such as, glucocorticoid, estrogen/antiestrogen, androgen/antiandrogen, pregnendione, luteinizing hormone releasing hormone antagonist, acetic acid Sandostatin; microtubules breaker, such as ecteinascidin or its analogue and derivant; microtubules stabilizer, such as paclitaxel, docetaxel and epothilone or their analogues or derivatives; products derived from plants, such as Vinca Alkaloids, epipodophyllotoxin, taxane; topoisomerase inhibitor; isoprene based protein transferase inhibitor; miscellaneous reagents, such as, hydroxycarbamide, Procarbazine, Mitotane, hexamethyl melamine, platinum coordinated complex such as cisplatin and Carboplatin; and other drugs used for anticancer and cytotoxic agent, such as biological response regulator, growth factor; and immunomodulator and monoclonal antibody. The compound of the present invention may also be used in combination with radiotherapy.

The examples of the anticancer drugs and cytotoxic agents in the same category include but not limited to: chlormethine hydrochloride, cyclophosphamide, chlorambucil, betamerphalan, ifosfamide, busulfan, carmustine, lomustine, semustine, streptozotocin, thiotepa, dacarbazine, methotrexate, sulfur guanopterin, thiol petrin, fludarabine, Pentastatin, leustatin, cytarabine, fluorouracil, doxorubicin hydrochloride, daunorubicin, idarubicin, sulfuric acid bleomycin, mitomycin C, Dactinomycin D, safracins, Micronomicin, quinocarcins, discodermolides, vincristine, vincaleukoblastinum, Corvino libin tartrate, etoposide, teniposide, paclitaxel, tamoxifen, estramustine, phosphoric acid estramustine sodium salt, Flutan, Buserelin, Lupron, pteridine, diyne, levomisole, aflacon, interferon, interleukin, Aldesleukin, Felsdine, myeloid growth factor, rituximab, BCG, vitamin A acid, irinotecan hydrochloride, betamethasone, gemcitabinehydrochloride, hexamethy and Topotecan, and any of their analogues or derivatives.

The preferred members in those categories include but not limited to: paclitaxel, cisplatin, Carboplatin, adriamycin, idarubicin, daunorubicin, aminopterin, methotrexate, methyl petrin, mitomycin C, ecteinascidin, pholipomycin, 5-fluorouracil, 6-thiol petrin, gemcitabine, cytarabine, podophyllotoxin or podophyllotoxin derivant, such as etoposide, phosphoric acidetoposide or teniposide, betamerphalan, vincaleukoblastinum, vincristine, leurosidine, vindesine and leurosine.

Examples of antitumor drugs and other cytotoxic agents include: U.S. patent application Ser. No. 09/506,481, submitted on Feb. 17, 2000, German patents 41380428, WO97/19086, WO98/22461, WO98/25929, WO98/38192, WO99/01124, WO99/02224, WO99/02514, WO99/03848, WO99/07692, WO99/27890, WO99/28324, WO99/43653, WO99/54330, WO99/54318, WO99/54319, WO99/65913, WO99/67252, WO99/67253, cytotoxic agents and their derivatives in WO00/00485; cell cycle protein dependent kinase inhibitor in WO99/24416; and isoprene protein transferase inhibitor in WO97/30992 and WO98/54966.

When other therapeutic agents above are used together with the compounds of the present invention, the doses are acted in accordance with the clinical medicine manual or determined by the general technical personnel in the field.

Finally, the present invention provides a method for treating cell proliferation diseases, including effective dosage of the compound in the formula (A) delivering to the patient with requirement.

Cell proliferation diseases refer to the diseases with the characteristic of abnormal cell proliferation. Proliferation diseases do not mean any limit on cell growth rate but only represent the loss of the normal control affecting growth and cell division. Therefore, in some embodiments, the cell of proliferation diseases may have the same cell division rate as normal cell without affecting the signal restricting such growth. Within the range of neoplasm or tumor, the neoplasms or tumors of cell proliferation diseases are the abnormal growth of tissue. Cell proliferation diseases refer to any kind of various malignant tumors characterized in cell proliferation. Tumours refer to any kind of various malicious tumours characterized by cell proliferation. Such tumors have the capability to intrude into surrounding tissues and/or transfer to new position of settlement.

In general, the cell proliferation diseases that can be treated with the compounds made public in this paper refer to any diseases characterized in abnormal cell proliferation. Those include various benign or malignant, transferred or non-transferred tumors and cancers. The method described in this paper may be used for confronting the particular characteristics of tumor, such as tissue invasion or transitivity. Cell proliferation diseases include various tumors. They include but not limited to:

Cancers: Including bladder cancer, breast cancer, colon cancer, renal cancer, liver cancer, lung cancer, cellule lung cancer, ovarian cancer, prostate cancer, pancreatic cancer, esophageal cancer, gastric cancer, gallbladder, cervical cancer, thyroid cancer and skin cancer, and squamous cell carcinoma;

Hematopoietic tumors of lymphatic system: Including leukemia, leukemia of acute lymphatic system, leukemia of acute lymphoblast, β-cell lymphoma, T-cell lymphoma, Hodgkins lymphoma, non-Hodgkins lymphoma, chorionic villus lymphoma and Burketts lymphoma;

Hematopoietic tumors of myeloid lineage: Including acute and chronic myelocytic leukemia, myelodysplastic syndromes and promyelocytic leukemia;

Tumors of central and peripheral nervous system: Including astrocytoma, neuroturbo chargeoma, glioma and schwannoma;

Neoplasms of mesenchymal origin: Including fibrosarcoma, rhabdomyosarcoma and osteosarcoma;

Other tumors: Including melanoma, xenoderma pigmentosum, amination acanthoma, seminoma, follicular thyroid carcinoma and teratocarcinoma.

The malignant proliferation diseases treated with above said compound include hematologic tumour. This tumor is the cell hyperplasia of hemopoietic system.

Hematologic tumours include lymphocytoma, wherein abnormal cell originates from lymphoid cell lineage cells and/or the characteristic phenotype displays lymphoid cell lineage cells. Lymphoid cell tumor may be subdivided into B cytoma, T and NK cytoma, and Hodgkin lymphoma. B cytoma can be further divided into ancestor B cytoma and mature/peripheral B cytoma. The illustrational B cytomais precursor B lymphocyte leukemia/lymphoma (precursor B cell acute lymphocyte leukemia), while the illustrational mature/peripheral B cytoma is B cell chronic lymphocyte leukemia/small lymphocyte lymphoma, B cell prolymphocyte leukemia, lymphoplasmacytic lymphoma, splenic marginal region B cell lymphoma, hairy cell leukemia, plasma cell myeloma/plasmacytoma, MALT type universal domain area B cell lymphoma, section area B cell lymphoma, follicle lymphoma, jacket cell lymphoma, diffuse large B cell lymphoma, mediastinal large B cell lymphoma, primary effusion lymphoma and Burkitt lymphoma/Burkitt cell leukemia. T cell and NK cytoma can be further divided into precursor T cell cancer and mature (peripheral) T cytoma. Illustrational precursor T cytoma is precursor T-lymphocyte lymphoma/leukemia (precursor T cell acute lymphocyte leukemia), while illustrational mature (peripheral) T cytoma is T cell-prolymphocyte leukemia T cell particle lymphocyte leukemia, aggressive NK cell leukemia, adult T cell lymphoma/leukemia (HTLV-1), extranodal nasal type NK/T cell lymphoma; nasal form, pathotype T cell lymphoma, hepatolienal γ-δ T cell lymphoma, subcutaneous panniculitis T cell lymphoma, granuloma fungoides/Sezary syndrome, retrogressive maxicell lymphoma; T/invalid cell, primary skin type peripheral T cell lymphoma, non-additionally characterized blood vessel immunoblastic lymphadenopathy T cell lymphoma, retrogressive maxicell lymphoma, T/invalid cell, primary body type. The third type of lymphoid cell tumor is Hodgkin lymphoma, also called as Hodgkin's disease. The illustrative diagnosis of the disease treated with the said compound includes but not limited to nodular lymphocyte predominant Hodgkin lymphoma and various Hodgkin's diseases in classic form, wherein the illustrational diseases are nodual hardening Hodgkin lymphoma (Level 1 and Level 2), lymphocyte-enriched classic Hodgkin lymphoma, Hodgkin lymphoma composed of mixed cells and lymphocytic depletion Hodgkin lymphoma.

Hematologic tumours also include myelocytome. Such tumor includes a major category of malignant proliferation disease involving or displaying the cell characteristic phenotype of myelocyte spectrum. Myelocytome may be subdivided into myeloproliferative disease, myeloproliferative disorder/myelodysplastic disease, myelodysplastic syndrome and acute myeloid leukemia. Illustrational myelodysplastic disease is chronic myelogenous leukemia, chronic neutrophils leukemia, chronic eosinophilic pneumonia leukemia/hypereosinophilic syndrome, chronic idiopathic myelofibrosis, polycythemia and primary thrombocythemia. Illustrational myeloproliferative disorder/myelodysplastic disease is chronic myelomonocytic leukemia, atypical chronic myelogenous leukemia and teenager acute myelomonocytic leukemia. Illustrational myelodysplastic syndrome is the refractory anemia with and without annular sideroblast, refractory pancytopenia (myelodysplastic syndrome) with multilinkage dysplasia, refractory anemia (myelodysplastic syndrome) with excessive germ cell, 5q-syndrome and myelodysplastic syndrome. In various embodiments, the compound of the present invention can be used for treating any relevant myelocytome.

The said compounds can be used for treating acute myeloid leukemia (AML). Such leukemia represents a major category of myelocytome in which the diseases may be further divided. Such branches include but not limited to AML with recurrent chromosomal translocation, AML with multilinkage dysplasia and other unclassified AMLs. AMLs with recurrent chromosomal translocation include but not limited to AML with t (8;21) (q22;q22), AML1 (CBF-α)/ETO, acute promyelocytic leukemia (AML with t(15;17)(q22;q11-12) and variants, PML/RAR-α), AML with abnormal eosinophil cell (inv(16) (p13 q22) or t(16;16)(p13;q11), CBFb/MYH11X) and 11q23 (MLL) abnormal AML. AMLs with multilinkage dysplasia are the AMLs relative to or irrelative to the foregoing myelodysplastic syndrome. Other acute myeloid leukemia not classified into the category of any definition includes minimally differentiated AML, immature AML, mature AML, acute myelomonocytic leukemia, acute mononuclear leukemia, acute red cell leukemia, acute megakaryocyte leukemia, acute basophil cell leukemia and acute total leukemia with myelofibrosis.

Preferably, the treated tumors are breast cancer, lung cancer, colon cancer, gastric cancer, esophagus cancer, ovarian cancer, osteosarcoma, cervical cancer, liver cancer, cerebroma, prostate cancer, and melanoma.

The term "treatment" used in the present invention indicates the relief of the symptom relating to symptom or disease or termination of the further development or deterioration of those symptoms, or stopping or preventing disease or symptom.

The term "pharmaceutical effective dose", "effective dose of treatment" or "therapeutically effective dose" refers to the quantity of the subject compound that research personnel, veterinarians, physicians or other clinical technicians are seeking the biological or medical reaction to tissue, system, animal or human.

The term "effective dose of treatment" includes the dose of compound delivered sufficient to stop the development of one or more symptoms of diseases or symptoms under treatment or to relieve to a certain degree. The effective dose of treatment should be changed with the compound, symptom or status and severity as well as the age, weight, etc. of the mammal treated.

The term "patient" defined in this paper includes animals, such as mammal Mammal includes but is not limited to primate (such as human), cow, sheep, goat, horse, dog, cat, rabbit, rat, mice, etc. In preferred embodiment, the patient is human. The effective dose of the compounds of the present invention may be decided by the general technical personnel in the field. For adult, the dosage is approximately 0.001-1000 mg of active compound per kg of weight per day. The drug may be administered in single dose or in respective divided dose, such as 1-4 times per day. It should be clear that, for any specific object, the specific dose level and administration frequency are variable and decided by many factors, including the activity of the specific compound used, metabolic stability and acting duration of the compound, species of administration object, age, weight, health status, sex, and dietary habit, way and time of administration, discharging rate, combination of drugs, and the severity of specific symptom.

Comparing with the antitumor platinum compound of the prior art, the solubility of the ionized compound of the present invention is obviously improved. The solubility of the compounds in the invention is above 50 mg/ml in water. Especially for the compounds in embodiments of the present invention, the solubility is generally 90 mg/ml and even up to more than 100 mg/ml. Moreover, the platinum compound of the prior art cannot be salinized. The compound of the present invention can produce salt form and is more favorable for producing into the form of stable preparation.

The above dosage forms of any compound containing effective dose are within the range of the conventional test and the present invention. Therapeutically effective dose may be adjusted according to the administration route and dosage form. The representative compound of the present invention is the preparation showing high therapeutic index. Therapeutic index is the dose ratio between toxicity and curative effect and can be expressed by the ratio between $LD_{50}$ and in vivo antitumor activity ($ED_{50}$) or in vitro cytotoxicity ($IC_{50}$). $LD_{50}$ is the lethal dose for 50% population; $ED_{50}$ is the therapeutically effective dose for 50% population. $LD_{50}$ and $ED_{50}$ are determined in animal cell culture medium or experimental animal through standard pharmaceutical method. Since $LD_{50}$ (lethal dose for 50% animal, mmol/kg) representing toxicity of the compound of the present invention is much higher than the platinum compound cisplatin and carboplatin, ADP, etc. of the existing technology and the effective dose of in vivo antitumor activity and in vitro concentration of inhibiting cell toxicity $IC_{50}$ value are equivalent or lower than carboplatin, it can be used for treating the patient who cannot tolerate the existing platinum compounds such as carboplatin, cisplatin, etc. and achieve better technical effect. The $IC_{50}$ value of the compound of the present invention is higher than 0.4 mmol/kg, preferably higher than 0.42 mmol/kg, more preferably higher than 0.45 mmol/kg, and most preferably higher than 0.5 mmol/kg. The compounds of the present invention may be individually use or used in combination, and/or in combined use with other suitable therapeutic agents used for treating proliferating diseases.

EMBODIMENTS

The following embodiments and test examples can describe the practicability of the present invention in details, but will not restrict the enablement of the present invention in any way. The technical personnel in this field should understand that any modification or substitution of appropriate technical characteristics according to the instructions of the existing technology remain within the range of protection claimed by the present invention. The purity of the raw materials used in the present invention is just above chemical purity. The said raw materials may be available on market. The compounds obtained in the following embodiments are in the form of salt. Ionized compounds may be obtained by adding alkali to regulate pH value of those compounds in the form of salt. The said compounds can be easily converted into other types of organic or inorganic salts by using the method of adding appropriate acid, which possibly include but not limited to nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactose acid salt, etc. This will not be explained again in the following embodiments one by one.

Embodiment 1

[2-(2-methylaminoethyl)-succinato].[Cis-diamine] platinum (II) phosphate;

Step 1: 2-(2-bromethyl)-diethyl succinate

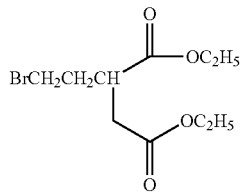

Diethyl succinate (17.42 g, 0.1 mol) and 1,2-dibromoethane (47.49 g, 0.25 mol) were placed into three 150 ml flasks. $K_2CO_3$ (15.3 g, 0.11 mol) and tetrabutylammonium bromide (155 mg) were added. The mixture was stirred and heated to 65~85° C. in oil bath for 16~24 h; suction filtration was conducted to remove solid which was washed with diethyl ether (30 ml×3 times), filtrate was consolidated; and washed with water (40 ml×3 times) then dried with $MgSO_4$ for 4~8 h; After removal of solvent, the distillate was collected for 137° C.-147° C. at vacuum 7 mmHg; the product was 8.46 g; and the yield was 30.1%.

Step 2: 2-(2-methylaminoethyl)-diethyl succinate

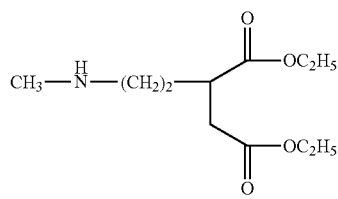

To the mixture of 2-bromethyl-diethyl succinate (106.83 g, 0.4 mol), anhydrous $K_2CO_3$ (55.85 g, 0.4 mol) in acetonitrile (500 ml), methylamine (31.2 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (90.3 g) was obtained; the oil was purified by column chromatography to afford the title compound (37.71 g) and the yield was 40.8%.

Step 3: 2-(2-methylaminoethyl)-succinate Disodium

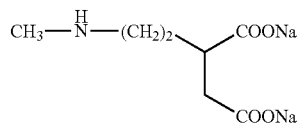

NaOH solution (215 mg, 5 mmol) added with water (2.5 mL) was added to 2-(2-methylaminoethyl)-diethyl succinate (460 mg, 2 mmol) in three 20 mL flasks; and the mixture was stirred at room temperature for 45~0.60 h, 2-(2-methylaminoethyl)-sodium succinate dibasic solution was obtained.

Step 4: Diamine.diiodo-platinum (II)

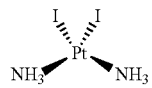

KI (6.640 g, 40 mmol) solution (50 ml) was added to potassium chloroplatinite ($K_2PtCl_4$) (2.075 g, 5 mmol) in water (50 ml), the mixture was stirred and heated to 40~60° C. away from light and oxygen for 0.5~2 h, and then ammonia water (50 ml) (containing 5 mmol ammonia) was added; and the reaction mixture was kept under this condition for 0.5~2 h. Light yellow solid product (2.29 g) was obtained by suction filtration and washed successively with water (10 ml×3 times) and diethyl ether (10 ml×3 times); the yield was 95.1%. Elemental analysis: H1.24% (theoretical 1.21%); N5.56% (theoretical 5.797%).

Step 5: Diamine.dihydrate platinum (II) sulphate

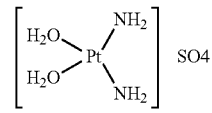

Adding $Ag_2SO_4$ (625 mg, 2 mmol) in water (30 ml) and stirring, diamine.diiodo-platinum (II) (0.96 g, 2 mmol) was added and another part of water (40 ml) was added to the reaction mixture; the mixture was stirred and heated at 40~60° C. for 4~8 h. After removing AgI deposit by suction, the filtrate was the aqueous solution of the product.

Step 6: [2-(2-methylaminoethyl)-succinato].[Cis-diammine]platinum (II) phosphate

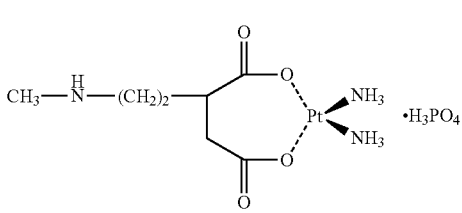

2-(2-methylaminoethyl)-succinate disodium solution (2 mmol) was regulated the pH to 5~7 with $H_3PO_4$(1M) and then Cis-diamine.dihydrate platinum (II) sulphate aqueous solution was poured into reaction mixture; the mixture was heated in water bath to 40~75° C. for 4-6 h. Under $N_2$ protection; after filtration, reaction mixture was concentrated to a certain volume and should be at a standstill; crystalline-type [2-(2-methylaminoethyl)-succinato].[Cis-diamino]platinum (II) phosphate (111 mg) is obtained.

$^1$HNMR ($D_2O$) (ppm): δ3.50 (m, 1H), δ3.42 (d, 2H), δ2.87 (s, 3H), δ2.65 (t, 2H), δ1.75 (m, 2H).

The said compound is soluble in water. The solubility is 208 mg/ml. Through free base, the compound can be easily transferred into organic or inorganic salt in other categories and may be but not limited to sulfate, mesylate, tartrate, succinate, phosphate, citrate, tosilate, formarate, etc. Free base elemental analysis: C120.59% (theoretical 20.90%); H4.44% (theoretical 4.23%); N10.58% (theoretical 10.45%).

Embodiment 2

[2-(2-dimethylaminoethyl)-succinato].[Cis-diamine]platinum (II) acetate;

Step 1: Same as [Embodiment 1] Step 1

Step 2: 2-(2-dimethylamine)-diethyl succinate

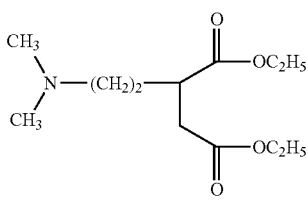

To the mixture of 2-broethyl-diethyl succinate (112.62 g, 0.4 mol), anhydrous $K_2CO_3$ (55.56 g, 0.4 mol) in acetonitrile (500 ml), dimethylamine (45.2 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (92.51 g) was obtained; the oil was purified by column chromatography to afford the title compound (44.30 g) and the yield was 45.2%.

Step 3: 2-(2-dimethylamine)-succinate disodium

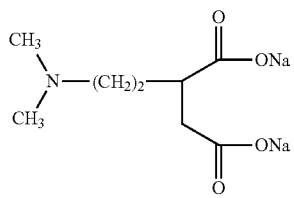

2M solution (2.5 mL) from NaOH (214 mg) with water was added to 2-(2-dimethylamine)-diethyl succinate (488 mg, 2 mmol) in three 20 mL flasks; and the mixture was stirred at room temperature for 45~0.60 h, 2-(2-dimethylamine)-sodium succinate dibasic solution was obtained.

Step 4, 5: Same as [Embodiment 1] Step 4, 5

Step 6: [2-(2-dimethylamine)-succinato].[Cis-diamine]platinum (II) acetate

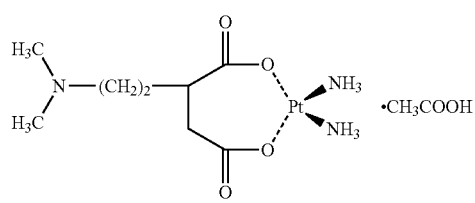

2-(2-dimethylamine)-succinate disodium solution (2 mmol) was regulated to the pH 5~7 with $CH_3COOH$ (1M) and then Cis-diamine.dihydrate platinum (II) sulphate aqueous solution was poured into reaction mixture; the mixture was heated in water bath to 40~75° C. for 4-6 h. Under $N_2$ protection; after filtration through celite, reaction mixture was concentrated to a certain volume and should be at a standstill; crystalline-type [2-(2-dimethylamine)-succinato].[Cis-diamine]platinum (II) acetatedimethylamine (110 mg) was obtained.

$^1$HNMR ($D_2O$) (ppm): δ3.55 (m, 1H), δ3.45 (d, 2H), δ2.66 (s, 6H), δ2.55 (t, 2H), δ1.74 (m, 2H).

Both the free base and salt of the said compound are soluble in water. The solubility is 176 mg/ml. It can be easily transferred into other types of organic or inorganic salts through ionization. It may be but not limited to sulphate, mesylate, tartrate, succinate, acetate, citrate, tosilate, fumarate, etc. Free base elemental analysis: C23.22% (theoretical 23.1%); H4.49% (theoretical 4.57%); N9.82% (theoretical 10.1%).

Embodiment 3

[2-(3-dimethylamino propyl)-succinato].[Cis-diamine]platinum (II) phosphate

Step 1: 2-(3-bromopropyl)-diethyl succinate

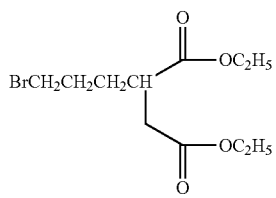

Diethyl succinate (17.25 g, 0.1 mol) and 1,3-dibromoethane (50.5 g, 0.25 mol) were placed into three 150 ml flasks. $K_2CO_3$ (15.12 g, 0.11 mol) and tetrabutylammonium bromide (155 mg) were added. The mixture was stirred and heated to 65~85° C. in oil bath for 16~24 h; suction filtration was conducted to remove solid which was washed with diethyl ether (30 ml×3 times), filtrate consolidated was washed with water (40 ml×3 times) and dried over anhydrous $MgSO_4$ for 4-8 h. After removal of solvent, the distillate was collected for 139-149° C. at vacuum 7 mmHg; the product was 9.58 g; and the yield was 32.47%

Step 2: 2-(3-dimethylamino propyl)-diethyl succinate

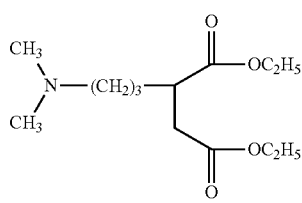

To the mixture of 2-bropropyl-diethyl succinate (117.9 g, 0.4 mol), anhydrous $K_2CO_3$ (55.65 g, 0.4 mol) in acetonitrile (500 ml), dimethylamine (45.1 g, 1.0 mol) solution in refrigerated was added and the mixture was heated at 40~60° C. for 2-6 h; insoluble substance was filtered out and the filtrate was concentrated in vacuo; the residue was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (102.3 g) was obtained; the oil was purified by column chromatography to afford the title compound (33.2 g) and the yield was 32.05%.

Step 3: 2-(3-dimethylamino propyl)-succinate disodium

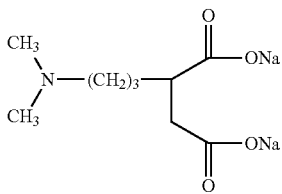

2M NaOH solution (2.5 mL) was added to 2-(2-dimethylaminepropyl)-diethyl succinate (518 mg, 2 mmol) in three 20 mL flasks; and the mixture was stirred at room temperature for 45~60 h, 2-(3-dimethylamino propyl)-sodium succinate dibasic solution is obtained.

Step 4, 5: Same as [Embodiment 1] Step 4, 5

Step 6: [2-(3-dimethylamino propyl)-succinato].[Cis-diamine]platinum (II) phosphate

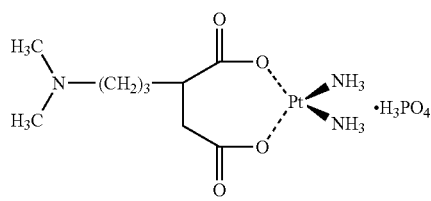

2-(3-dimethylamino propyl)-succinate disodium solution was regulated to the pH 5~7 with $H_3PO_4$(1M) and then Cis-diamine.dihydrate platinum (II) sulphate aqueous solution was poured into reaction mixture; the mixture was heated in water bath to 40~75° C. for 4-6 h. Under $N_2$ protection; after filtration, the filtrate was concentrated to a certain volume and should be at a standstill; crystalline-type [2-(3-dimethylamino propyl)-succinato].[Cis-diamine]platinum (II) phosphateethylaminoethyl (119 mg) was obtained.

$^1$HNMR ($D_2O$) (ppm): δ3.52 (m, 1H), δ3.42 (d, 2H), δ2.75 (s, 6H), δ2.69 (t, 2H), δ1.75 (m, 2H), δ1.49 (m, 2H).

Both the free base and salt of the said compound are soluble in water. The solubility is 150 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C25.23% (theoretical 25.12%); H4.63% (theoretical 4.88%); N9.82% (theoretical 9.77%).

Embodiment 4

[2-(3-amino propyl)-succinato].[Cis-diamine]platinum (II) phosphate

Step 1: Same as [Embodiment 3] Step 1

Step 2: 2-(3-amino propyl)-diethyl succinate

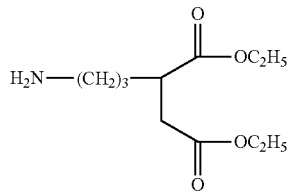

To the mixture of 2-bropropyl-diethyl succinate (118.2 g, 0.4 mol), anhydrous $K_2CO_3$ (55.3 g, 0.4 mol) in acetonitrile (500 ml), excessive ammonia was bubbled into mixture which was then heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (87.8 g) was obtained; the oil was purified by column chromatography to afford the title compound (34.1 g) and the yield was 36.9%.

Step 3: 2-(3-amino propyl)-succinate disodium

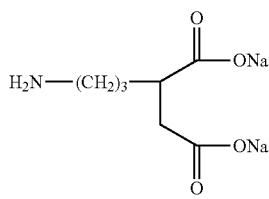

2M NaOH solution (2.5 mL) was added to 2-(3-aminopropyl)-diethyl succinate (463 mg, 2 mmol) in three 20 mL flasks; and the mixture was stirred at room temperature for 45~60 h, 2-(3-aminopropyl)-sodium succinate dibasic solution was obtained.

Step 4, 5: Same as [Embodiment 1] Step 4, 5

Step 6: [2-(3-amino propyl)-succinato].[Cis-diamine]platinum (II) phosphate

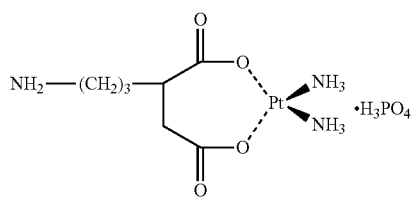

2-(3-aminopropyl)-sodium succinate dibasic solution was regulated to the pH 5~7 with H₃PO₄ M) and then Cis-diamine.dihydrate platinum (II) sulphate aqueous solution was added into reaction mixture which was then heated in water bath to 40~75° C. for 4-6 h. Under $N_2$ protection; after filtration, the filtrate was concentrated to a certain volume and should be at a standstill; crystalline-type [2-(3-amino propyl)-succinato].[Cis-diamine]platinum (II) phosphate (118 mg) was obtained.

¹HNMR (D₂O)(ppm): δ3.52 (m, 1H), δ3.42 (d, 2H), δ2.88 (t, 2H), δ1.78 (m, 2H), δ1.52 (m, 2H).

Both the free base and salt of the said compound are soluble in water. The solubility is 155 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C20.67% (theoretical 20.90%); H4.41% (theoretical 4.23%); N10.72% (theoretical 10.45%).

Embodiment 5

[2-(2-diethylin aminoethyl)-succinato].[Cis-diamine]platinum (II) phosphate

Step 1: Same as [Embodiment 1] Step 1

Step 2: 2-(2-diethylin aminoethyl)-diethyl succinate

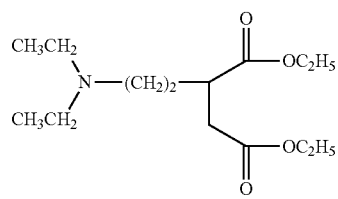

To the mixture of 2-broethyl-diethyl succinate (112.72 g, 0.4 mol), anhydrous K₂CO₃ (55.6 g, 0.4 mol) in acetonitrile (500 ml), dimethylamine (73.2 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO₄ overnight; after removal of solvent in vacuo, light yellow oil (102.5 g) was obtained; the oil was purified by column chromatography to afford the title compound (47.17 g) and the yield was 43.2%.

Step 3: 2-(2-diethylin aminoethyl)-succinate disodium

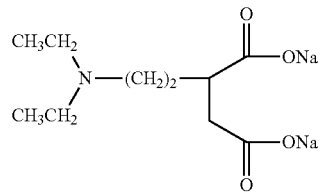

2M NaOH solution (2.5 mL) was added to 2-(2-diethylin aminoethyl)-diethyl succinate (548 mg, 2 mmol) in 20 mL flasks; and the mixture was stirred at room temperature for 45~60 h, 2-(2-diethylin aminoethyl)-sodium succinate dibasic solution was obtained.

Step 4, 5: Same as [Embodiment 1] Step 4, 5

Step 6: [2-(2-diethylin aminoethyl)-succinato].[Cis-diamine]platinum (II) phosphate

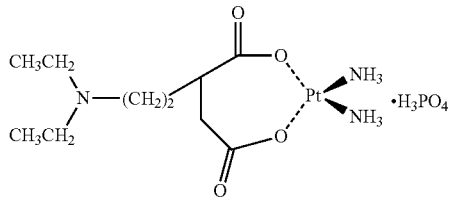

2-(2-diethylin aminoethyl)-succinate disodium solution was regulated to the pH 5~7 with H₃PO₄ (1M) and then Cis-diamine.dihydrate platinum (II) sulphate aqueous solution was poured into reaction mixture; the mixture was heated in water bath to 40~75° C. for 4-6 h. Under N₂ protection; after filtration, reaction mixture was concentrated to a certain volume and should be at a standstill; crystalline-type [2-(2-diethylin aminoethyl)-succinato].[Cis-diaminum (II) diethylin aminoethyl phosphate (121 mg) was obtained.

¹HNMR (D₂O)(ppm): δ3.51 (m, 1H), δ3.41 (d, 2H), δ2.78 (q, 4H), δ2.70 (t, 2H), δ1.70 (m, 2H), δ1.08 (t, 6H).

Both the free base and salt of the said compound are soluble in water. The solubility is 166 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C26.96% (theoretical 27.03%); H5.24% (theoretical 5.18%); N9.56% (theoretical 9.46%).

Embodiment 6

[2-(3-di-n-propylamino propyl)-succinato].[Cis-diamine]platinum (II) mesylate

Step 1: Same as [Embodiment 3] Step 1

Step 2: 2-(3-di-n-propylamino propyl)-diethyl succinate

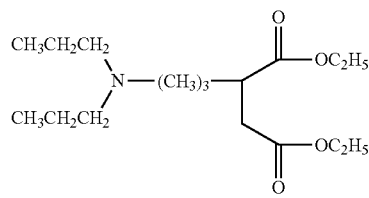

To the mixture of 2-bropropyl-diethyl succinate (116.0 g, 0.4 mol), anhydrous K$_2$CO$_3$ (55.3 g, 0.4 mol) in acetonitrile (500 ml), di-n-propylamine (101 g, 1.0 mol) solution refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO$_4$ overnight; after removal of solvent in vacuo, light yellow oil (106.5 g) was obtained; the oil was purified by column chromatography to afford the title compound (43.1 g) and the yield was 34.2%.

Step 3: 2-(3-di-n-propylamino propyl)-succinate disodium

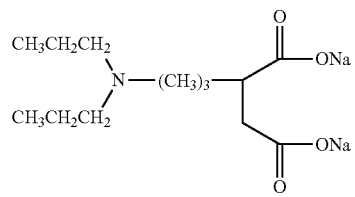

2M NaOH solution (2.5 mL) was added to 2-(3-di-n-propylamino propyl)-diethyl succinate (603 mg, 2 mmol) in three 20 mL flasks; and the mixture was stirred at room temperature for 45~60 h, 2-(3-di-n-propylamino propyl)-succinate disodium solution was obtained.

Step 4, 5: Same as [Embodiment 1] Step 4, 5

Step 6: [2-(3-di-n-propylamino propyl)-succinato].[Cis-diamine]platinum (II) mesylate 2-(3-di-n-propylamino propyl)-disodium succinate solution was regulated to the pH 5~7 with CH$_3$SO$_3$H (1M) and then Cis-diamine.dihydrate platinum (II) sulphate aqueous solution was poured into reaction mixture; the mixture was heated in water bath to 40~75° C. for 4-6 h. Under N$_2$ protection; after filtration through celite, reaction mixture was concentrated to a certain volume and should be at a standstill; crystalline-type [2-(3-di-n-propylamino propyl)-succinato].[Cis-diamine]platinum (II) mesylatepropylamino propyl (129 mg) is obtained.

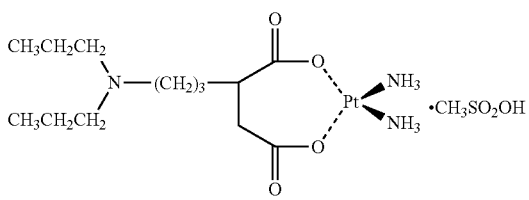

$^1$HNMR (D$_2$O)(ppm): δ3.52 (m, 1H), δ3.42 (d, 2H), δ2.77 (t, 4H), δ2.70 (t, 2H), δ1.74 (m, 2H), δ1.49 (m, 2H), 61.25 (m, 4H), δ1.03 (t, 6H).

Both the free base and salt of the said compound are soluble in water. The solubility is 130 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C32.22% (theoretical 32.1%); H5.72% (theoretical 5.97%); N8.66% (theoretical 8.64%).

Embodiment 7

[2-(3-(1-piperidyl)-propyl)-succinato].[Cis-diamine] platinum (II) phosphate

Step 1: Same as [Embodiment 3] Step 1

Step 2: 2-(3-(1-piperidyl)-propyl)-diethyl succinate

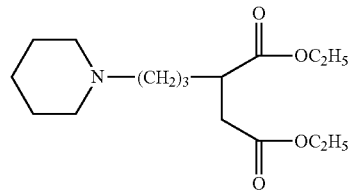

To the mixture of 2-bropropyl-diethyl succinate (117.7 g, 0.4 mol), anhydrous K$_2$CO$_3$ (55.63 g, 0.4 mol) in acetonitrile (500 ml), piperidine solution (85.0 g, 1.0 mol) was added into mixture which was then heated at 40-60° C. for 2-6 h; insoluble substance is filtered out and the filtrate was concentrated in vacuo; the residues was dissolved with 1000 ml ethyl acetate; organic phase was washed with saturate NaCl aqueous solution (250 ml×3 times) and dried over anhydrous MgSO$_4$ overnight; after removal of solvent in vacuo, light yellow oil (100.4 g) was obtained; the oil was purified by column chromatography to afford the title compound (34.35 g) and the yield was 28.72%.

Step 3: 2-(3-(1-piperidyl)-propyl)-succinate disodium

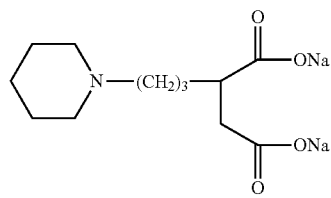

2M NaOH solution (2.5 mL) was added to 2-(3-(1-piperidyl)-propyl)-diethyl succinate (600 mg, 2 mmol) in three 20 mL flasks; and the mixture was stirred at room temperature for 45~60 h, 2-(3-(1-piperidyl)-propyl)-diethyl succinate disodium salt solution was obtained.

Step 4, 5: Same as [Embodiment 1] Step 4, 5

Step 6: [2-(3-(1-piperidyl)-propyl]-succinatol.[Cis-diamine]platinum (II) phosphate

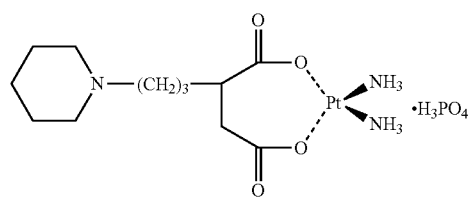

2-(3-(1-piperidyl)-propyl)-succinate disodium salt solution was regulated to the pH 5~7 with $H_3PO_4$(1M) and then aqueous Cis-diamine.dihydrate platinum (II) sulphate was poured into reaction mixture; the mixture was heated in water bath to 40~75° C. for 4-6 h, the mixture was concentrated to certain volume and the residue was standstill at room temperature; the title compound (141 mg) was obtained by suction.

$^1$HNMR ($D_2O$)(ppm): δ3.52 (m, 1H), δ3.42 (d, 2H), δ2.83 (m, 4H), δ2.70 (m, 2H), δ1.85 (m, 2H), δ1.77 (m, 4H), δ1.52 (m, 2H), δ1.37 (m, 2H).

The said compound is soluble in water. The solubility is 139 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C30.55% (theoretical 30.64%); H5.33% (theoretical 5.32%); N8.82% (theoretical 8.943%).

Embodiment 8

[2-(3-(1-pyrrolidyl)-propyl)-succinato].[Cis-diamine]platinum (II) phosphate

Step 1: Same as [Embodiment 3] Step 1

Step 2: 2-(3-(1-pyrrolidyl)-propyl)-diethyl succinate

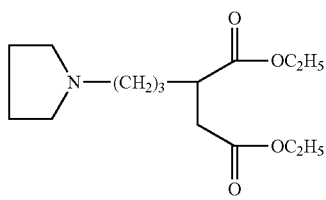

To the mixture of 2-bropropyl-diethyl succinate (117.6 g, 0.4 mol), anhydrous $K_2CO_3$ (55.72 g, 0.4 mol) in acetonitrile (500 ml), pyrrolidine solution (71.2 g, 1.0 mol) was added into mixture which was then heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (93.3 g) was obtained; the oil was purified by column chromatography to afford the title compound (29.85 g) and the yield was 26.18%.

Step 3: 2-(3-(1-pyrrolidyl)-propyl)-succinate disodium salt

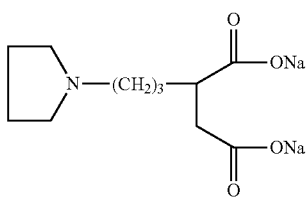

2M NaOH solution (2.5 mL) was added to 2-(3-(1-pyrrolidyl)-propyl)-diethyl succinate (572 mg, 2 mmol) in three 20 mL flasks; and the mixture was stirred at room temperature for 45~60 h, 2-(3-(1-pyrrolidyl)-propyl)-succinate disodium solution was obtained.

Step 4, 5: Same as [Embodiment 1] Step 4, 5

Step 6: [2-(3-(1-pyrrolidyl)-propyl)-succinato].[Cis-diamine]platinum (II) phosphate

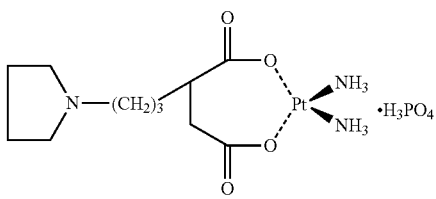

2-(3-(1-pyrrolidyl)-propyl)-succinate disodium solution was regulated to the pH 5~7 with H3PO4 (1M) and then aqueous Cis-diamine.dihydrate platinum (II) sulphate was poured into reaction mixture; the mixture was heated in water bath to 40~75° C. for 4-6 h, the mixture was concentrated to certain volume and the residue was standstill at room temperature; the title compound (121 mg) was obtained by suction.

$^1$HNMR ($D_2O$)(ppm): δ3.51 (m, 1H), δ3.46 (d, 2H), δ2.85 (m, 4H), δ2.71 (m, 2H), δ1.85 (m, 2H), δ1.79 (m, 4H), δ1.51 (m, 2H).

The free alkali and salt of the said compound are soluble in water. The solubility is 135 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C28.73% (theoretical 28.95%); H4.97% (theoretical 5.04%); N9.31% (theoretical 9.21%).

Embodiment 9

[2-(2-aminoethyl)-succinato].[Cis-(1,2-trans-cyclohexyl diamine)]platinum (II) phosphate Step 1: Same as [Embodiment 1] Step 1

Step 2: 2-(2-aminoethyl)-diethyl succinate

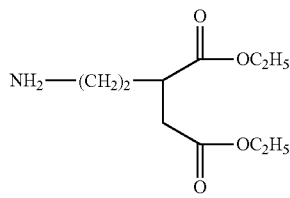

To the mixture of 2-bromethyl-diethyl succinate (109.3 g, 0.4 mol), anhydrous $K_2CO_3$ (55 g, 0.4 mol) in acetonitrile (500 ml), excessive ammonia was added and the mixture was heated at 40~60° C. for 2-6 h; insoluble substance is filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (80.5 g) was obtained; the oil was purified by column chromatography to afford the title compound (32.6 g) and the yield was 40.0%.

Step 3: 2-(2-aminoethyl)-succinate disodium

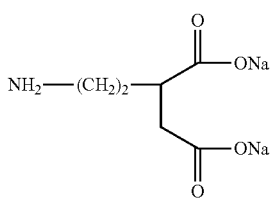

2M NaOH solution (2.5 mL) was added to 2-(2-aminoethyl)-diethyl succinate (418 mg, 2 mmol) in three 20 mL flasks; and the mixture was stirred at room temperature for 45~60 h, 2-(2-aminoethyl)-sodium succinate dibasic solution was obtained.

Step 4: trans-cyclohexyl diamine diamine.diiodo-platinum (II)

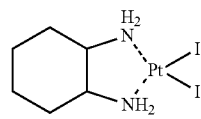

KI (6.640 g, 40 mmol) solution (50 ml) was added to potassium chloroplatinite ($K_2PtCl_4$) (2.075 g, 5 mmol) in water (50 ml), the mixture was stirred and heated to 40-60° C. away from light and oxygen for 0.5~2 h., and then trans-cyclohexyl diamine (571 g, 5 mg, 5 mmol) in water (50 ml) was added; and the reaction mixture was kept under this condition for 0.5~2 h. Yellow solid product (2.709 g) was obtained by suction filtration and washed successively with water (10 ml×3 times) and diethyl ether (10 ml×3 times; the yield was 96.2%. Elemental analysis: C12.68% (theoretical 12.80%); H2.61% (theoretical 2.51%); N4.99% (theoretical 4.98%).

Step 5: Trans-cyclocyclohexyl diamine.dihydrate platinum (II) sulphate

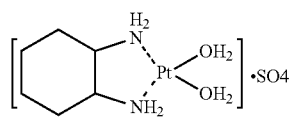

Stirring $Ag_2SO_4$ (625 mg, 2 mmol) in water (30 ml), trans-cyclohexamethylene.diiodo-platinum (II) (1.126 g, 2 mmol) was added and another part of water (40 ml) was added to the reaction mixture; the mixture was stirred and heated at 40~60° C. for 4-8 h. After removing AgI deposit by suction. The filtrate was the aqueous solution of the product.

Step 6: [2-(2-aminoethyl)-succinato].[Cis-(1,2-trans-cyclocyclohexyl diamine)]platinum (II) phosphate

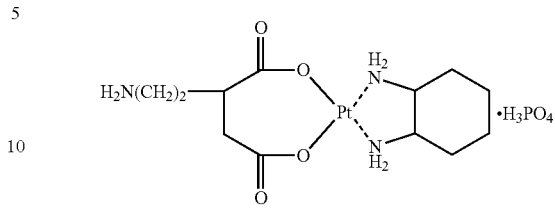

2-(2-aminoethyl)-sodium succinate dibasic solution was regulated to the pH 5~7 with $H_3PO_4$ (1M) and then aqueous trans-cyclohexyl diamine.dihydrate platinum (II) sulphate was poured into reaction mixture; the mixture was heated in water bath to 40~60° C. for 4-8 h.; and then added 2.5 g silica into it; the mixture was stirred for 15 min and concentrated to dry, the residue was purified by column chromatography to afford the title compound (131 mg).

$^1$HNMR ($D_2O$) (ppm): δ3.51 (m, 1H), δ3.41 (d, 2H), δ2.78 (t, 2H), δ2.06 (br, 2H), δ1.81 (m, 2H), δ1.74 (m, 2H), δ1.46 (m, 2H), 61.21 (br, 2H), δ1.01 (m, 2H).

The said compound is soluble in water. The solubility is 248 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C30.51% (theoretical 30.77%); H4.83% (theoretical 4.91%); N9.15% (theoretical 8.97%).

Embodiment 10

[2-(2-diethylin aminoethyl)-succinato].[Cis-(1,2-trans-cyclohexyl diamine)]platinum (II) tosilate Step 1: Same as [Embodiment 1] Step 1

Step 2, 3: Same as [Embodiment 5] Step 2, 3

Step 4, 5: Same as [Embodiment 9] Step 4, 5

Step 6: [2-(2-diethylin aminoethyl)-succinato].[Cis-(1,2-trans-cyclocyclohexyl diamine)]platinum (II) tosylate

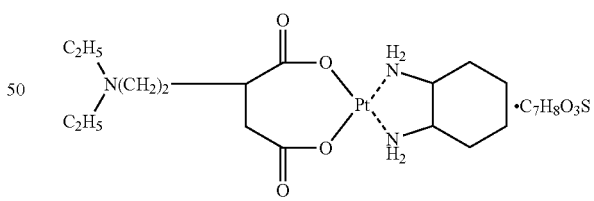

2-(2-dimethylamine)-succinate disodium solution was regulated to the pH 5~7 with p-toluenesulfonic acid (1M) and then aqueous trans-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (143 mg).

$^1$HNMR ($D_2O$)(ppm): δ3.53 (m, 1H), δ3.43 (d, 2H), δ2.68 (br, 4H), 62.55 (t, 2H), δ2.06 (br, 2H), δ1.81 (m, 2H), δ1.74 (m, 2H), δ1.46 (m, 2H), δ1.21 (br, 2H), 1.12 (t, 6H), δ1.05 (m, 2H).

The said compound is soluble in water. The solubility is 214 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C36.54% (theoretical 36.64%); H5.78% (theoretical 5.92%); N8.17% (theoretical 8.02%).

Embodiment 11

[2-(3-dimethylamino propyl)-succinato].[Cis-(1,2-trans-cyclocyclohexyl diamine)]platinum (II) phosphate Step 1, 2, 3: Same as [Embodiment 3] Step 1, 2, 3

Step 4, 5: Same as [Embodiment 9] Step 4, 5

Step 6: [2-(3-dimethylamino propyl)-succinato].[Cis-(1,2-trans-cyclocyclohexyl diamine)]platinum (II) phosphate

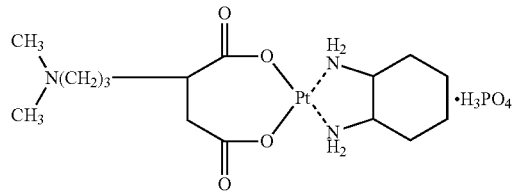

2-(3-dimethylamino propyl)-succinate disodium solution was regulated to the pH 5~7 with $H_3PO_4$ (1M) and then aqueous trans-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (135 mg).

$^1$HNMR ($D_2O$)(ppm): δ3.51 (m, 1H), δ3.41 (d, 2H), δ2.75 (s, 6H), δ2.69 (t, 2H), δ2.06 (br, 2H), δ1.81 (m, 2H), δ1.74 (m, 2H), δ1.49 (m, 2H), δ1.46 (m, 2H), δ1.21 (br, 2H), δ1.02 (m, 2H).

The said compound is soluble in water. The solubility is 178 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C35.51% (theoretical 35.29%); H5.49% (theoretical 5.69%); N8.26% (theoretical 8.24%).

Embodiment 12

[2-(2-ethylaminoethyl)-succinato].[Cis-(1,2-trans-cyclocyclohexyl diamine)]platinum (II) phosphate Step 1: Same as [Embodiment 1] Step 1

Step 2: 2-(2-ethylaminoethyl)-diethyl succinate

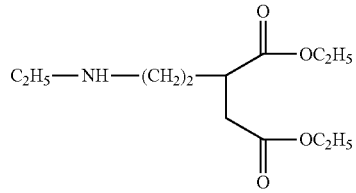

To the mixture of 2-bromethyl-diethyl succinate (112.2 g, 0.4 mol), anhydrous $K_2CO_3$ (55.1 g, 0.4 mol) in acetonitrile (500 ml), ethylamine (44.3 g, 1.0 mol) refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (90.5 g) was obtained; the oil was purified by column chromatography to afford the title compound (36.3 g) and the yield was 37.0%.

Step 3: 2-(2-ethylaminoethyl)-succinate disodium

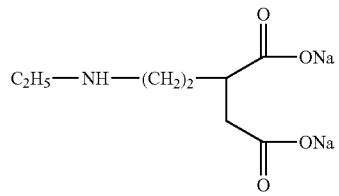

2M NaOH solution (2.5 mL) was added to 2-(2-ethylaminoethyl)-diethyl succinate (490 mg, 2 mmol) in 20 mL flasks; and the mixture was stirred at room temperature for 45~60 h, 2-(2-ethylaminoethyl)-sodium succinate dibasic solution was obtained.

Step 4, 5: Same as [Embodiment 9] Step 4, 5

Step 6: [2-(2-ethylaminoethyl)-succinato].[Cis-(1,2-trans-cyclocyclohexyl diamine)]platinum (II) phosphate

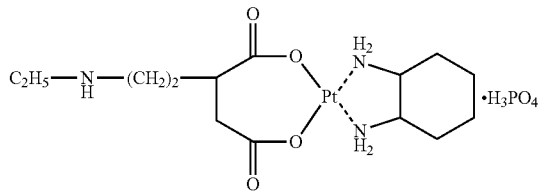

2-(2-ethylaminoethyl)-succinate disodium solution was regulated to the pH 5~7 with $H_3PO_4$ (1M) and then aqueous trans-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (141 mg).

$^1$HNMR ($D_2O$)(ppm): δ3.50 (m, 1H), δ3.40 (d, 2H), δ2.78 (m, 2H), 62.70 (t, 2H), 2.06 (br, 2H), 1.81 (m, 2H), δ1.70 (m, 2H), 1.46 (m, 2H), 1.21 (br, 2H), 61.08 (t, 3H) 1.00 (m, 2H).

The said compound is soluble in water. The solubility is 191 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C33.59% (theoretical 33.87%); H5.21% (theoretical 5.44%); N8.66% (theoretical 8.47%).

Embodiment 13

[2-(3-(1-piperidyl) propyl)-succinato].[Cis-(1,2-trans-cyclohexyl diamine)]platinum (II) phosphate Step 1: Same as [Embodiment 3] Step 1

Step 2, 3: Same as [Embodiment 7] Step 2, 3

Step 4, 5: Same as [Embodiment 9] Step 4, 5

Step 6: [2-(3-(1-piperidyl) propyl)-succinato].[Cis-(1,2-trans-cyclohexyl diamine)]platinum (II) citrate

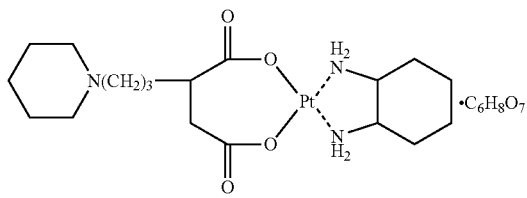

2-(3-(1-piperidyl)propyl)-succinato solution was regulated to the pH 5~7 with citric acid $C_6H_8O_7$(1M) and then aqueous trans-cyclohexyl diamine.dihydrate platinum (II) sulphate was poured into reaction mixture; under protection of $N_2$, the mixture was heated in water bath to 40~60° C. for 4-8 h; and then added 2.5 g silica into it; the mixture was stirred for 15 min and concentrated to dry, the residue was purified by column chromatography to afford the title compound (175 mg).
$^1$HNMR ($D_2O$)(ppm): δ3.52 (m, 1H), δ3.42 (d, 2H), 52.78 (m, 4H), 62.70 (t, 2H), δ2.06 (br, 2H), δ1.81 (m, 2H), δ1.70 (m, 2H), δ1.46 (m, 2H), δ1.37 (m, 2H), δ1.21 (br, 2H), δ1.15 (m, 4H), δ1.08 (m, 2H), δ1.00 (m, 2H).

The said compound is soluble in water. The solubility is 160 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C39.41% (theoretical 39.27%); H6.13% (theoretical 6.0%); N7.59% (theoretical 7.64%).

Embodiment 14

[2-(3-di-n-propylamino propyl)-succinato].[Cis-(1,2-trans-cyclocyclohexyl diamine)]platinum (II) phosphate Step 1: Same as [Embodiment 3] Step 1

Step 2, 3: Same as [Embodiment 6] Step 2, 3

Step 4, 5: Same as [Embodiment 9] Step 4, 5

Step 6: [2-(3-di-n-propylamino propyl)-succinato].[Cis-(1,2-trans-cyclocyclohexyl diamine)]platinum (II) phosphate

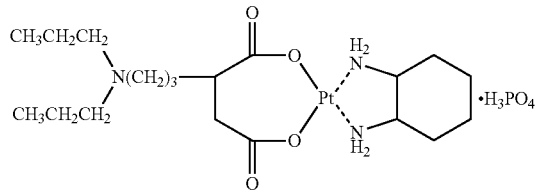

2-(3-di-n-propylamino propyl)-succinate disodium solution was regulated to the pH 5~7 with $H_3PO_4$(1M) and then aqueous trans-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (157 mg).
$^1$HNMR ($D_2O$)(ppm): δ3.52 (m, 1H), δ3.41 (t, 2H), δ2.77 (t, 4H), δ2.70 (t, 2H), δ2.06 (br, 2H), δ1.81 (m, 2H), δ1.74 (m, 2H), δ1.49 (m, 2H), δ1.46 (m, 2H), δ1.25 (m, 4H), δ1.21 (br, 2H), δ1.03 (t, 6H), δ1.00 (m, 2H).

The said compound is soluble in water. The solubility is 100 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C40.37% (theoretical 40.28%); H6.33% (theoretical 6.54%); N7.22% (theoretical 7.42%).

Embodiment 15

[2-(3-diethylamino propyl)-succinato].[Cis-(1,2-trans-cyclopentyl diamine)]platinum (II) phosphate Step 1: Same as [Embodiment 3] Step 1

Step 2: 2-(3-diethylamino propyl)-diethyl succinate

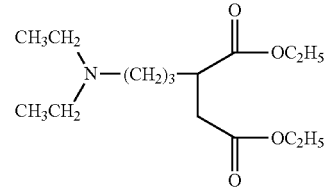

To the mixture of 2-bropropyl-diethyl malonate (118 g, 0.4 mol), anhydrous $K_2CO_3$ (55.5 g, 0.4 mol) in acetonitrile (500 ml), dimethylamine (73.1 g, 1.0 mol) solution in refrigerated was added and the mixture was heated at 40~60° C. for 2-6 h; insoluble substance was filtered out and the filtrate was concentrated in vacuo; the residue was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (107.1 g) was obtained; the oil was purified by column chromatography to afford the title compound (39.8 g) and the yield was 34.67%.

Step 3: 2-(3-diethylamino propyl)-succinate disodium

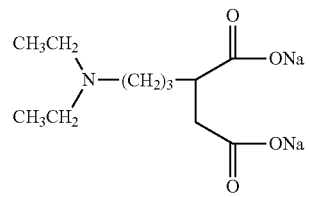

2M NaOH solution (2.5 mL) was added to 2-(3-diethylamino propyl)-sodium succinate (572 mg, 2 mmol) in three 20 mL flasks; and the mixture was stirred at room temperature for 45~60 h, 2-(2-aminoethyl)-sodium succinate dibasic solution was obtained.

Synthesized Step 4: 1,2-trans-diaminocyclopentane

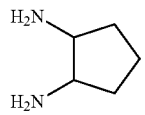

To the solution of cyclopentene (6.81 g, 100 mmol) in dichloromethane (30 ml), Br$_2$ (16.5 g, 103 mmol) was added dropwise slowly at −5~10° C. and stirred for 1~3 h, organic layer was washed with saturate sodium bicarbonate solution (10 ml×3 times) and dry with anhydrous MgSO$_4$ for 2-3 h; after removal of solvent in vacuo, 1,2-trans-dibromo cyclopentane (20.56 g) as light yellow transparent oil was obtained; and the yield is 90.18%. Elemental analysis: C26.51% (theoretical 26.32%); H3.62% (theoretical 3.51%).

1,2-trans-dibromo cyclopentane (11.5 g, 50 mmol) and 30% ammonia ethanol solution (30 ml) was added into 100 ml pressure reactor; the mixture was heated to 40-60° C. and stirred for 6-8 h; After removal of solvent in vacuo to afford 1,2-trans-cyclopentylamine (4.015 g) as light yellow transparent oil; and the yield was 79.6%. Elemental analysis: C60.21% (theoretical 60%); H12.12% (theoretical 12%); N28.21% (theoretical 28%).

Step 5:
1,2-trans-diaminocyclopentane.diiodo-platinum (II)

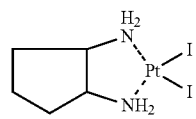

KI (6.630 g, 40 mmol) solution (50 ml) was added to potassium chloroplatinite (K$_2$PtCl$_4$) (2.073 g, 5 mmol) in water (50 ml), the mixture was stirred and heated to 40-60° C. away from light and oxygen for 0.5~2 h., and then 1,2-trans-diaminocyclopentane (501 g, 5 mg, 5 mmol) in water (50 ml) was added; and the reaction mixture was kept under this condition for 0.5~2 h. Yellow solid product (2.56 g) was obtained by suction filtration and washing successively with water (10 ml×3 times) and diethyl ether (10 ml×3 times); the yield was 93.1%. Elemental analysis: C10.78% (theoretical 10.93%); H2.31% (theoretical 2.19%); N4.98% (theoretical 5.10%).

Step 6: 1,2-trans-diaminocyclopentane.dihydrate platinum (II) sulphate

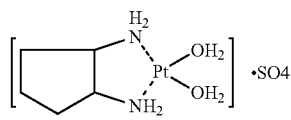

Stirring Ag$_2$SO$_4$ (625 mg, 2 mmol) in water (30 ml), 1,2-trans-diaminocyclopentane.diiodo-platinum (II) (1.10 g, 2 mmol) was added and another part of water (40 ml) was added to the reaction mixture; the mixture was stirred and heated at 40~60° C. for 4~8 h. After removing AgI deposit by suction, the filtrate was the aqueous solution of the product.

Step 7: [2-(3-diethylamino propyl)-succinato].[Cis-(1,2-trans-diaminocyclopentane)]platinum (II) phosphate

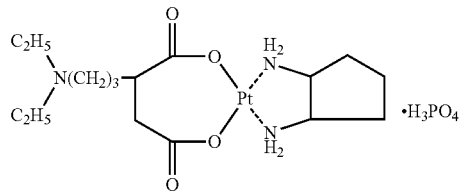

2-(3-diethylamino propyl)-succinate disodium solution was regulated to the pH 5~7 with H$_3$PO$_4$ (1M) and then aqueous 1,2-trans-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (159 mg).

$^1$HNMR (D$_2$O)(ppm): δ3.51 (m, 1H), δ3.41 (t, 2H), δ2.78 (q, 4H), δ2.70 (t, 2H), δ2.08 (br, 2H), δ1.83 (m, 2H), δ1.72 (m, 2H), δ1.49 (m, 2H), δ1.42 (m, 2H), δ1.20 (m, 1H), δ1.08 (t, 6H), δ1.02 (m, 1H).

The said compound is soluble in water. The solubility is 151 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C36.57% (theoretical 36.64%); H5.67% (theoretical 5.92%); N8.30% (theoretical 8.12%).

Embodiment 16

[2-(3-diethylamino propyl)-succinato].[Cis-(1,2-trans-cyclobutyl diamine)]platinum (II) succinate Step 1: Same as [Embodiment 3] Step 1

Step 2, 3: Same as [Embodiment 15] Step 2, 3

Step 4: 1,2-trans-cyclobutanediamine

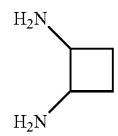

To the solution of cyclobutane (5.39 g, 100 mmol) in dichloromethane (30 ml), Br$_2$ (16.5 g, 103 mmol) was added dropwise slowly at −5~10° C. and stirred for 1~3 h, organic layer was washed with saturate sodium bicarbonate solution (10 ml×3 times) and dry with anhydrous MgSO$_4$ for 2-3 h; after removal of solvent in vacuum, 1,2-trans-dibromo cyclopentane (20.37 g) as light yellow transparent oil was obtained; and the yield is 95.19%. Elemental analysis: C22.53% (theoretical 22.43%); H2.61% (theoretical 2.80%).

1,2-trans-dibromo cyclopentane (10.65 g, 50 mmol) and 30% ammonia ethanol solution (30 ml) was added into 100 ml pressure reactor; the mixture was heated to 40~60° C. and reacted for 6~8 h; after removal of solvent in vacuum to afford 1,2-trans-cyclobutanediamine (3.723 g) as light yellow transparent oil; and the yield was 86.58%. Elemental analysis: C55.57% (theoretical 55.81%); H19.90% (theoretical 11.63%); N32.17% (theoretical 32.56%).

Step 5:
1,2-trans-cyclobutanediamine.diiodo-platinum (II)

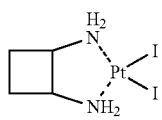

KI (6.63 g, 40 mmol) solution (50 ml) was added to potassium chloroplatinite ($K_2PtCl_4$) (2.075 g, 5 mmol) in water (50 ml), the mixture was stirred and heated to 40~60° C. away from light and oxygen for 0.5~2 h., and then 1,2-trans-cyclobutanediamine (501 mg, 5 mmol) in water (50 ml) was added; and the reaction mixture was kept under this condition for 0.5~2 h. Yellow solid product (2.429 g) was obtained by suction filtration and washing successively with water (10 ml×3 times) and diethyl ether (10 ml×3 times); the yield was 90.8%. Elemental analysis: C8.75% (theoretical 8.97%); H1.91% (theoretical 1.87%); N5.98% (theoretical 5.23%).

Step 6: 1,2-trans-cyclobutanediamine.dihydrate platinum (II) sulfate

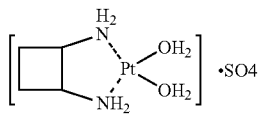

Stirring $Ag_2SO_4$ (625 mg, 2 mmol) in water (30 ml), 1,2-trans-cyclobutanediamine.diiodo-platinum (II)(1.07 g, 2 mmol) was added and another part of water (40 ml) was added to the reaction mixture under $N_2$ protection; the mixture was stirred and heated at 40~60° C. for 4-8 h. After removing AgI deposit by suction, the filtrate was the aqueous solution of the product.

Step 7: [2-(3-diethylamino propyl)-succinato].[Cis-(1,2-trans-cyclobutanediamine)]platinum (II) succinate

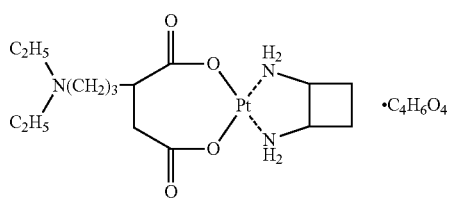

2-(3-diethylamino propyl)-succinato disodium salt solution was regulated to the pH 5~7 with $C_4H_6O_4$(1M) and then aqueous 1,2-trans-cyclobutanediamine.dihydrate platinum (II) sulphate was poured into reaction mixture under $N_2$ protection; the mixture was heated in water bath to 40~60° C. for 4-8 h, and then added 2.5 g silica into it; the mixture was stirred for 15 min and concentrated to dry, the residue was purified by column chromatography to afford the title compound (155 mg).

$^1$HNMR ($D_2O$)(ppm): δ3.52 (m, 1H), δ3.38 (d, 2H), δ2.78 (q, 4H), δ2.70 (t, 2H), δ2.08 (br, 2H), δ1.85 (m, 2H), δ1.72 (m, 2H), δ1.49 (m, 2H), δ1.44 (m, 2H), δ1.08 (t, 6H).

The said compound is soluble in water. The solubility is 186 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C35.54% (theoretical 35.29%); H5.651% (theoretical 5.69%); N8.32% (theoretical 8.24%).

Embodiment 17

[2-(3-diethylamino propyl)-succinato].[Cis-(1,2-trans-cyclopropyl diamine)]platinum (II) phosphate Step 1: Same as [Embodiment 3] Step 1

Step 2, 3: Same as [Embodiment 15] Step 2, 3

Step 4: 1,2-trans-cyclopropyl diamine.diiodo-platinum (II)

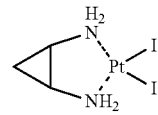

KI (6.630 g, 40 mmol) solution (50 ml) was added to potassium chloroplatinite ($K_2PtCl_4$) (2.075 g, 5 mmol) in water (50 ml), the mixture was stirred and heated to 40~60° C. away from light and oxygen for 0.5~2 h, and then 1,2-trans-cyclopropyl diamine (361 g, 5 mg, 5 mmol) in water (50 ml) was added; and the reaction mixture was kept under this condition for 0.5~2 h. Yellow solid product (2.39 g) was obtained by suction filtration and washing successively with water (10 ml×3 times) and diethyl ether (10 ml×3 times), the yield was 91.8%. Elemental analysis: C6.97% (theoretical 6.91%); H1.41% (theoretical 1.54%); N5.47% (theoretical 5.37%).

Step 5: 1,2-trans-cyclopropyl diamine.dihydrate platinum (II) sulphate

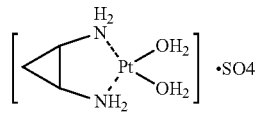

Stirring $Ag_2SO_4$ (624 mg, 2 mmol) in water (30 ml), 1,2-trans-cyclopropyl diamine.diiodo-platinum (II)(1.04 g, 2 mmol) was added and another part of water (30 ml) was added to the reaction mixture; the mixture was stirred and heated at 40~60° C. for 4~8 h. After removing AgI deposit by suction. The filtrate was the aqueous solution of the product.

Step 6: [2-(3-diethylamino propyl)-succinato].[Cis-(1,2-trans-cyclopropyl diamine)]platinum (II) phosphate

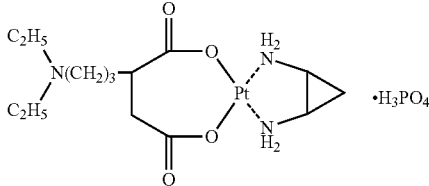

2-(3-diethylamino propyl)-succinate disodium solution was regulated to the pH 5~7 with $H_3PO_4$ (1M) and then aqueous 1,2-trans-cyclopropyl diamine.dihydrate platinum (II) sulphate was poured into reaction mixture; the mixture was heated in water bath to 40~60° C. for 4-8 h; and then added 2.5 g silica into it, the mixture was stirred for 15 min and concentrated to dry, the residue was purified by column chromatography to afford the title compound (142 mg).

$^1$HNMR ($D_2O$)(ppm): δ3.51 (m, 1H), δ3.41 (d, 2H), δ2.78 (q, 4H), δ2.70 (t, 2H), 2.10 (br, 2H), 1.87 (m, 1H), δ1.75 (m, 2H), δ1.48 (m, 2H), 1.43 (m, 1H), 1.09 (t, 6H).

The said compound is soluble in water. The solubility is 195 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C33.59% (theoretical 33.87%); H5.32% (theoretical 5.44%); N8.53% (theoretical 8.48%).

Embodiment 18

[2-(2-dimethylamine)-succinato].[Cis-1,2-ethylenediamine]platinum (II) tosylate

Step 1: Same as [Embodiment 1] Step 1

Step 2, 3: Same as [Embodiment 2] Step 2, 3

Step 4: 1,2-ethylenediamine.diiodo-platinum (II)

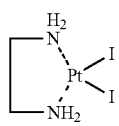

KI (6.64 g, 40 mmol) solution (40 ml) was added to potassium chloroplatinite ($K_2PtCl_4$) (2.076 g, 5 mmol) in water (50 ml), the mixture was stirred and heated to 40~60° C. away from light and oxygen for 0.5~2 h., and then 1,2-ethylenediamine (301 g, 5 mg, 5 mmol) refrigerated in water (50 ml) was added; and the reaction mixture shall be kept under this condition for 0.5~2 h. Yellow solid product (2.254 g) was obtained by suction filtration and washing successively with water (10 ml×3 times) and diethyl ether (10 ml×3 times), the yield was 89.8%. Elemental analysis: C4.77% (theoretical 4.72%); H1.41% (theoretical 1.57%); N5.41% (theoretical 5.50%).

Step 5: 1,2-ethyldiamine.dihydrate platinum (II) sulphate

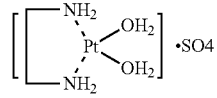

Stirring $Ag_2SO_4$ (625 mg, 2 mmol) in water (30 ml), 1,2-ethylenediamine.diiodo-platinum (II)(1.02 g, 2 mmol) was added and another part of water (40 ml) was added to the reaction mixture, the mixture was stirred and heated at 40~60° C. for 4~8 h. After removing AgI deposit by suction, the filtrate was the aqueous solution of the product.

Step 6: [2-(2-dimethylamine)-succinato].[Cis-1,2-ethylenediamine]platinum (II) tosilate

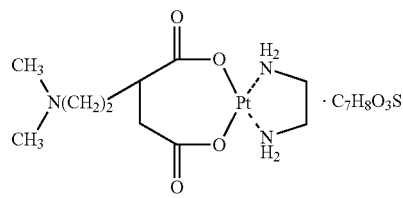

2-(3-dimethylamine)-succinate disodium solution was regulated to the pH 5~7 with p-toluenesulfonic acid ($C_7H_8O_3S$, 1M) and then aqueous 1,2-ethylenediamine.dihydrate platinum (II) sulphate was poured into reaction mixture; the mixture was heated in water bath to 40~60° C. for 4-8 h; and then added 2.5 g silica into it, the mixture was stirred for 15 min and concentrated to dry, the residue was purified by column chromatography to afford the title compound (145 mg).

$^1$HNMR ($D_2O$)(ppm): δ3.53 (m, 1H), δ3.43 (d, 2H), δ2.68 (s, 6H), δ2.55 (t, 2H), δ2.24-2.32 (br, 4H), δ1.74 (m, 2H).

The said compound is soluble in water. The solubility is 226 mg/ml. It can be easily converted into other types of organic or inorganic salts through free base. It may be but not limited to sulphate, mesylate, tartrate, succinate, acetate, citrate, tosilate, fumarate, etc. Free alkali elemental analysis: C26.96% (theoretical 27.15%); H4.52% (theoretical 4.75%); N9.32% (theoretical 9.50%).

Embodiment 19

[2-(2-diethylin aminoethyl)-succinato].[Cis-1,3-propyl diamine]platinum (II) phosphate Step 1: Same as [Embodiment 1] Step 1

Step 2, 3: Same as [Embodiment 5] Step 2, 3

Step 4: 1,3-propane diamine.diiodo-platinum (II)

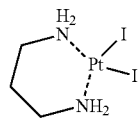

KI (6.63 g, 40 mmol) solution was added to potassium chloroplatinite ($K_2PtCl_4$) (2.073 g, 5 mmol) in water (50 ml), the mixture was stirred and heated to 40~60° C. away from light and oxygen for 0.5~2 h, and then 1,3-propane diamine (commercially available) refrigerated (372 g, 5 mg, 5 mmol) in water (50 ml) was added; and the reaction mixture was kept under this condition for 0.5~2 h. Yellow solid product (2.281 g) was obtained by suction filtration and washing successively with water (10 ml×3 times) and diethyl ether (10 ml×3 times); the yield was 87.6%. Elemental analysis: C6.77% (theoretical 6.88%); H1.79% (theoretical 1.91%); N5.43% (theoretical 5.35%).

Step 5: 1,3-propyl diamine.dihydrate platinum (II) sulphate

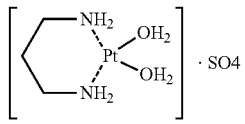

Stirring $Ag_2SO_4$(625 mg, 2 mmol) in water (30 ml), 1,3-propyl diamine.diiodo-platinum (II)(1.04 g, 2 mmol) was added and another part of water (40 ml) was added to the reaction mixture; the mixture was stirred and heated at 40~60° C. for 4~8 h. After removing AgI deposit by suction. The filtrate was the aqueous solution of the product.

Step 6: [2-(2-diethylin aminoethyl)-succinato].[Cis-1,3-propyl diamine]platinum (II) phosphate

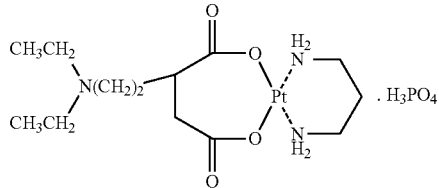

2-(3-dimethylamine)-succinate disodium (2 mmol) solution was regulated to the pH 5~7 with H3PO4 (1M) and then aqueous 1,3-propyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (149 mg).

$^1$HNMR ($D_2O$)(ppm): δ3.50 (m, 1H), δ3.39 (d, 2H), δ2.78 (q, 4H), δ2.70 (m, 2H), δ2.26 (t, 4H), δ1.70 (m, 2H), δ1.45 (m, 2H), δ1.08 (t, 6H).

The said compound is soluble in water. The solubility is 200 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C31.95% (theoretical 32.23%); H5.72% (theoretical 5.58%); N8.75% (theoretical 8.68%).

Embodiment 20

[2-(3-di-n-propylamine propyl)-succinato].[Cis-1,4-butyldiamine]platinum (II) phosphate Step 1: Same as [Embodiment 3] Step 1

Step 2, 3: Same as [Embodiment 6] Step 2, 3

Step 4: 1,4-butyldiamine.diiodo-platinum (II)

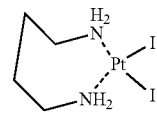

KI (6.635 g, 40 mmol) solution (50 ml) was added to potassium chloroplatinite ($K_2PtCl_4$) (2.071 g, 5 mmol) in water (50 ml), the mixture was stirred and heated to 40~60° C. away from light and oxygen for 0.5-2 h., and then 1,4-butyldiamine (commercially available) refrigerated (431 g, 5 mg, 5 mmol) in water (50 ml) was added; and the reaction mixture was kept under this condition for 0.5-2 h. Yellow solid product (2.365 g) was obtained by suction filtration and washing successively with water (10 ml×3 times) and diethyl ether (10 ml×3 times), the yield was 88.1%. Elemental analysis: C8.69% (theoretical 8.94%); H2.39% (theoretical 2.23%); N5.44% (theoretical 5.21%).

Step 5: 1,4-butyldiamine.dihydrate platinum (II) sulphate

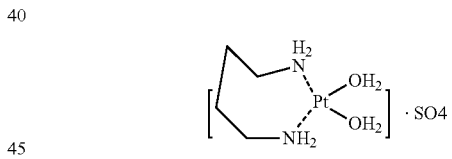

Stirring $Ag_2SO_4$ (624 mg, 2 mmol) in water (30 ml), 1,4-butyldiamine.diiodo-platinum (II) (1.072 g, 2 mmol) was added and another part of water (30 ml) was added to the reaction mixture, the mixture was stirred and heated at 40~60° C. for 4-8 h. After removing AgI deposit by suction. The filtrate was the aqueous solution of the product.

Step 6: [2-(3-di-n-propylamine ethyl)-succinato].[1,4-butyldiamine]platinum (II) phosphate

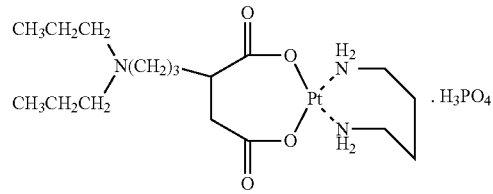

2-(2-di-n-propylamine propyl)-succinate disodium solution was regulated to the pH 5~7 with H₃PO₄(1M) and then aqueous 1,4-butyldiamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (150 mg).

¹HNMR (D₂O)(ppm): δ3.52 (m, 1H), δ3.40 (d, 2H), δ2.72 (m, 4H), δ2.52 (m, 4H), δ2.36 (t, 2H), δ2.12 (m, 2H), δ1.82 (m, 2H), δ1.55 (t, 4H), δ1.39 (m, 4H), δ1.05 (t, 6H).

The said compound is soluble in water. The solubility is 162 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C37.92% (theoretical 37.78%); H6.42% (theoretical 6.48%); N7.97% (theoretical 7.78%).

Embodiment 21

[2-(2-diethylin aminoethyl)-succinato].[Cis-1,2-di-hydroxymethyl-ethyldiamine]platinum (II) phosphate Step 1: Same as [Embodiment 1] Step 1

Step 2, 3: Same as [Embodiment 5] Step 2, 3

Step 4: 1,2-dihydroxymethyl ethyldiamine.diiodo-platinum (II)

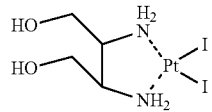

KI (6.637 g, 40 mmol) solution (50 ml) was added to potassium chloroplatinite (K₂PtCl₄) (2.073 g, 5 mmol) in water (50 ml), the mixture was stirred and heated to 40~60° C. away from light and oxygen for 0.5~2 h, and then 1,2-dihydroxymethyl ethyldiamine (601 g, 5 mg, 5 mmol) in water (50 ml) was added; and the reaction mixture was kept under this condition for 0.5~2 h. Yellow solid product (2.163 g) was obtained by suction filtration and washing successively with water (10 ml×3 times) and diethyl ether (10 ml×3 times), the yield was 79.96%. Elemental analysis: C8.65% (theoretical 8.44%); H2.39% (theoretical 2.11%); N5.03% (theoretical 4.92%).

Step 5: 1,2-dihydroxymethyl ethyldiamine.dihydrate platinum (II) sulphate

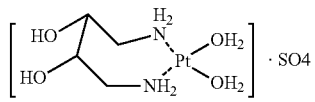

Stirring Ag₂SO₄ (624 mg, 2 mmol) in water (30 ml), 1,2-dihydroxymethylethyldiamine.diiodo-platinum (II) (1.04 g, 2 mmol) was added and another part of water (30 ml) was added to the reaction mixture; the mixture was stirred and heated at 40~60° C. for 4~8 h. After removing AgI deposit by suction. The filtrate was the aqueous solution of the title compound.

Step 6: [2-(2-diethylin aminoethyl)-succinato].[Cis-1,2-dihydroxymethylethyldiamine]platinum (II) phosphate

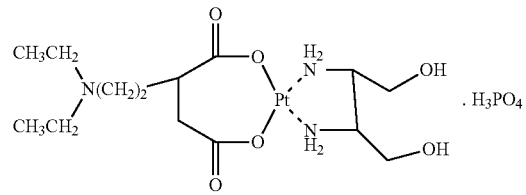

2-(2-diethylin aminoethyl)-succinate disodium solution was regulated to the pH 5~7 with H3PO4 (1M) and then aqueous 1,2-dihydroxymethylethyldiamine.dihydrate platinum (II) sulphate was poured into reaction mixture; the mixture was heated in water bath to 40~60° C. for 4-8 h; and then added 2.5 g silica into it, the mixture was stirred for 15 min and concentrated to dry, the residue was purified by column chromatography to afford the title compound (138 mg).

¹HNMR (D₂O)(ppm): δ3.50 (m, 1H), δ3.38 (d, 2H), δ3.03 (d, 4H), δ2.77-2.92 (m, 4H), δ2.67 (m, 2H), δ2.40 (t, 2H), δ1.75 (t, 2H), δ1.08 (t, 6H).

The said compound is soluble in water. The solubility is 176 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C31.76% (theoretical 31.7%); H5.62% (theoretical 5.47%); N8.17% (theoretical 7.92%).

Embodiment 22

[2-(2-dimethylamine)-succinato].[Cis-2,2-dihydroxymethyl-1,3-propyl diamine]platinum (II) phosphate Step 1: Same as [Embodiment 1] Step 1

Step 2, 3: Same as [Embodiment 2] Step 2, 3

Step 4: 2,2-dihydroxymethyl-1,3-propyl diamine.diiodo-platinum (II)

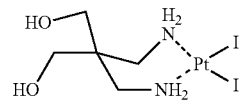

KI (6.637 g, 40 mmol) solution (40 ml) was added to potassium chloroplatinite (K₂PtCl₄) (2.0734 g, 5 mmol) in water (50 ml), the mixture was stirred and heated to 40~60° C. away from light and oxygen for 0.5~2 h, and then 2,2-dihydroxymethyl-1,3-propyl diamine (671 g, 5 mg, 5 mmol) in water (50 ml) was added; and the reaction mixture shall be kept under this condition for 0.5~2 h. Yellow solid product (2.163 g) was obtained by suction filtration and washing successively with water (10 ml×3 times) and diethyl ether (10 ml×3 times), the yield was 79.96%. Elemental analysis: C10.37% (theoretical 10.29%); H2.49% (theoretical 2.40%); N5.01% (theoretical 4.80%).

Step 5: (2,2-hydroxymethyl)-1,3-propyldiamine.dihydrate platinum (II) sulphate

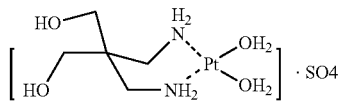

Stirring Ag$_2$SO$_4$ (624 mg, 2 mmol) in water (30 ml), 1,3-(2,2-dihydroxymethyl)-propyl diamine.diiodo-platinum (II) (1.162 g, 2 mmol) was added and another part of water (40 ml) was added to the reaction mixture; the mixture was stirred and heated at 40-60° C. for 4~8 h. After removing AgI deposit by suction. The filtrate was the aqueous solution of the title compound.

Step 6: [2-(2-dimethylamine)-succinato].[Cis-2,2-hydroxymethyl)-1,3-(propyldiamine]platinum (II) phosphate

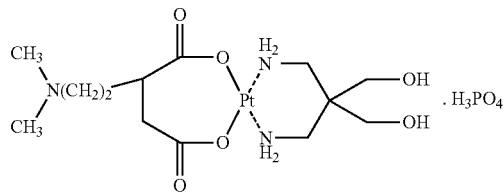

2-(2-dimethylamine)-succinate disodium solution was regulated to the pH 5~7 with H3PO4 (1M) and then aqueous (2,2-dihydroxymethyl)-1,3-propyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (135 mg).

$^1$HNMR (D$_2$O)(ppm): δ3.52 (m, 1H), δ3.42 (d, 2H), δ3.49 (s, 4H), δ2.75 (s, 6H), δ2.70 (t, 2H), δ2.57 (s, 4H), δ2.70 (m, 2H).

The said compound is soluble in water. The solubility is 205 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C30.19% (theoretical 30.23%); H5.20% (theoretical 5.23%); N8.29% (theoretical 8.14%).

Embodiment 23

[2-(2-dimethylamine)-succinato].[Cis-1,4-(trans-2,3-cyclobutyl)-butyldiamine]platinum (II) phosphate Step 1: Same as [Embodiment 1] Step 1

Step 2, 3: Same as [Embodiment 2] Step 2, 3

Step 4: 1,4-(trans-2,3-cyclobutyl)-butanediamine platinum (II)

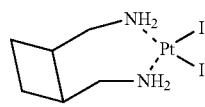

KI (6.64 g, 40 mmol) solution (40 ml) was added to potassium chloroplatinite (K$_2$PtCl$_4$) (2.075 g, 5 mmol) in water (50 ml), the mixture was stirred and heated to 40~60° C. away from light and oxygen for 0.5~2 h, and then 1,4-(trans-2,3-cyclobutyl)-butanediamine (571 g, 5 mg, 5 mmol) in water (50 ml) was added; and the reaction mixture shall be kept under this condition for 0.5~2 h. Yellow solid product (2.251 g) was obtained by suction filtration and washing successively with water (10 ml×3 times) and diethyl ether (10 ml×3 times). The yield was 79.96%. Elemental analysis: C12.61% (theoretical 12.79%); H2.45% (theoretical 2.49%); N5.11% (theoretical 4.97%).

Step 5: 1,4-(trans-2,3-cyclobutyl)-butanediamine.dihydrate platinum (II) sulphate

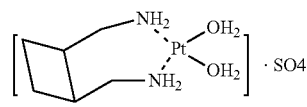

Stirring Ag$_2$SO$_4$ (624 mg, 2 mmol) in water (30 ml), trans-1,3-(2,2-hydroxymethyl)-propane diamine.diiodo-platinum (II)(1.12 g, 2 mmol) was added and another part of water (30 ml) was added to the reaction mixture; the mixture was stirred and heated at 40~60° C. for 4~8 h. After removing AgI deposit by suction. The filtrate was the aqueous solution of the title compound.

Step 6: [2-(2-dimethylamine)-succinato]. [Cis-1,4-(trans-2,3-cyclobutyl)]-butanediamine platinum (II) phosphate

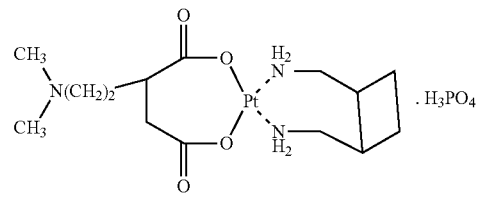

2-(2-dimethylamine)-succinate disodium solution was regulated to the pH 5~7 with H3PO4 (1M) and then 1,4-(trans-2,3-cyclobutyl)]-butanediamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (155 mg).

$^1$HNMR (D$_2$O)(ppm): δ3.52 (m, 1H), δ3.42 (d, 2H), δ2.75 (s, 6H), δ2.70 (t, 2H), δ2.23 (d, 4H), δ1.95 (m, 2H), δ1.70 (m, 2H), δ1.44 (m, 4H).

The said compound is soluble in water. The solubility is 165 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C33.59% (theoretical 33.87%); H5.31% (theoretical 5.44%); N8.65% (theoretical 8.47%).

Embodiment 24

[2-(2-diethylin aminoethyl)-succinato].[Cis-1,4-(trans-2,3-cyclobutyl)-butanediamine]platinum (II) furmarate Step 1: Same as [Embodiment 1] Step 1

Step 2, 3: Same as [Embodiment 5] Step 2, 3

Step 4, 5: Same as [Embodiment 23] Step 4, 5

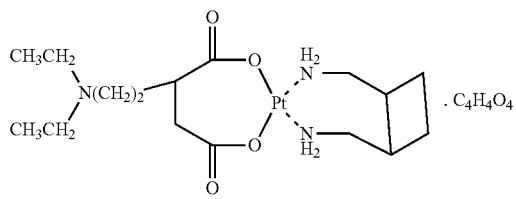

Step 6: 2-(2-diethylin aminoethyl)-succinate disodium solution was regulated to the pH 5~7 with fumaric acid ($C_4H_4O_4$, 1M) and then 1,4-(trans-2,3-cyclobutyl)-butanediamine.dihydrate platinum (II) sulphate was poured into reaction mixture; the mixture was heated in water bath to 40~60° C. for 4-8 h; and then added 2.5 g silica into it, the mixture was stirred for 15 min and concentrated to dry, the residue was purified by column chromatography to afford the title compound (153 mg).

$^1$HNMR ($D_2O$)(ppm): δ3.52 (m, 1H), δ3.42 (d, 2H), δ2.78 (m, 4H), δ2.70 (t, 2H), δ2.23 (d, 4H), δ1.89 (m, 2H), δ1.72 (m, 2H), δ1.08 (t, 6H), δ1.44 (m, 4H).

The said compound is soluble in water. The solubility is 176 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C33.66% (theoretical 33.87%); H5.35% (theoretical 5.44%); N8.61% (theoretical 8.47%).

Embodiment 25

[2-(2-diethylin aminoethyl)-succinato].[Cis-1,4-cyclohexyl diamine]platinum (II) phosphate Step 1: Same as [Embodiment 1] Step 1

Step 2, 3: Same as [Embodiment 5] Step 2, 3

Step 4: 1,4-cyclohexyl diamine.diiodo-platinum (II)

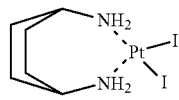

KI (6.64 g, 40 mmol) solution (40 ml) was added to potassium chloroplatinite ($K_2PtCl_4$) (2.071 g, 5 mmol) in water (50 ml), the mixture was stirred and heated to 40~60° C. away from light and oxygen for 0.5~2 h, and then 1,4-cyclohexyldiamine (572 g, 5 mg, 5 mmol) in water (50 ml) was added; and the reaction mixture was kept under this condition for 0.5~2 h. Yellow solid product (2.163 g) was obtained by suction filtration and washing successively with water (10 ml×3 times) and diethyl ether (10 ml×3 times), the yield was 76.84%. Elemental analysis: C12.74% (theoretical 12.79%); H2.45% (theoretical 2.49%); N5.17% (theoretical 4.97%).

Step 5: 1,4-cyclohexyl diamine.dihydrate platinum (II) sulphate

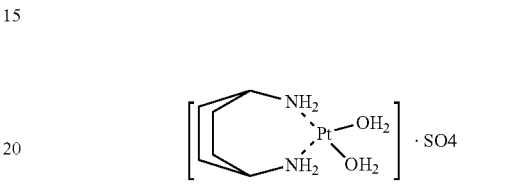

Stirring $Ag_2SO_4$ (624 mg, 2 mmol) in water (30 ml), 1,4-cyclohexyl diamine.diiodo-platinum (II) (1.125 g, 2 mmol) was added and another part of water (40 ml) was added to the reaction mixture; the mixture was stirred and heated at 40~60° C. for 4~8 h. After removing AgI deposit by suction. The filtrate was the aqueous solution of the title compound.

Step 6: [2-(2-diethylin aminoethyl)-succinato].[Cis-1,4-cyclohexyl diamine]platinum (II) phosphate

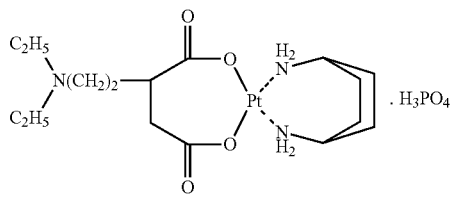

2-(2-diethylin aminoethyl)-succinate disodium solution was regulated to the pH 5~7 with H3PO4 (1M) and then aqueous 1,4-cyclohexyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (150 mg).

$^1$HNMR ($D_2O$)(ppm): δ3.52 (m, 1H), δ3.42 (d, 2H), δ2.78 (m, 4H), δ2.70 (t, 2H), 2.05 (m, 2H), δ1.72 (m, 2H), δ1.53-1.78 (m, 8H), δ1.08 (t, 6H).

The said compound is soluble in water. The solubility is 125 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C36.51% (theoretical 36.64%); H5.57% (theoretical 5.92%); N8.09% (theoretical 8.02%).

Embodiment 26

[2-(2-diethylin aminoethyl)-succinato].[Cis-1,3-(2,2-(4-oxacyclohexyl))-propyl diamine]platinum (II) phosphate Step 1: Same as [Embodiment 1] Step 1

Step 2, 3: Same as [Embodiment 5] Step 2, 3

Step 4: 1,3-(2,2-(4-oxacyclohexyl))-propyl diamine-.diiodo-platinum (II)

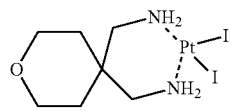

KI (6.64 g, 40 mmol) solution (50 ml) was added to potassium chloroplatinite (K$_2$PtCl$_4$) (2.071 g, 5 mmol) in water (50 ml), the mixture was stirred and heated to 40~60° C. away from light and oxygen for 0.5~2 h, and then 1,3-(2,2-(4-oxacyclohexyl))-propyl diamine (722 g, 5 mg, 5 mmol) in water (50 ml) was added; and the reaction mixture was kept under this condition for 0.5~2 h. Yellow solid product (2.547 g) was obtained by suction filtration and washing successively with water (10 ml×3 times) and diethyl ether (10 ml×3 times), the yield was 85.91%. Elemental analysis: C14.35% (theoretical 14.17%); H2.75% (theoretical 2.70%); N4.72% (theoretical 4.72%).

Step 5: 1,3-(2,2-(4-oxacyclohexyl))-propyl diamine.dihydrate platinum (II) sulphate

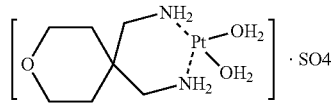

Stirring Ag$_2$SO$_4$ (623 mg, 2 mmol) in water (30 ml), 1,3-(2,2-(4-oxacyclohexyl))-propyl diamine.diiodo-platinum (II)(1.185 g, 2 mmol) was added and another part of water (40 ml) was added to the reaction mixture; the mixture was stirred and heated at 40-60° C. for 4~8 h. After removing AgI deposit by suction. The filtrate was the aqueous solution of the title compound.

Step 6: [2-(2-diethylin aminoethyl)-succinato].[Cis-1,3-(2,2-(4-oxacyclohexyl))-propyldiamine]platinum (II) phosphate

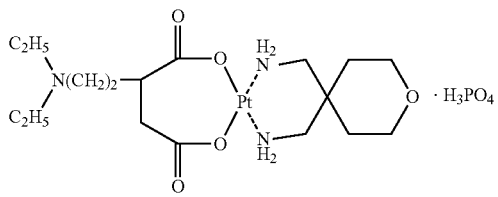

2-(2-diethylin aminoethyl)-succinate disodium (2 mmol) solution was regulated to the pH 5~7 with H3PO4 (1M) and then aqueous 1,3-(2,2-(4-oxacyclohexyl))-propyl diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (150 mg).

$^1$HNMR (D$_2$O)(ppm): δ3.70 (t, 4H), δ3.55 (m, 1H), δ3.40 (d, 2H), δ2.78 (m, 4H), δ2.70 (t, 2H), δ2.12 (s, 4H), δ1.89 (m, 2H), δ1.52 (t, 4H), δ1.08 (t, 6H).

The said compound is soluble in water. The solubility is 165 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C36.77% (theoretical 36.82%); H5.71% (theoretical 5.96%); N7.44% (theoretical 7.58%).

Embodiment 27

[2-(4-diethylamine butyl)-succinato].[Cis-diamine]platinum (II) acetate

Step 1: 2-(4-bromobutyl) diethyl succinate

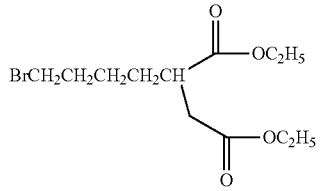

Diethyl succinate (17.26 g, 0.1 mol) and 1,4-dibromoethane (16.1 g, 0.1 mol) were placed into three 150 ml flasks. K$_2$CO$_3$ (15.13 g, 0.11 mol) and tetrabutyl ammonium bromide (155 mg) were added. The mixture was stirred and heated to 65~85° C. in oil bath for 16~24 h; suction filtration was conducted to remove solid which was washed with diethyl ether (30 ml×3 times), filtrate was consolidated; and washed with water (40 ml×3 times) then dried with MgSO$_4$ for 4~8 h; after removal of solvent, the distillate was collected for 141° C.-151° C. at vacuum 7 mmHg; the product was 9.66 g; and the yield was 31.26%.

Step 2: 2-(4-diethylamine butyl)-diethyl succinate

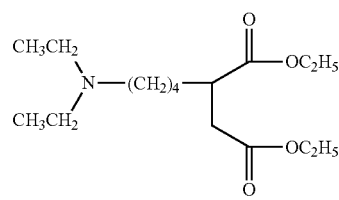

To the mixture of 4-brombutyl-diethyl succinate (123.7 g, 0.4 mol), anhydrous K$_2$CO$_3$ (55.6 g, 0.4 mol) in acetonitrile (500 ml) solution was added diethylamine (73.1 g, 1.0 mol) and the mixture was heated at 45~60° C. for 2-6 h; insoluble substance was filtered out and the filtrate was concentrated in vacuum; the residues was dissolved with 1000 ml ethyl acetate; organic phase was washed with saturate NaCl aqueous solution (250 ml×3 times) and dried over anhydrous MgSO$_4$ overnight; after removal of solvent in vacuum, light yellow oil (105.1 g) was obtained; the oil was purified by column chromatography to afford the title compound (50.71 g) and the yield was 41.6%.

Step 3: 2-(4-diethylamine butyl)-succinate disodium

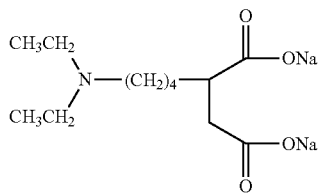

2M NaOH solution (2.5 mL) was added to 2-(3-dimethylamino propyl)-diethyl succinate (602 mg, 2 mmol) in three 20 mL flasks; and the mixture was stirred at room temperature for 45~60 h, 2-(4-diethylamine butyl) succinate disodium solution was obtained.

Step 4, 5: Same as [Embodiment 1] Step 4, 5

Step 6: [2-(4-diethylamine butyl)-succinato].[Cis-diamine]platinum (II) acetate

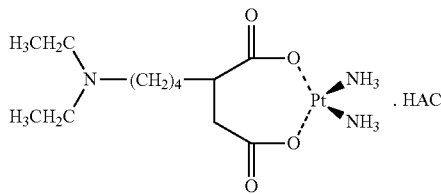

2-(4-diethylamine butyl)-succinate disodium solution was regulated the pH to 5~7 with HAC (1M) and then Cis-diamino.dihydrate platinum (II) sulphate aqueous solution was poured into reaction mixture; the mixture was heated in water bath to 40~75° C. for 4-6 h under $N_2$ protection; after filtration, reaction mixture was concentrated to a certain volume and should be at a standstill; crystalline-type product (132 mg) is obtained.

$^1$HNMR ($D_2O$)(ppm): δ3.52 (m, 1H), δ3.47 (d, 2H), δ2.79-2.67 (b, 4H), δ2.57-2.67 (b, 2H), δ1.80 (m, 2H), δ1.45 (m, 2H), δ1.24 (m, 2H), δ1.05 (t, 6H).

The free alkali and salt of the said compound is soluble in water. The solubility is 143 mg/ml. This compound can be easily converted into other types of organic or inorganic salts through dissolution and may be but not limited to sulphate, mesylate, tartrate, succinate, acetate, citrate, tosilate, fumarate, etc. Free base elemental analysis: C30.51% (theoretical 30.51%); H5.66% (theoretical 5.72%); N8.81% (theoretical 8.90%).

Embodiment 28

[2-(4-diethylamine butyl)-succinato].[Cis-1,2-ethylenediamine]platinum (II) tosilate Step 1, 2, 3: Same as [Embodiment 27] Step 1, 2, 3

Step 4, 5: Same as [Embodiment 18] Step 4, 5

Step 6: [2-(4-diethylamine butyl)-succinato].[Cis-1,2-ethylenediamine]platinum (II) tosylate

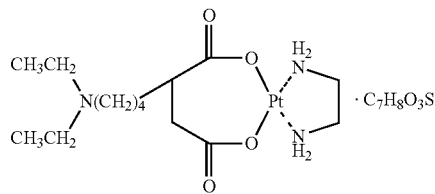

2-(3-dimethylamino propyl)-succinate disodium solution was regulated to the pH 5~7 with p-toluenesulfonic acid ($C_7H_8O_3S$, 1M) and then aqueous 1,2-ethylenediamine.dihydrate platinum (II) sulphate was poured into reaction mixture; the mixture was heated in water bath to 40~60° C. for 4-8 h; and then added 2.5 g silica into it, the mixture was stirred for 15 min and concentrated to dry, the residue was purified by column chromatography to afford the title compound (148 mg).

$^1$HNMR ($D_2O$)(ppm): δ3.51 (m, 1H), δ3.46 (d, 2H), δ2.77-2.67 (br, 4H), δ2.65-2.57 (br, 2H), δ2.25 (br, 4H), δ1.79 (m, 2H), δ1.44 (m, 2H), δ1.23 (m, 2H), δ1.05 (t, 6H).

The said compound is soluble in water. The solubility is 187 mg/ml. It can be easily converted into other types of organic or inorganic salts through free base. It may be but not limited to sulphate, mesylate, tartrate, succinate acetate, citrate, tosilate, fumarate, etc. Free alkali elemental analysis: C33.91% (theoretical 33.73%); H5.67% (theoretical 5.58%); N8.32% (theoretical 8.43%).

Embodiment 29

[2-(4-diethylamine butyl alkyl)-succinato].[Cis-(1,2-trans-cyclohexyl diaminecyclohexyl diamine)]platinum (II) phosphate Step 1, 2, 3: Same as [Embodiment 27] Step 1, 2, 3

Step 4, 5: Same as [Embodiment 9] Step 4, 5

Step 6: [2-(4-diethylamine butyl alkyl)-succinato].[Cis-(1,2-trans-cyclohexyl diamine)]platinum (II) phosphate

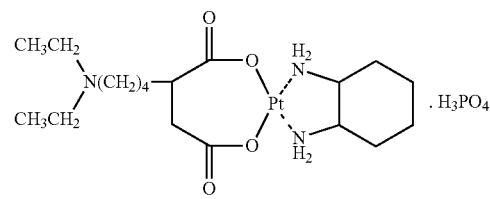

2-(4-diethylamine butyl alkyl)-succinate disodium (2 mmol) solution was regulated to the pH 5~7 with $H_3PO_4$(1M) and then aqueous trans-hexamethylene diamine.dihydrate platinum (II) sulphate was poured into reaction mixture; the mixture was heated in water bath to 40~60° C. for 4-8 h; and then added 2.5 g silica into it; the mixture was stirred for 15 min and concentrated to dry, the residue was purified by column chromatography to afford the title compound (164 mg).

$^1$HNMR ($D_2O$)(ppm): δ3.52 (m, 1H), δ3.48 (d, 2H), δ2.78-2.65 (br, 4H), δ2.67-2.56 (br, 2H), δ2.05 (br, 2H), δ1.80 (m, 4H), δ1.46 (m, 4H), δ1.25 (m, 4H), δ1.05 (t, 6H), δ1.01 (m, 2H).

The said compound is soluble in water. The solubility is 121 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C39.32% (theoretical 39.13%); H6.33% (theoretical 6.34%); N7.50% (theoretical 7.61%).

Contrast Embodiment 1

[2-formamide-succinato].[Cis-1,2-cyclohexyl diamine]platinum (II)

(D) [2-formamide-succinato].[Cis-1,2-cyclohexyl diamine]platinum (II) can be synthesized by referring to JP61249993 (especially the Embodiment 11). This compound is faint yellow crystal and almost insoluble in water. The solubility is smaller than 5 mg/ml. 259° C. is the decomposition point. Element analysis: C29.76% (theoretical 29.88%); H4.51% (theoretical 4.36%); N8.64% (theoretical 8.71%). See the structural map below:

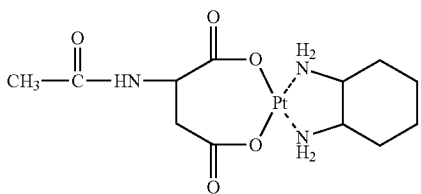

Contrast Embodiment 2

[DL-2-amino-succinato].[trans-hexamethylene diamine]platinum (II) (called ADP in short)

Step 1: DL-amino-succinato barium salt

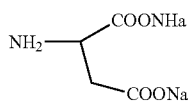

0.2M NaOH is obtained from BaOH (172 mg, 1.0 mmol) in water (5.0 mL). BaOH solution is added with DL-amino-succinato (market available) (267 mg, 2 mmol) into three 20 mL flasks and stirred at room temperature for 0.5 h. The product of DL succinato barium salt is obtained.

Step 2, 3: Same as [Embodiment 9] Step 4, 5

Step 4: DL-2-amino-succinato.trans-hexamethylene diamine platinum (II)

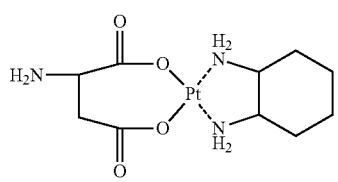

DL-amino-succinato barium salt is put into three flasks and trans-hexamethylene diamine.dihydrate platinum (II) sulfate solution (1.0 mmol) is poured into reaction solution under $N_2$ protection; the mixture is heated in water bath to 40~60° C. for reaction for 4-8 h and then added with 2.5 g column chromatography silica gel (200-300 meshes) and stirred for 15 min after drying, thus obtaining powder product. The column at the internal diameter of 100 mm is filled in with 4 cm silica gel in height and added with above powder, eluted with methanol. Consolidating eluent, part of solvent is removed through pump evaporation. When approximately 5 ml solvent is left, appropriate amount of ether is added and put at standstill for more than 12 h. The product (190 mg) of DL-2-amino-succinato.trans-hexamethylene diamine platinum (II) (called ADP in short) in faint yellow solid is obtained through vacuum filtration. The yield is 43.18%.

$^1$HNMR ($D_2O$)(ppm): δ3.71 (t, 1H), δ3.41 (d, 2H), δ2.75 (br, 2H), δ2.01 (m, 2H), δ1.92 (m, 2H), δ1.26 (m, 2H), δ1.01 (m, 2H).

The solubility of this compound is approximately 50 mg/ml. Element analysis: C27.52% (theoretical 27.27%); H4.53% (theoretical 4.32%); N9.38% (theoretical 9.55%).

Test 1: Acute Toxic Effect of Platinum Complex on Normal Mice

Kunming mice at 4~6 weeks old and at the weight of 18~22 g were taken, 50% male and 50% female. Embodiment platinum compound was dissolved with 5% glucose solution. Single intravenous administration (control: [Contrast Embodiment 1] compound and ADP) was made at different doses. Mortality and toxicity were observed after administration, totally observing 14 days, $LD_{50}$ value was calculated with Bliss method according to mortality. The results are shown in Table 1:

TABLE 1

Results of Intravenous Injection of [Contrast Embodiment 1] compound and ADP and Embodiment Platinum Compounds to Rat $LD_{50}$:

| Compound | $LD_{50}$ value (mmol/kg) | Embodiment compound | $LD_{50}$ value (mmol/kg) |
| --- | --- | --- | --- |
| Contrast Embodiment 1 compound | 0.092 | Compound 15 | 0.528 |
| ADP | 0.332 | Compound 16 | 0.623 |
| Compound 1 | 0.523 | Compound 17 | 0.581 |
| Compound 2 | 0.511 | Compound 18 | 0.532 |
| Compound 3 | 0.521 | Compound 19 | 0.454 |
| Compound 4 | 0.556 | Compound 20 | 0.513 |
| Compound 5 | 0.652 | Compound 21 | 0.681 |
| Compound 6 | 0.449 | Compound 22 | 0.452 |
| Compound 7 | 0.623 | Compound 23 | 0.512 |
| Compound 8 | 0.605 | Compound 24 | 0.525 |
| Compound 9 | 0.429 | Compound 25 | 0.459 |
| Compound 10 | 0.595 | Compound 26 | 0.526 |
| Compound 11 | 0.571 | Compound 27 | 0.557 |
| Compound 12 | 0.602 | Compound 28 | 0.612 |
| Compound 13 | 0.542 | Compound 29 | 0.698 |
| Compound 14 | 0.467 | | |

$LD_{50}$ values of above compounds 1-29 vs. $LD_{50}$ values of Contrast Embodiment 1 and ADP, $P < 0.01$.

Conclusion: The acute toxicity of the compounds at the same molar concentration in the Embodiment is much smaller than [Contrast Embodiment 1] compound and also obviously smaller than ADP.

Test 2: Cell Toxic Effects of Platinum Compound on Tumor Cell

The toxic action of platinum compound was observed on tumor cells by MTT colorimetric method and compared with the existing technology of [Contrast Embodiment 1] compound and ADP. Several kinds of tumor cells in exponential growth phase were prepared into single cell suspension, inoculated on 96 pore plat at the density of $4 \times 10^4$/hole, cultivated for 24 hours to enable to adhere to wall with 1640 culture medium containing 10% fetal calf serum (complete medium) at 37° C.; the final culture volume was 100 μl. Cell morphology was observed after culture for 24 hours. For the dosage of platinum compounds, since $IC_{50}$ values of cells are different, the following concentrations are determined through pretest: appropriate adjustment on 1000, 300, 100, 30, 10, and 3.0 μg/ml for [Contrast Embodiment 1] compound; 200, 60, 20, 0.6 μg/ml for ADP; and Embodiment platinum compounds are appropriately adjusted depending on the sensitivity to each cell. The results are shown in Table 2-8 below:

TABLE 2

Cytotoxin ($IC_{50}$) of Different Test Platinum Compounds to Different Cell Lines
The $IC_{50}$ (n = 6) of Chemotherapeutic Drugs to Different Cell Lines

| | $IC_{50}$(mM) | | | | |
|---|---|---|---|---|---|
| Cell lines | ADP | Contrast Embodiment 1 | Compound 1 | Compound 2 | Compound 3 |
| Breast cancer MCF-7 | 0.073 | 0.632 | 0.006 | 0.011 | 0.052 |
| Breast cancer MCF-7 | 0.156 | 0.425 | | | |
| Cisplatin resistance strain | | | 0.103 | 0.047 | 0.021 |
| Lung cancer A549 | 0.145 | 0.436 | 0.015 | 0.133 | 0.052 |
| Lung cancer H292 | 0.061 | 0.253 | 0.041 | 0.021 | 0.0043 |

TABLE 3

The Cytotoxicity ($IC_{50}$) of Different Tested Platinum Compounds to Different Cell Lines
The $IC_{50}$ (n = 6) of chemotherapeutic drugs to different cell lines

| | $IC_{50}$(mM) | | | | |
|---|---|---|---|---|---|
| Cell lines | ADP | Contrast Embodiment 1 | Compound 4 | Compound 5 | Compound 6 |
| Breast cancer MCF-7 | 0.073 | 0.632 | 0.011 | 0.017 | 0.043 |
| Breast cancer MCF-7 | 0.156 | 0.425 | | | |
| Cisplatin resistance strain | | | 0.134 | 0.041 | 0.026 |
| Lung cancer A549 | 0.145 | 0.436 | 0.013 | 0.107 | 0.059 |
| Lung cancer H292 | 0.061 | 0.253 | 0.033 | 0.028 | 0.0046 |

TABLE 4

Cytotoxicity ($IC_{50}$) of different test platinum compounds to different cell lines
The $IC_{50}$ (n = 6) of chemotherapeutic drugs to different cell lines

| | $IC_{50}$(mM) | | | | | | |
|---|---|---|---|---|---|---|---|
| Cell lines | ADP | Contrast Embodiment 1 | Compound 7 | Compound 8 | Compound 9 | Compound 10 | Compound 11 |
| Pulmonary epithelial cell BEAS-2B | 0.107 | 0.433 | 0.032 | 0.003 | 0.017 | 0.025 | 0.045 |
| Lewis lung cancer | 0.162 | 0.545 | 0.058 | 0.04 | 0.084 | 0.028 | 0.051 |
| Colon cancer SW480 | 0.098 | 0.615 | 0.081 | 0.035 | 0.062 | 0.005 | 0.022 |
| Lung cancer H292 | 0.061 | 0.353 | 0.006 | 0.043 | 0.026 | 0.024 | 0.013 |

TABLE 5

The cytotoxicity ($IC_{50}$) of different tested platinum compounds to different cell lines
The $IC_{50}$ (n = 6) of chemotherapeutic drugs to different cell lines

| | $IC_{50}$(mM) | | | | | | |
|---|---|---|---|---|---|---|---|
| Cell lines | ADP | Contrast Embodiment 1 | Compound 12 | Compound 13 | Compound 14 | Compound 15 | Compound 16 |
| Pulmonary epithelial cell BEAS-2B | 0.107 | 0.433 | 0.057 | 0.012 | 0.008 | 0.015 | 0.045 |
| Lewis lung cancer | 0.162 | 0.545 | 0.069 | 0.032 | 0.037 | 0.051 | 0.033 |
| Colon cancer SW480 | 0.098 | 0.615 | 0.072 | 0.095 | 0.051 | 0.032 | 0.084 |
| Lung cancer H292 | 0.061 | 0.353 | 0.061 | 0.057 | 0.009 | 0.145 | 0.008 |

TABLE 6

The cytotoxicity (IC$_{50}$) of different test platinum compounds to different cell lines
The IC$_{50}$ (n = 6) of chemotherapeutic drugs to different cell lines

| | IC$_{50}$(mM) | | | | | | |
|---|---|---|---|---|---|---|---|
| Cell lines | ADP | Contrast Embodiment 1 | Compound 17 | Compound 18 | Compound 19 | Compound 20 | Compound 21 |
| Testis cell ST | 0.187 | 0.239 | 0.051 | 0.010 | 0.012 | 0.022 | 0.143 |
| Gastric cancer MGC803 | 0.160 | 0.525 | 0.013 | 0.121 | 0.117 | 0.066 | 0.109 |
| Esophagus cancer ECA109 | 0.098 | 0.467 | 0.072 | 0.062 | 0.008 | 0.013 | 0.084 |
| Lung cancer H292 | 0.061 | 0.365 | 0.031 | 0.031 | 0.102 | 0.059 | 0.021 |

TABLE 7

The cytotoxicity (IC$_{50}$) of different tested platinum compounds to different cell lines
The IC$_{50}$ (n = 6) of chemotherapeutic drugs to different cell lines

| | IC$_{50}$(mM) | | | | | | |
|---|---|---|---|---|---|---|---|
| Cell lines | ADP | Contrast Embodiment 1 | Compound 22 | Compound 23 | Compound 24 | Compound 25 | Compound 26 |
| Testis cell ST | 0.187 | 0.239 | 0.052 | 0.018 | 0.012 | 0.102 | 0.044 |
| Gastric cancer MGC803 | 0.160 | 0.525 | 0.015 | 0.146 | 0.119 | 0.096 | 0.035 |
| Esophagus cancer ECA109 | 0.163 | 0.467 | 0.017 | 0.102 | 0.071 | 0.116 | 0.032 |
| Lung cancer H292 | 0.061 | 0.365 | 0.065 | 0.051 | 0.025 | 0.106 | 0.047 |

TABLE 8

The cytotoxicity (IC$_{50}$) of different tested platinum compounds to different cell lines
The IC$_{50}$ (n = 6) of chemotherapeutic drugs to different cell lines

| | IC$_{50}$(mM) | | | | |
|---|---|---|---|---|---|
| Cell lines | ADP | Contrast Embodiment 1 | Compound 27 | Compound 28 | Compound 29 |
| Testis cell ST | 0.187 | 0.239 | 0.060 | 0.138 | 0.005 |
| Gastric cancer MGC803 | 0.160 | 0.525 | 0.053 | 0.162 | 0.007 |
| Esophagus cancer ECA109 | 0.163 | 0.467 | 0.050 | 0.056 | 0.006 |
| Lung cancer H292 | 0.061 | 0.365 | 0.058 | 0.099 | 0.003 |

It is observed from Tables 2-8 that the compounds in the present invention have stronger cytotoxic effects comparing with ADP and [Contrast Embodiment 1] compounds.

Test 3: In Vivo Antitumor Activity Research of Platinum Compounds (1) Male nude mice 4~6 weeks old at the weight of 17~20 g was inoculated in armpit of the right forearm with 0.1 ml colon cancer SW480 cell line single-cell suspension, the inoculation concentration 1×10$^7$/ml, randomly grouped 24 hours after inoculation, 10 mice a group; each group was intravenously administered with 30 mg/kg ADP (based on platinum) as positive control group, (due to the toxicity of [Contrast Embodiment 1] compound and lower in vitro anti-tumor activity, in vivo anti-tumor activity research has not been conducted), isometric normal saline (negative control group), and Embodiment 1-13 compound groups respectively, administered continuously (10 mg, based on platinum), delivered drug once a week, totally 4 times, and all are intraperitoneal injections; subcutaneous tumor is taken out for weighing after 4 weeks and tumor inhibition rate is calculated (see Table 9). The calculation formula of tumor inhabitation rate is:

$$\text{Tumor inhibition rate \%} = \frac{\text{Average tumor weight of control group} - \text{average tumor weight of medicated group}}{\text{Average tumor weight of control group}} \times 100$$

TABLE 9

Results of research on anti-colon cancer SW480 activity of target compounds

| Compound | Size of animal (set) | Dose (mg (platinum)/kg) | Tumor inhibition rate (%) (x ± SD) |
|---|---|---|---|
| ADP | 10 | 30 | 45.3 ± 11.21 |
| Compound 1 | 10 | 10 | 55.1 ± 11.48 |
| Compound 2 | 10 | 10 | 55.5 ± 10.37 |
| Compound 3 | 10 | 10 | 49.6 ± 9.87 |
| Compound 4 | 10 | 10 | 50.1 ± 10.38 |
| Compound 5 | 10 | 10 | 46.7 ± 9.51 |
| Compound 6 | 10 | 10 | 49.1 ± 9.35 |
| Compound 7 | 10 | 10 | 53.5 ± 6.65 |
| Compound 8 | 10 | 10 | 54.3 ± 9.84 |

TABLE 9-continued

Results of research on anti-colon cancer SW480 activity of target compounds

| Compound | Size of animal (set) | Dose (mg (platinum)/kg) | Tumor inhibition rate (%) (x ± SD) |
|---|---|---|---|
| Compound 9 | 10 | 10 | 44.8 ± 10.8 |
| Compound 10 | 10 | 10 | 55.1 ± 9.07 |
| Compound 11 | 10 | 10 | 46.3 ± 9.88 |
| Compound 12 | 10 | 10 | 46.8 ± 9.17 |
| Compound 13 | 10 | 10 | 56.3 ± 6.81 |

(2) Female nude mice 4~6 weeks old at the weight of 17~20 g were inoculated with 0.1 ml breast cancer MCF-7 tumor cell line single-cell suspension at the concentration of $1 \times 10^7$/ml at subcutaneous position of back close to armpit, randomly grouped 2 weeks after inoculation, 10 mice a group; each group is intravenously administered with 30 mg (based on platinum)/kg ADP (positive control group), isometric normal saline (negative control group), and 10 mg/kg Embodiment 14-29 compound groups respectively; administered once a week, totally 4 times, and all are intraperitoneal injections; subcutaneous tumor is taken out for weighing 4 weeks later and tumor inhibition rate is calculated (see Table 10).

TABLE 10

Results of research on anti-breast cancer MCF-7 activity of target compounds

| Compound | Size of animal (set) | Dose (mg (platinum)/kg) | Tumor inhibition rate (9%) (x ± SD) |
|---|---|---|---|
| ADP | 10 | 30 | 68.3 ± 10.27 |
| Compound 14 | 10 | 10 | 70.1 ± 11.55 |
| Compound 15 | 10 | 10 | 73.5 ± 12.31 |
| Compound 16 | 10 | 10 | 70.4 ± 10.81 |
| Compound 17 | 10 | 10 | 82.5 ± 11.34 |
| Compound 18 | 10 | 10 | 71.8 ± 12.01 |
| Compound 19 | 10 | 10 | 65.3 ± 9.15 |
| Compound 20 | 10 | 10 | 66.7 ± 10.61 |
| Compound 21 | 10 | 10 | 68.3 ± 10.88 |
| Compound 22 | 10 | 10 | 70.8 ± 10.12 |
| Compound 23 | 10 | 10 | 85.1 ± 10.37 |
| Compound 24 | 10 | 10 | 69.3 ± 10.13 |
| Compound 25 | 10 | 10 | 66.9 ± 9.49 |
| Compound 26 | 10 | 10 | 76.4 ± 14.85 |
| Compound 27 | 10 | 10 | 79.2 ± 11.15 |
| Compound 28 | 10 | 10 | 76.4 ± 9.78 |
| Compound 29 | 10 | 10 | 82.2 ± 10.82 |

Preparation Example 1

Preparation of Injection

Prescription 1

| Compound phosphate in Embodiment 3 | 50 g |
|---|---|
| Glucose | 10 g |
| Add water for injection to produce 1000 pieces | 1000 ml |

Process: 10 g compound phosphate in Embodiment 3 and 50 g glucose were dissolved in 1000 ml injection water at normal temperature in 2000 ml glassware; after filtration with 0.22 nm microporous membrane, the filtration was charged into 1 ml ampoule to obtain the product at the specification of 10 mg/ml.

Prescription 2

| Compound mesylate in Embodiment 6 | 10 g |
|---|---|
| Glucose | 50 g |
| Add water for injection to produce 1000 pieces | 1000 ml |

Process: 10 g compound mesylate in Embodiment 6 and 50 g glucose was dissolved into 1000 ml injection water at normal temperature in 1000 ml glassware; after filtration with 0.22 μm microporous membrane, the filtration was charged into 2 ml penicillin bottle to afford the product at the specification of 10 mg/bottle.

Preparation Example 2

Preparation of Refrigerated Powder for Injection

Prescription 1

| Compound mesylate in Embodiment 6 | 10 g |
|---|---|
| Mannitol | 50 g |
| Add water for injection to produce 1000 pieces | 1000 ml |

Process: 10 g compound in Embodiment 6 and 50 g Mannitol were dissolved into 1000 ml injection water at normal temperature in 1000 ml glassware; after filtration with 0.22 μm microporous membrane, the filtration was charged into 2 ml penicillin bottle, 1 ml solution in each bottle, and then refrigerated to obtain the product at the specification of 10 mg/bottle.

Prescription 2

| Compound citrate in Embodiment 13 | 20 g |
|---|---|
| Mannitol | 50 g |
| Add water for injection to produce 1000 pieces | 1000 ml |

Process: 20 g compound citrate in Embodiment 13 and 50 g Mannitol were dissolved into 1000 ml injection water at normal temperature in 1000 ml glassware; after filtration with 0.22 μm microporous membrane, the filtration was charged into 2 ml penicillin bottle, 1 ml solution in each bottle, and then refrigerated and dried to obtain the product at the specification of 20 mg/bottle.

Prescription 3

| Compound phosphate in Embodiment 22 | 50 g |
|---|---|
| Add water for injection to produce 1000 pieces | 1000 ml |

Process: 50 g compound phosphate in Embodiment 22 was dissolved into 1000 ml injection water at normal temperature in 1000 ml glassware; after filtration with 0.22 μm microporous membrane, the filtration was charged into 2 ml penicillin bottle, 1 ml solution in each bottle, and then refrigerated and dried to obtain the product at the specification of 50 mg/bottle.

The invention claimed is:

1. A platinum compound as expressed in formula A and its pharmaceutically acceptable salt, solvate, isomer, or precursor thereof;

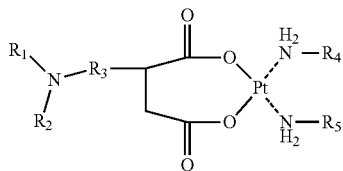

(A)

wherein:
- R₁ and R₂ are the same or different, selected from hydrogen, alkyl, naphthenic base, alkoxy alkyl, alkylamino alkyl, heterocycle, alkenyl, and alkynyl respectively; wherein above alkyl, naphthenic base, alkoxy alkyl, alkyl amino alkyl, heterocycle, alkenyl, and alkynyl are unsubstituted or optionally substituted; R₁ and R₂ may form saturated or unsaturated carboncycle or heterocycle with the atom connected, which may be unsubstituted or optionally substituted; provided that the ring that formed by R₁, R₂ or R₁ and R₂ contains unsaturated bond, the atom of the unsaturated bond cannot be directly connected with nitrogen atom;
- R₃ is selected from alkyl, naphthenic base and —R₃₁—O—R₃₂—; wherein R₃₁ and R₃₂ are independently selected from bond or alkyl; R₃₁ is connected with nitrogen atom; wherein above alkyl or naphthenic base is unsubstituted or optionally substituted;
- R₄ and R₅ are the same or different, selected from: hydrogen, hydroxyl, alkyl, naphthenic base, alkoxy, alkoxy alkyl, alkylamino alkyl, heterocycle, alkenyl, or alkynyl respectively; wherein above alkyl, alkenyl, alkynyl, naphthenic base, alkoxy alkyl, alkylamino alkyl and heterocycle may be unsubstituted or optionally substituted;
- R₄, R₅ and the atoms they connected maybe together form a closed ring, which may be four-membered, five-membered, six-membered, seven-membered or eight-membered ring; the above ring is optionally condensed with other rings and optionally substituted.

2. A platinum compound according to claim 1, wherein R₁ and R₂ are selected from hydrogen, C₁₋₈ alkyl, C₃₋₆ naphthenic base, alkoxy alkyl, alkyl amino alkyl, or heterocycle respectively; R₃ is selected from C₁₋₁₀ alkyl and C₃₋₆ naphthenic base; R₄ and R₅ are selected from hydrogen, hydroxyl, C₁₋₈ alkyl, C₃₋₆ naphthenic base, alkoxy, alkoxy alkyl, or heterocycle.

3. The platinum compound according to claim 1 or claim 2, the structure is shown in formula B:

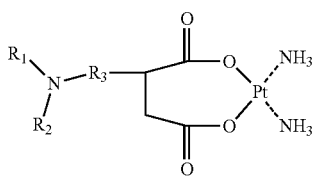

(B)

wherein: R₁, R₂ and R₃ are as described in claim 1.

4. A platinum compound according to claim 1, wherein R₁ and R₂ are independently selected from hydrogen, methyl, ethyl and propyl group; or the closed ring formed by R₁, R₂ and the atoms connected thereof is pyrrolidinyl or piperidyl; R₃ is methyl, ethyl, propyl, isopropyl, normal-butyl, isobutyl, tertiary butyl or pentyl; R₄ and R₅ are hydrogens.

5. A platinum compound according to claim 1, wherein the structure thereof is shown in formula C:

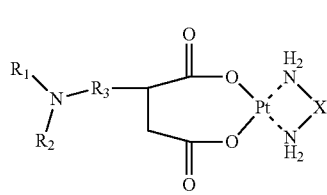

(C)

wherein,

is selected from:

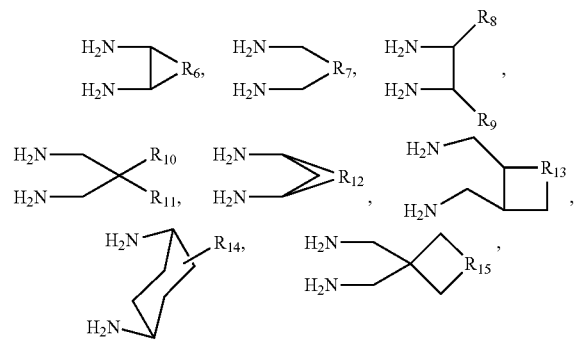

and above structures are optionally substituted;
- R₁ and R₂ are the same or different, selected from hydrogen, alkyl, naphthenic base, alkoxy alkyl, alkyl amino alkyl, heterocycle, alkenyl, or alkynyl; wherein above alkyl, alkoxy alkyl, alkyl amino alkyl, heterocycle, alkenyl, or alkynyl may be unsubstituted or optionally substituted; R₁ and R₂ may form saturated or unsaturated carboncycle or heterocycle with the atom connected; and the ring formed may be unsubstituted or optionally substituted; provided that the ring formed by R₁, R₂ or R₁ and R₂ contains unsaturated bond, the atom of the unsaturated bond cannot be directly connected with nitrogen atom;
- R₃ is selected from alkyl, naphthenic base and —R₃₁—O—R₃₂—; R₃₁ and R₃₂ are independently selected from bond or alkyl; R₃₁ is connected with nitrogen atom; the above alkyl or naphthenic base may be unsubstituted or optionally substituted;
- R₆ is selected from $(CH_2)_a$, wherein a=1-6; wherein some —CH₂— may be substituted by —O—. One or more hydrogen of $(CH_2)_a$ may be substituted by fluorine, alkyl, hydroxyl or alkoxy.
- R₇ is selected from $(CH_2)_b$, wherein b=0-3; wherein some —CH₂— may be substituted by —O—, and one or more hydrogen of $(CH_2)_b$ may be substituted by halogen, alkyl, hydroxyl, hydroxyalkyl or alkoxy, heterocycle;
- R₈ and R₉ are selected from hydrogen, halogen, hydroxyl, hydroxyalkyl, alkyl, alkoxy and heterocycle; R₈ and R₉ may be the same or different;

$R_{10}$ and $R_{11}$ are selected from hydrogen, halogen, hydroxyalkyl, alkyl, alkoxy, heterocycle, $R_{10}$ and $R_{11}$ may be the same or different;

$R_{12}$ is selected from $(CH_2)_m$, wherein m=2-4, wherein some —$CH_2$— may be substituted by —O—. One or more hydrogen of $(CH_2)_m$ may be substituted by halogen, alkyl, hydroxyl or alkoxy, heterocycle;

$R_{13}$ is —$CH_2$— or —O—;

$R_{14}$ is selected from hydrogen, halogen, alkyl, alkoxy, heterocycle, hydroxyalkyl or hydroxyl;

$R_{15}$ is selected from $(CH_2)_n$, —$(CH_2)_n$—O—, —$CH_2$—O—$CH_2$—; wherein n=1-3 one or more hydrogen of —$CH_2$—O—$CH_2$— may be substituted by alkyl, alkoxy, heterocycle, hydroxyl, or hydroxyalkyl.

6. A platinum compound according to claim 5, which has the following structure:

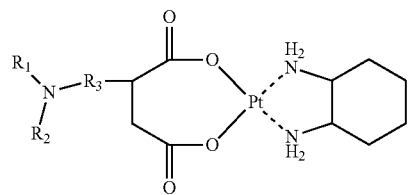
(D1)

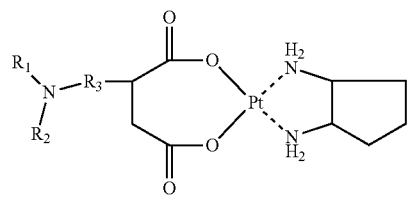
(D2)

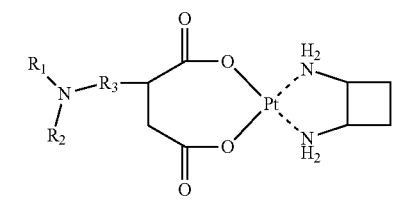
(D3)

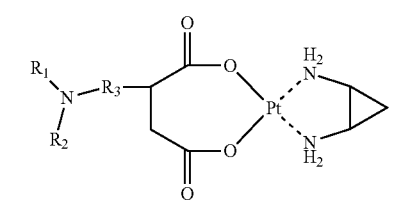
(D4)

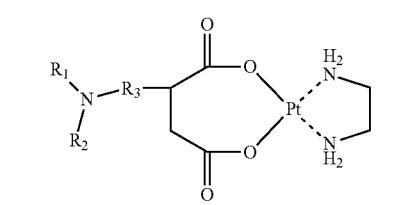
(E1)

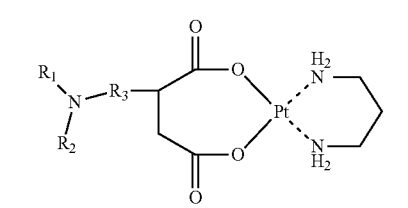
(E2)

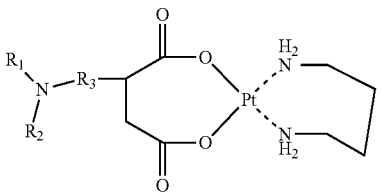
(E3)

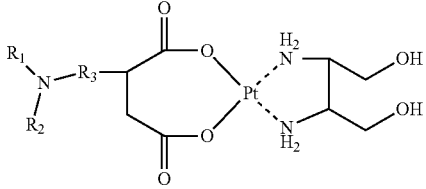
(F)

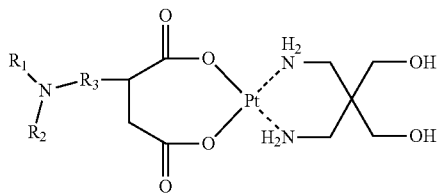
(G)

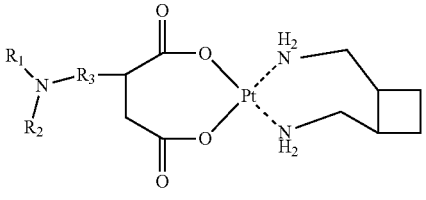
(H)

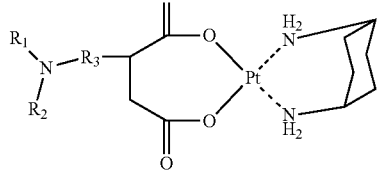
(I)

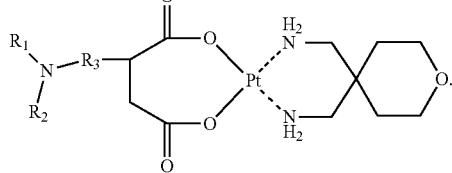
(J)

7. A compound or its pharmaceutical acceptable salt, solvate, isomer or precursor thereof according to claim 1, wherein the compounds are selected from:

Compound 1: [2-(2-methylamino ethyl)-succinato].[Cis-diamine]platinum (II);

Compound 2: [2-(2-dimethylamino ethyl)-succinato].[Cis-diamine]platinum (II);

Compound 3: [2-(3-dimethylamino propyl)-succinato].[Cis-diamine]platinum (II);

Compound 4: [2-(3-amino propyl)-succinato].[Cis-diamine]platinum (II);

Compound 5: [2-(2-diethylamino ethyl)-succinato].[Cis-diamine]platinum (II);

Compound 6: [2-(3-di-n-propylamino propyl)-succinato].[Cis-diamine]platinum (II);

Compound 7: [2-(3-(1-piperidyl)-propyl)-succinato].[Cis-diamine]platinum (II);

Compound 8: [2-(3-(1-pyrrolidyl)-propyl)-succinato].[Cis-diamine]platinum (II)

Compound 9: [2-(2-aminoethyl)-succinato].[Cis-(1,2-trans-cyclohexyl diamine)]platinum Compound 10: [2-(2-diethylamino ethyl)-succinato].[Cis-(1,2-trans-cyclohexyl diamine)]platinum (II);

Compound 11: [2-(3-dimethylamino propyl)-succinato].[Cis-(1,2-trans-cyclohexyl diamine)]platinum (II);

Compound 12: [2-(2-ethylamino ethyl)-succinato].[Cis-(1,2-trans-cyclohexyl diamine)]platinum (II);

Compound 13: [2-(3-(1-piperidyl) propyl)-succinato].[Cis-(1,2-trans-cyclohexyl diamine)]platinum (II);

Compound 14: [2-(3-di-n-propylamino propyl)-succinato].[Cis-(1,2-trans-cyclohexyl diamine)]platinum (II);

Compound 15: [2-(3-diethylamino propyl)-succinato].[Cis-(1,2-trans-cyclopentyl diamine)]platinum (II);

Compound 16: [2-(3-diethylamino propyl)-succinato].[Cis-(1,2-trans-cyclobutyl diamine)]platinum (II);

Compound 17: [2-(3-diethylamino propyl)-succinato].[Cis-(1,2-trans-cyclopropyl diamine)]platinum (II);

Compound 18: [2-(2-dimethylaminoethyl)-succinato].[Cis-1,2-ethyldiamine]platinum (II);

Compound 19: [2-(2-dimethylaminoethyl)-succinato].[Cis-1,3-propyl diamine]platinum (II);

Compound 20: [2-(3-di-n-propylaminoethyl)-succinato].[Cis-1,4-butanediamine]platinum (II);

Compound 21:[2-(2-diethylaminoethyl)-succinato].[Cis-1,2-(1,2-dihydroxymethyl)-ethyldiamine]platinum (II);

Compound 22: [2-(2-dimethylaminoethyl)-succinato].[Cis-1,3-(2,2-dihydroxytoluene)-propyl diamine]platinum (II);

Compound 23:[2-(2-dimethylaminoethyl)-succinato].[Cis-1,4-(trans-2,3-cyclobutyl)-butyldiamine]platinum (II);

Compound 24:[2-(2-diethylaminoethyl)-succinato].[Cis-1,4-(trans-2,3-cyclobutyl)-butanediamine]platinum (II);

Compound 25: [2-(2-diethylaminoethyl)-succinato].[Cis-1,4-cyclohexyl diamine]platinum (II);

Compound 26: [2-(2-diethylaminoethyl)-succinato].[Cis-1,3-(2,2-(4-oxacyclohexyl))-propyl diamine]platinum (II);

Compound 27: [2-(4-diethylamino butyl)-succinato].[Cis-diamine]platinum (II)acetate;

Compound 28: [2-(4-diethylamino butyl)-succinato].[Cis-1,2-ethylenediamine]platinum (II) toluenesulfonate;

Compound 29: [2-(4-diethylamino butyl)-succinato].[Cis-(1,2-trans-cyclohexyl diamine)]platinum (II)phosphate.

8. The compound according to claim 1, wherein the said compound is in the form of pharmaceutically acceptable salt; pharmaceutically acceptable salts are nitrate, carbonate, sulphate, phosphate, mesylate, trifluoromethanesulfonic salt, tosilate, benzene sulfonate, acetate, fumarate, tartrate, oxalate, maleate, malate, succinate, lactate, citrate, glutamate, or aspartate.

9. A pharmaceutical composition, containing the compound in claim 1 and pharmaceutically acceptable carrier and/or excipient; wherein the composition may be in any appropriate dosage form; and it may or may not contain one or more of other drugs fit for the treatment of cancer.

10. The pharmaceutical composition according to claim 9, wherein said pharmaceutical composition contains 0.01%-100% (weight) of one or multiple compounds of the present invention.

11. A preparation method for the compounds in claim 1, comprising the following steps:

(1) adding potassium chloroplatinite into water and stirring the mixture to form solution at room temperature; after dissloving potassium iodide in water, putting it into above potassium chloroplatinite solution to react under nitrogen away from light and oxygen in water bath condition;

(2) dissolving $R_4NH_2$ in water, which is then added dropwise into the reaction liquid in step (1), and reacting the mixture in water bath condition;

(3) after cooling down above reaction mixture below room temperature, dissolving $R_5NH_2$ in water, which is then added dropwise into the reaction mixture in step (2) to react in water bath; generating yellow deposit in large quantity in the mixture; after cooling down the mixture below room temperature; obtaining diiodo diamine platinum (II) through suction filtration and washing;

(4) adding $Ag_2SO_4$ into water and stiffing it; then adding the above diiodo diamine platinum (II) into reaction liquid of $Ag_2SO_4$ aqueous solution, after adding water into it to obtaom a mixture, reacting the mixture in water bath condition away from light and oxygen under nitrogen, and obtaining dihydrol diamine platinum (II).sulphate by suction filtration;

(5) putting diethyl succinate, Br—$R_3$—Br, $K_2CO_3$ and tetrabutylammonium bromide into flask and stirring it to obtain a mixture, heating the mixture for reaction; after removal of solid by suction filtration, washing the solid and combining the filtrate, then washing the organic phase and drying it, collecting the distillate after removal of solvent by reduced pressure distillation;

(6) putting 2-Br—$R_3$-diethyl succinate, anhydrous $K_2CO_3$ and acetonitrile into a flake and stiffing to obtain a reaction mixture; adding $R_1$—NH—$R_2$ into the reaction mixture, and proceeding a reaction under heating; filtering out insoluble substance of the mixture; pumping dry the filtrate and dissolving the residue in organic solvent; washing the organic phase with aqueous solution and drying it; after removal of solvent under reduced pressure; obtaining the product and purifying it;

(7) adding NaOH solution into the product in step (6) and stiffing it at room temperature;

(8) after adjusting the pH of the product in step (7) with acid solution, adding the product in above step (4) into it, then heating the mixture for reaction to afford the platinum compound of the present invention.

12. A preparation method for any one of the compounds in claims 5-6, including the following steps:

(1) adding potassium chloroplatinite into water and stiffing it at room temperature; then adding potassium iodide solution of water into above potassium chloroplatinite solution, and proceeding a reaction under nitrogen away from light and oxygen in water bath;

(2) adding bidentate ammonia $NH_2$—X—$NH_2$ aqueous solution dropwise into the reaction mixture in step (1) to react in water bath, and affording yellow deposit in great quantity; after cooling down the mixture below room temperature, obtaining bidentatediiodo diamine platinum (II) by suction filtration and washing;

(3) adding $Ag_2SO_4$ into water and stiffing it to obtain a reaction mixture, then putting above bidentatediiodo diamine platinum (II) into the reaction mixture and then adding water_into it; after making the obtained mixture to react under nitrogen away from light and oxygen in a water bath, obtaining dihydrol diamine platinum (II) .sulphate after suction filtration;

(4) putting diethyl succinate, Br—$R_3$—Br, $K_2CO_3$ and tetrabutylammonium bromide into a flask and stirring it to obtain a mixture, heating the mixture for reaction; after removing the solid by suction filtration and washing it, combining the filtrates, washing the organic phase_and drying it, then collecting the distillate after removal of solvent by reduced pressure distillation;

(5) stirring the mixture of 2-Br—$R_3$-diethyl succinate, anhydrous $K_2CO_3$ and acetonitrile to provide a reaction mixture; then adding $R_1$—NH—$R_2$ into the reaction mixture and reacting the mixture under heating; filtering out insoluble substance of the mixture; after pumping dry the filtrate, adding organic solvent for dissolution; washing the organic phase with aqueous solution and drying it; after removal of solvent under reduced pressure, obtaining the product_and purifying it;

(6) adding NaOH solution into the product in step (5) and stirring it at room temperature;

(7) after treating the product in step (6) with acid solution, adding the product in above step (3) into it, and heating the mixture for reaction to afford the platinum compound of the present invention.

13. An usage of the compounds, their pharmaceutically acceptable salts, solvates, isomers or precursors in claim for the pharmaceutical compositions in claim 9 for preparing the drugs fit for the treatment of cell proliferation diseases, wherein the cell proliferation diseases are cancers.

14. A kit, including the pharmaceutically composition in claim 9, directions for use, and/or one or more kinds of other drugs fit for the treatment of cancer.

15. The platinum compound according to claim 1, where in $R_1$ and $R_2$ are the same or different, selected from hydrogen, alkyl, naphthenic base, alkoxy alkyl, alkylamino alkyl, heterocycle, alkenyl, and alkynyl respectively; the above alkyl, naphthenic base, alkoxy alkyl, alkyl amino alkyl, heterocycle, alkenyl, and alkynyl are optionally substituted by halogen, hydroxyl, alkoxy, alkyl, alkoxy alkyl, naphthenic base or heterocycle.

16. The platinum compound according to claim 1, wherein $R_1$ and $R_2$ may form saturated or unsaturated carboncycle or heterocycle with the atom connected, which may be optionally substituted, by halogen, hydroxyl, alkoxy, amino, alkyl, alkoxy alkyl, naphthenic base, or heterocycle; provided that the ring that formed by $R_1$, $R_2$ or $R_1$ and $R_2$ contains unsaturated bond, the atom of the unsaturated bond cannot be directly connected with nitrogen atom.

17. The platinum compound according to claim 1, wherein $R_3$ is selected from alkyl, naphthenic base and —$R_{31}$—O—$R_{32}$—; wherein $R_{31}$ and $R_{32}$ are independently selected from bond or alkyl; $R_{31}$ is connected with nitrogen atom; wherein above alkyl or naphthenic base is optionally substituted, by halogen, hydroxyl, alkoxy, alkyl, alkoxy alkyl, naphthenic base, or heterocycle.

18. The platinum compound according to claim 1, wherein $R_4$ and $R_5$ are the same or different, selected from: hydrogen, hydroxyl, alkyl, naphthenic base, alkoxy, alkoxy alkyl, alkylamino alkyl, heterocycle, alkenyl, or alkynyl respectively; wherein above alkyl, alkenyl, alkynyl, naphthenic base, alkoxy alkyl, alkylamino alkyl and heterocycle may be optionally substituted by halogen, hydroxyl, alkoxy, straight chain or branched-chain alkyl, alkoxy alkyl, naphthenic base and heterocycle.

19. The platinum compound according to claim 1, $R_4$, $R_5$ and the atoms they connected maybe together form a closed ring, which may be four-membered, five-membered, six-membered, seven-membered or eight-membered ring; the above ring is optionally condensed with other rings and optionally substituted by halogen, hydroxyl, alkoxy, straight chain or branched-chain alkyl, alkoxy alkyl, naphthenic base or heterocycle.

20. The platinum compound according to claim 5, wherein $R_1$ and $R_2$ are the same or different, selected from hydrogen, alkyl, naphthenic base, alkoxy alkyl, alkyl amino alkyl, heterocycle, alkenyl, or alkynyl; wherein above alkyl, alkoxy alkyl, alkyl amino alkyl, heterocycle, alkenyl, or alkynyl may be optionally substituted by halogen, hydroxyl, alkoxy, alkyl, alkoxy alkyl, naphthenic base, or heterocycle.

21. The platinum compound according to claim 5, wherein $R_1$ and $R_2$ may form saturated or unsaturated carboncycle or heterocycle with the atom connected; and the ring formed may be optionally substituted by halogen, hydroxyl, alkoxy, amino, alkyl, alkoxy alkyl, naphthenic base, or heterocycle; provided that the ring formed by $R_1$, $R_2$ or $R_1$ and $R_2$ contains unsaturated bond, the atom of the unsaturated bond cannot be directly connected with nitrogen atom.

22. The platinum compound according to claim 5, wherein $R_3$ is selected from alkyl, naphthenic base and —$R_{31}$—O—$R_{32}$—; $R_{31}$ and $R_{32}$ are independently selected from bond or alkyl; $R_{31}$ is connected with nitrogen atom; the above alkyl or naphthenic base may be optionally substituted by halogen, hydroxyl, alkoxy, alkyl, alkoxy alkyl, naphthenic base or heterocycle.

23. The platinum compound according to claim 5, wherein $R_6$ is selected from $(CH_2)_a$, a=3-5; wherein some —$CH_2$— may be substituted by —O—; one or more hydrogen of $(CH_2)_a$ may be substituted by fluorine, alkyl, hydroxyl or alkoxy.

24. The platinum compound according to claim 5, wherein $R_6$ is selected from $(CH_2)_a$, a=4; wherein some —$CH_2$— may be substituted by —O—; one or more hydrogen of $(CH_2)_a$ may be substituted by fluorine, alkyl, hydroxyl or alkoxy.

25. The platinum compound according to claim 5, wherein $R_7$ is selected from $(CH_2)_b$, wherein b=0-2; wherein some —$CH_2$— may be substituted by —O—, and one or more hydrogen of $(CH_2)_b$ may be substituted by halogen, alkyl, hydroxyl, hydroxyalkyl or alkoxy, heterocycle.

26. The platinum compound according to claim 5, wherein $R_8$ and $R_9$ are hydroxyalkyl.

27. The platinum compound according to claim 26, wherein $R_8$ and $R_9$ are hydroxymethyl.

28. The platinum compound according to claim 5, wherein $R_{10}$ and $R_{11}$ are hydroxyalkyl.

29. The platinum compound according to claim 28, wherein $R_{10}$ and $R_{11}$ are hydroxymethyl.

30. The platinum compound according to claim 5, wherein $R_{13}$ is —$CH_2$—.

31. The platinum compound according to claim 5, wherein $R_{14}$ is hydrogen.

32. The platinum compound according to claim 5, wherein $R_{15}$ is —$CH_2$—O—$CH_2$—.

33. The platinum compound according to claim 5, wherein

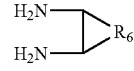

is selected from a group consisting of (±) trans-1,2-cyclohexyl diamine, (±) trans-1,2-cyclopentamethylenediamine, (±) trans-1,2-cyclo-butane diamine, and (±) trans-1,2-cyclopropane diamine.

34. The pharmaceutical composition according to claim 9, wherein the composition is in the form of injection.

35. The pharmaceutical composition according to claim 10, wherein said pharmaceutical composition contains 0.1%-100% (weight) of one or multiple compounds of the present invention.

36. The pharmaceutical composition according to claim 35, wherein said pharmaceutical composition contains 1%-100% (weight) of one or multiple compounds of the present invention.

37. The pharmaceutical composition according to claim 36, wherein said pharmaceutical composition contains 20%-100% (weight) of one or multiple compounds of the present invention.

38. The usage according to claim 13, wherein the cancers are breast cancer, lung cancer, colon cancer, gastric cancer, esophagus cancer, ovarian cancer, osteosarcoma, cervical cancer, bladder cancer, liver cancer, cerebroma, prostate cancer, or melanoma.

* * * * *